United States Patent
Saito et al.

(10) Patent No.: US 12,145,938 B2
(45) Date of Patent: Nov. 19, 2024

(54) COMPOUND AND POLYMER COMPOUND CONTAINING THE COMPOUND

(71) Applicant: JAPAN SCIENCE AND TECHNOLOGY AGENCY, Kawaguchi (JP)

(72) Inventors: Shohei Saito, Kyoto (JP); Hiroshi Yabu, Sendai (JP); Hiroya Abe, Sendai (JP)

(73) Assignee: JAPAN SCIENCE AND TECHNOLOGY AGENCY, Kawaguchi (JP)

( * ) Notice: Subject to any disclaimer, the term of this patent is extended or adjusted under 35 U.S.C. 154(b) by 0 days.

(21) Appl. No.: 18/063,331

(22) Filed: Dec. 8, 2022

(65) Prior Publication Data

US 2023/0125359 A1   Apr. 27, 2023
US 2024/0217976 A2   Jul. 4, 2024

Related U.S. Application Data

(62) Division of application No. 16/977,128, filed as application No. PCT/JP2019/008463 on Mar. 4, 2019, now Pat. No. 11,560,383.

(30) Foreign Application Priority Data

Mar. 5, 2018   (JP) .................................. 2018-039162

(51) Int. Cl.
C07D 487/04   (2006.01)
C07D 313/14   (2006.01)
C07D 471/06   (2006.01)

(52) U.S. Cl.
CPC ......... *C07D 487/04* (2013.01); *C07D 313/14* (2013.01); *C07D 471/06* (2013.01)

(58) Field of Classification Search
CPC ... C07D 487/04; C07D 313/14; C07D 471/06
See application file for complete search history.

(56) References Cited

U.S. PATENT DOCUMENTS 10,442,886 B2   10/2019   Yabu et al.
2018/0301632 A1   10/2018   Lee
(Continued)

FOREIGN PATENT DOCUMENTS

EP   3222694 A1   9/2017
JP   2014058606 A   4/2014
(Continued)

OTHER PUBLICATIONS

Office Action (Communication pursuant to Article 94(3) EPC) issued on Nov. 5, 2021, by the European Patent Office in corresponding European Application No. 19 763 778.8-1110. (7 pages).
(Continued)

*Primary Examiner* — Matthew P Coughlin
(74) *Attorney, Agent, or Firm* — Panitch Schwarze Belisario & Nadel LLP

(57) ABSTRACT

Provided is a compound having higher fluorescence quantum yield and higher optical stability than a conventional FLAP and a polymer compound containing the compound.

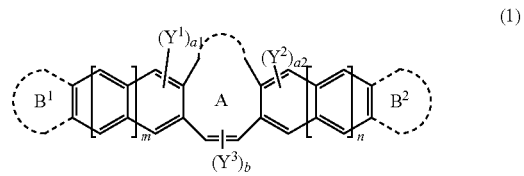

A: seven or eight-membered ring structure,
$Y^1$, $Y^2$, $Y^3$: halogen atom or the like,
a1: number of $Y^1$, a2: number of $Y^2$,
B: number of $Y^3$,
$0 \leq m$ and $n \leq 3$: when $1 \leq m \leq 3$, $Y^1$ may be substituted with a structure portion defined by m, when $1 \leq n \leq 3$, $Y^2$ may be substituted with a structure portion defined by n, and $B^1$, $B^2$: Formulas (2-1) to (2-3):

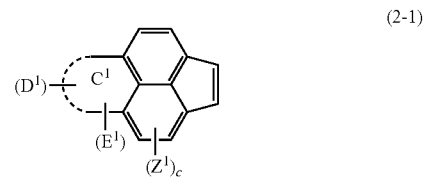

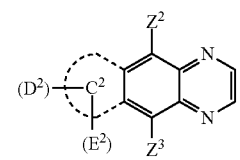

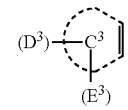

$C^1$, $C^2$, $C^3$: structure containing a cyclic hydrocarbon compound,
$D^1$, $D^2$, $D^3$: substructure that inhibits aggregation,
$E^1$, $E^2$, $E^3$: polymerizable substructure,
$Z^1$: hydrogen atom or the like,
c: number of substituent groups $Z^1$,
$Z^2$, $Z^3$: hydrogen atom or the like, and may form a ring with $C^2$.

12 Claims, 4 Drawing Sheets

(56) References Cited

U.S. PATENT DOCUMENTS

| | | | | |
|---|---|---|---|---|
| 2019/0031820 | A1* | 1/2019 | Yabu | C08G 61/08 |
| 2021/0002284 | A1 | 1/2021 | Saito et al. | |

FOREIGN PATENT DOCUMENTS

| | | | |
|---|---|---|---|
| JP | 2015113312 A | 6/2015 | |
| JP | 2015157769 A | 9/2015 | |
| WO | WO-2016080358 A1 * | 5/2016 | C07D 209/70 |

OTHER PUBLICATIONS

Chen et al., "Mechanically induced chemiluminescence from polymers incorporating a 1,2-dioxetane unit in the main chain", Nature Chemistry, vol. 4, Jul. 2012, pp. 559-562.

Coll et al., "Direct Lithiation of Hydroxyaromatics", Journal of Organic Chemistry, vol. 53, No. 22, 1988, pp. 5345-5348.

Crenshaw et al., "Deformation-Induced Color Changes in Melt-Processed Photoluminescent Polymer Blends", Chemical of Materials, vol. 15, No. 25, 2003, pp. 4717-4724.

Davis et al., "Force-induced activation of covalent bonds in mechanoresponsive polymeric materials", Nature, vol. 459, May 7, 2009, pp. 68-72.

Dorel et al., "Hydroacenes Made Easy by Gold(I) Catalysis", Supporting Information, Angewandte Chemie:International Edition, vol. 55, 2016, pp. 11120-11123.

Supporting Information for Dorel et al., "Hydroacenes Made Easy by Gold(I) Catalysis", Angewandte Chemie: International Edition, vol. 55, 2016, pp. 11120-11123. (164 pages).

Extended European Search Report issued on Dec. 7, 2020, by the European Patent Office in corresponding European Patent Application No. 19763778.8-1110. (11 pages).

Geerts et al., "Quaterrylenebis(dicarboximide)s: near infrared absorbing and emitting dyes", Journal of Materials Chemistry, vol. 8, No. 11, 1998, pp. 2357-2369.

Gossweiler et al., "Mechanochemical Activation of Covalent Bonds in Polymers with Full and Repeatable Macroscopic Shape Recovery", ACS Macro Letters, vol. 3, 2014, pp. 216-219.

Hori et al., "Synthesis and photophysical properties of multicolor emissive imidazoles", 28th Symposium on Physical organic Chemistry, 2017, p. 226.

Hospital et al., "Access to functionalised silver(I) and gold(I) N-heterocyclic carbenes by [2+3] dipolar cycloadditions", Dalton Transactions, vol. 41, 2012, pp. 6803-6812.

Howard et al., "Synthesis and Stereochemistry of Long-Chain Quinoxaline Metallocyclophanes", The Journal of Organic Chemistry, vol. 73, No. 7, 2008, pp. 2548-2553.

Hu et al., "Panchromatic chromophore-tetrapyrrole light-harvesting arrays constructed from Bodipy, perylene, terrylene, porphyrin, chlorin, and bacteriochlorin building blocks", New Journal of Chemistry, vol. 40, 2016, pp. 8032-8052.

Partial English translation of Kopranenkov, V. N , "Intermolecular Condensation of 2,3-bis (Dibromomethyl)-9,10-Anthraquinone", Zhumal Organicheskoi Khimii., vol. 13, vol. 6, 1977, pp. 1230-1231.

Kotani et al., "Chemical Functionalization of Fluorescent Molecular Force Probe", The 97th Annual Conference in Spring of the Chemical Society of Japan, 2017, 4 F8-05. (2 pages).

Kotani et al., "Flapping viscosity probe that shows polarity-independent ratiometnc fluorescence", Journal of Materials Chemistry C, vol. 5, 2017, pp. 5248-5256.

Electronic Supplementary Information for Kotani , et al., "Flapping viscosity probe that shows polarity-independent ratiometric fluorescence", Journal of Materials Chemistry C, vol. 5, 2017, pp. 5248-5256. (34 pages).

Kotani et al., "Force-induced Fluorescence Response of Mechanophore-doped Polyurethane Dependent on chemical Structures and Temperature", The 98th Annual Meeting of The Chemical Society of Japan, Funabashi, Japan, 98, Mar. 20-23, 2018, p. 1 B3-30, XP009523789.

Krinsky et al., "Modular Synthesis of Functionalisable Alkoxy-Tethered N-Heterocyclic Carbene Ligands and an Active Catalyst for Buchwald—Hartwig Aminations", Advanced Synthesis & Catalysis, vol. 356, 2014, pp. 460-474.

Levy, Louis A, "The Synthesis Of 2,3,6,7-Tetrasubstituted Naphthalenes: 2,3,6,7-Tetrachloronaphthalene", Synthetic Communications, vol. 13, No. 8, 1983, pp. 639-648.

Mestichelli et al., "Concise Copper-Catalyzed Synthesis of Tricyclic Biaryl Ether-Linked Aza-Heterocyclic Ring Systems", Organic Letters, vol. 15, No. 21, 2013, pp. 5448-5451.

Supporting Information for Mestichelli , et al., "Concise Copper-Catalyzed Synthesis of Tricyclic Biaryl Ether-Linked Aza-Heterocyclic Ring Systems", Organic Letters, vol. 15, No. 21, 2013, pp. 5448-5451. (276 pages).

International Search Report and Written Opinion with an English Translation of the International Searching Authority Issued on May 28, 2019, in corresponding International Application No. PCT/JP2019/008463. (14 pages).

Saito et al., "Chemistry", vol. 69, No. 5, May 2014, pp. 32-37.

Siram et al., "Acenaphtho[1,2-b]quinoxaline based low band gap copolymers for organic thin film transistor applications", Journal of Materials Chemistry, vol. 22, 2012, pp. 4450-4458.

Yamakado et al., "Compression of a Flapping Mechanophore Accompanied by Thermal Void Collapse in a crystalline Phase", Journal of the American Chemical Society, vol. 140, No. 20, May 10, 2018, pp. 6245-6248.

Yamakado et al., "Conformational Planarization Versus Singlet Fission: Distinct Excited-State Dynamics of Cayclooctatetraene-Fused Acene Dimers", Angew Chemie Int. Ed. , vol. 57, No. 19, Mar. 30, 2018, pp. 5438-5443.

Yuan , et al., "A π-Conjugated System with Flexibility and Rigidity That Shows Environment-Dependent RGB Luminescence", Journal of the American Chemical Society, vol. 135, 2013, pp. 8842-8845.

Yuan , et al., "Hybridization of a Flexible Cyclooctatetraene Core and Rigid Aceneimide Wings for Multiluminescent Flapping π Systems", Chemistry: A European Journal, vol. 20, 2014, pp. 2193-2200.

Yuan et al., "Hybridization of a Flexible Cyclooctatetraene Core and Rigid Aceneimide Wings for Multiluminescent Flapping π Systems", Chemistry: A European Journal, vol. 20, 2014, pp. 1-9.

Supporting Information for Yuan et al., "Hybridization of a Flexible Cyclooctatetraene Core and Rigid Aceneimide Wings for Multiluminescent Flapping π Systems", Chemistry: A European Journal, vol. 20, 2014, pp. 2193-2200. (32 pages).

Zhang et al., "General Synthetic Approach toward Geminal-Substituted Tetraarylethene Fluorophores with Tunable Emission Properties: X-ray Crystallography, Aggregation-Induced Emission and Piezolluorochromism", Chemistry of Materials, vol. 26, 2014, pp. 4433-4446.

Supporting Information for Zhang , et al., "General Synthetic Approach toward Geminal-Substituted Tetraarylethene Fluorophores with Tunable Emission Properties: X-ray Crystallography, Aggregation-Induced Emission and Piezofluorochromism", Chemistry of Materials, vol. 26, 2014, pp. 4433-4446. (34 pages).

* cited by examiner

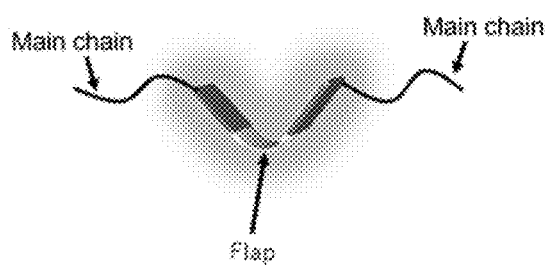 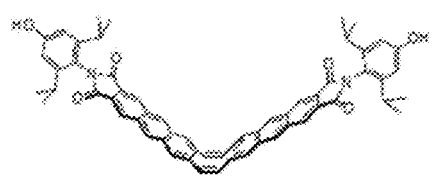
FIG. 2A  FIG. 2B
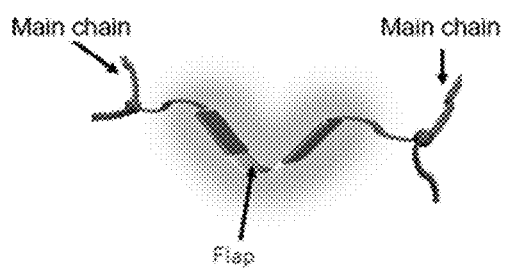 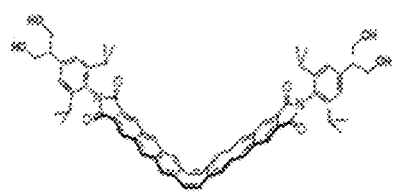
FIG. 3A  FIG. 3B

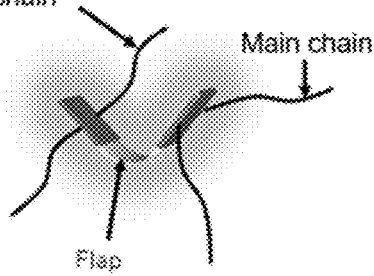
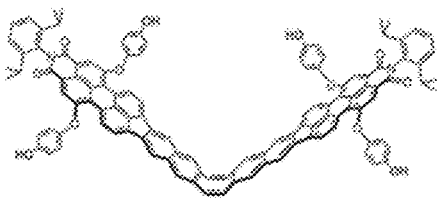
FIG. 4A  FIG. 4B
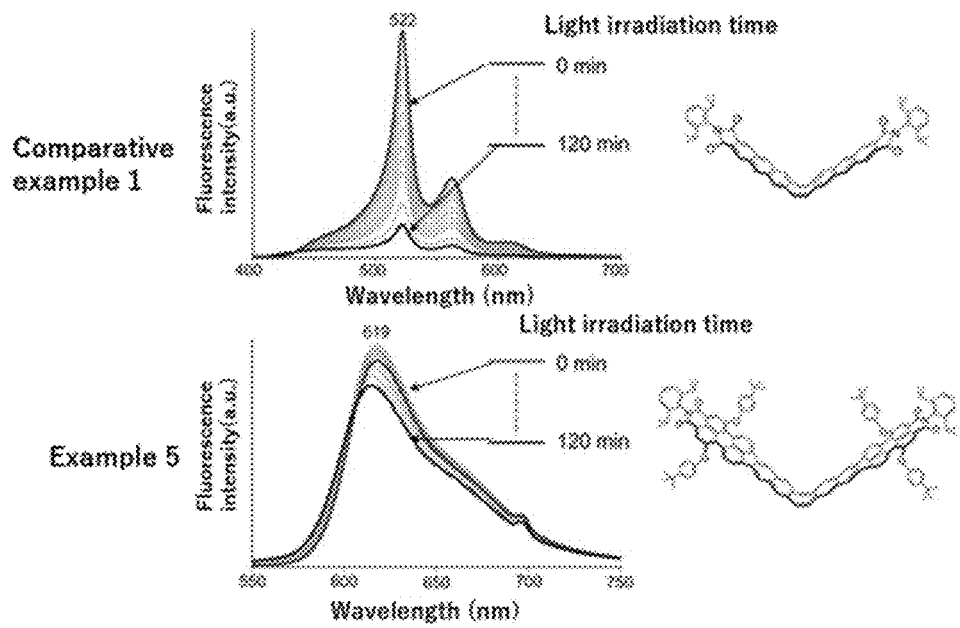
FIG.5

COMPOUND AND POLYMER COMPOUND CONTAINING THE COMPOUND

CROSS REFERENCE OF RELATED APPLICATIONS

This application is a division of U.S. patent application Ser. No. 16/977,128, filed on Sep. 1, 2020, now U.S. Pat. No. 11,560,383, entitled "COMPOUND AND POLYMER COMPOUND CONTAINING THE COMPOUND," which in turn is a national stage application of PCT/JP2019/008463, filed on Mar. 4, 2019, which in turn claims priority to Japanese Patent Application No. 2018-039162, filed on Mar. 5, 2018. The entire content of each of the prior applications is hereby incorporated by reference.

TECHNICAL FIELD

The present invention relates to a compound and a polymer compound containing the compound, in particular, relates to a polymer compound containing a compound that can visualize stress (Flexible Aromatic Photofunctional molecules, hereinafter, which may be denoted to as "FLAP") and a polymer compound containing the FLAP.

BACKGROUND ART

Functional materials have been developed for various uses in accordance with the characteristics of the functional material, and as an example thereof, attempts to visualize mechanical stress such as compression, expansion, bending, or the like applied on a material have been made.

As a method for visualizing mechanical stress, visualization using dispersion of excimers (see Non-Patent Literature 1), visualization using binding cleavage of chromatic molecules (see Non-Patent Literature 2), visualization using energy transform of chemical light emission (see Non-Patent Literature 3), visualization using emission of small molecules (see Non-Patent Literature 4), and the like are known.

Further, a mechanochromic material made of a polymer having a repetition unit of a urethane structure or an ester structure in which diarylbibenzofuranone structure is urethane-bound or ester-bound is known (see Patent Literature 1).

Synthetic π-conjugated molecules have been used as a composition of dyes or pigments, aromatic polymers, or optical storage material for a long time and, in recent years, have been widely and practically used as a form of organic EL photodynamic therapy agents, fluorescent probes, or the like. In general, since synthetic π-conjugated molecules are made of rigid aromatic rings and multiple bonds (mainly, $sp^2$ carbon), a significant majority of them necessarily have rigid structure.

Such rigid structure has many advantages also in the physical property, for example, an intended shape of a molecular framework can be synthesized, and because of small structure deformation, the structure exhibits a slow non-radiometric deactivation process and high light emission efficiency. On the other hand, it can also be considered that a rigid fundamental molecular framework makes it difficult to transform the physical property caused by flexibility of the structure in a similar manner to an inorganic material, and only the expression of a static physical property is reached. Thus, the present inventors create a compound having condensed-ring luminescent anthraceneimide as two rigid "wings" at opposed positions of flexible conjugated eight-membered ring (cyclooctatetraene) as illustrated in FIG. 1A. This compound exhibits inversion behavior between a V-form and a Λ-form in response to the motion of the eight-membered ring and emits blue light in a V-form state and green light in a planar state due to a change of electronic structure involved by the motion of the steric structure, as illustrated in FIG. 1B (see Non-Patent Literatures 5 and 6).

By using the compound described above, it is possible to visually indicate the degree of a mechanical stimulation (mechanical stress) applied on a material by means of a change of the light emission color. As a visualization technology using the compound described above, for example, the present inventors have found that, by dispersing the compound described above in an adhesive agent, it is possible to visualize curing process of the adhesive agent and, in addition, determine a portion of insufficient curing in a contactless manner (see Patent Literature 2).

Further, the present inventors have found (i) that, since a mechanochromic resin in which a mechanochromic light-emitting material represented by the following Formula (P1) or (P2) is cross-linked to a polymer chain changes the light emission color thereof quickly and reversibly due to expansion and compression, stress applied to a material can be visualized in real time and (ii) that, although synthesis of a mechanochromic resin is difficult with mere introduction of a polymerizable group to anthraceneimide dimers or naphthaleneimide dimers disclosed in Non-Patent Literatures 5 to 7, a mechanochromic resin in which a mechanochromic light-emitting material is cross-linked can be synthesized by introducing substituent group that inhibits aggregation between anthraceneimide dimers or naphthaleneimide dimers and the polymerizable group (see Patent Literature 3).

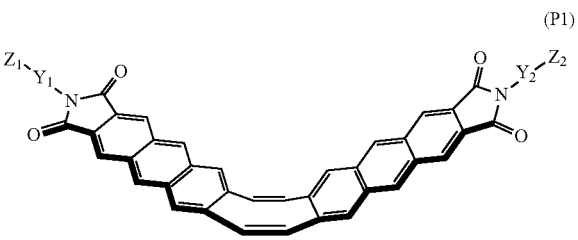

(P1)

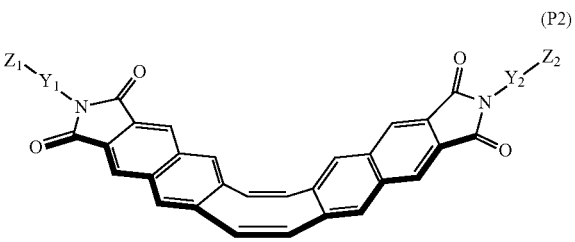

(P2)

(In the formula, $Y_1$ and $Y_2$ denote substituent groups that inhibit aggregation of a mechanochromic light-emitting material expressed by Formula (1) and may be the same or may be different. $Z_1$ and $Z_2$ denote polymerizable groups and may be the same or may be different. Note that elements $Y_1$ and $Y_2$ and elements $Z_1$ and $Z_2$ in Formulas (P1) and (P2) are different from elements $Y_1$ and $Y_2$ and an element Z of the present invention described later.)

CITATION LIST

Patent Literature

Patent Literature 1: Japanese Patent Application Publication No. 2014-58606
Patent Literature 2: Japanese Patent Application Publication No. 2015-113312
Patent Literature 3: International Publication No. WO2016/080358

Non-Patent Literature

Non-Patent Literature 1: Christoph Weder et al., "Deformation-Induced Color Changes in Melt-Processed Photoluminescent Polymer Blends", Chem Mater, 2003, 15, p 4717-4724
Non-Patent Literature 2: N. R. Sottos et al., "Force-induced activation of covalent bonds in mechanoresponsive polymeric materials", Nature, 2009, Vol. 459, p 68-72
Non-Patent Literature 3: R. P. Sijbesma et al., "Mechanically induced chemiluminescence from polymers incorporating a 1,2-dioxetane unit in the main chain", Nature Chem, 2012, Vol. 4, p 559-562
Non-Patent Literature 4: Stephen L. Craig et al., "Mechanochemical Activation of Covalent Bonds in Polymers with Full and Repeatable Macroscopic Shape Recovery", ACS Macro Lett, 2014, 3, p 216-219
Non-Patent Literature 5: S. Saito et al., "A π-Conjugated System with Flexibility and Rigidity That Shows Environment-Dependent RGB Luminescence", Journal of the American Chemical Society, 2013, 135, p 8842-8845
Non-Patent Literature 6: S. Saito et al., "Hybridization of a Flexible Cyclooctatetraene Core and Rigid Aceneimide Wings for Multiluminescent FLAPping π Systems", Chemistry-A European Journal, 2014, 20, p 2193-2200
Non-Patent Literature 7: Shouhei Saito, Shigehiro Yamaguchi, "Move π-conjugated Framework to Cause Expression of Function", CHEMISTRY, Vol. 69, No. 5 (2014), p 32-37

SUMMARY OF INVENTION

Technical Problem to be Solved by the Invention

When the FLAP is applied to a sensor or the like, higher spatial resolution in distortion detection is preferable. Thus, there is a demand for a molecule having higher fluorescence quantum yield and higher optical stability than the conventional FLAP.

The present invention has been made to solve the problems described above and intends to provide a compound having high fluorescence quantum yield and high optical stability and a polymer compound containing the compound.

Solution to Problem

The present invention is directed to a compound and a polymer compound containing the compound described below.

[1]
A compound represented by a following general Formula (1):

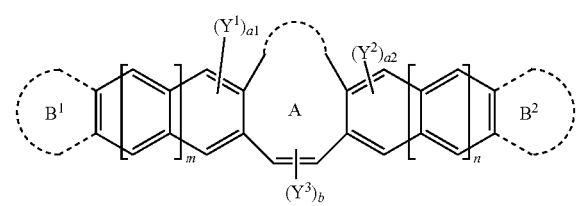

(1)

wherein in general Formula (1),
A denotes a seven-membered ring or eight-membered ring structure that may have a substituent group and forms a conjugated system with a benzene ring bound to A,
$Y^1$ and $Y^2$ each denote, independently, a substituent group selected from a halogen atom, an aliphatic hydrocarbon group with 1-20 carbons that may have a substituent group, an aryl group with 6-20 carbons that may have a substituent group, an alkoxy group with 1-10 carbons that may have a substituent group, an cyano group, and a heterocyclic compound group having 5-8 atoms forming a ring, and when a plurality of substituent groups $Y^1$ and $Y^2$ are provided, respective substituent groups may be the same as each other or may be different from each other,
a1 denotes the number of the substituent groups $Y^1$, and a2 denotes the number of the substituent groups $Y^2$,
$Y^3$ denotes a substituent group selected from a halogen atom, an alkyl group with 1-20 carbons that may have a substituent group, an alkynyl group with 2-20 carbons that may have a substituent group, an aryl group with 6-20 carbons that may have a substituent group, an alkoxy group with 1-10 carbons that may have a substituent group, a carboxylic acid ester group with 2-20 carbons that may have a substituent group, a carboxyl group, a hydroxyl group, and a cyano group, when a plurality of substituent groups $Y^3$ are provided, respective substituent groups may be the same as each other or may be different from each other,
b denotes the number of the substituent groups $Y^3$,
m and n each denote, independently, an integer greater than or equal to 0 and less than or equal to 3, when m is an integer greater than or equal to 1 and less than or equal to 3, $Y^1$ may be substituted with a structure portion defined by m, and similarly, when n is an integer greater than or equal to 1 and less than or equal to 3, $Y^2$ may be substituted with a structure portion defined by n, and
$B^1$ and $B^2$ each denote, independently, any of the structures represented by general Formulas (2-1) to (2-3):

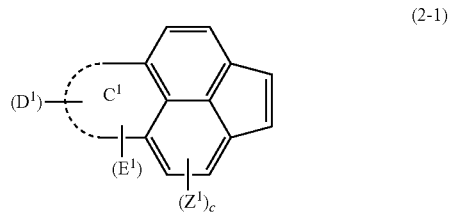

(2-1)

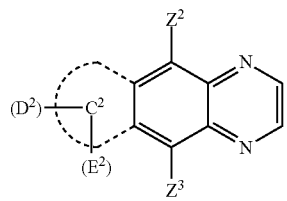

(2-2)

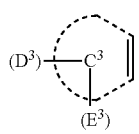

(2-3)

wherein in general Formulas (2-1) to (2-3), $C^1$ denotes a structure containing a cyclic hydrocarbon compound, $C^2$ and $C^3$ each denote a structure containing a cyclic hydrocarbon compound but may have no structure containing a cyclic hydrocarbon compound, and when $C^2$ and $C^3$ have no structure containing a cyclic hydrocarbon compound, $D^2$, $D^3$, $E^2$, and $E^3$ are arranged in a framework of a compound represented by general Formula (1), $D^1$, $D^2$, and $D^3$ each denote a substructure that inhibits aggregation, $E^1$, $E^2$, and $E^3$ each denote a polymerizable substructure, $Z^1$ each denote, independently, a substituent group selected from a hydrogen atom, a halogen atom, an alkyl group with 1-20 carbons that may have a substituent group, an alkynyl group with 2-20 carbons that may have a substituent group, an aryl group with 6-20 carbons that may have a substituent group, an alkoxy group with 1-10 carbons that may have a substituent group, and a cyano group and may form a ring with $C^1$, and when a plurality of substituent groups $Z^1$ are provided, respective substituent groups may be the same as each other or may be different from each other, c denotes the number of substituent groups $Z^1$, and $Z^2$ and $Z^3$ each denote, independently, a substituent group selected from a hydrogen atom, a halogen atom, an alkyl group with 1-20 carbons that may have a substituent group, an alkynyl group with 2-20 carbons that may have a substituent group, an aryl group with 6-20 carbons that may have a substituent group, an alkoxy group with 1-10 carbons that may have a substituent group, and a cyano group, and $Z^2$ and $Z^3$ may each form a ring with $C^2$, independently.

[2]

The compound according to [1] above, wherein in the general Formula (1), the A is represented by general Formula (3) or (4):

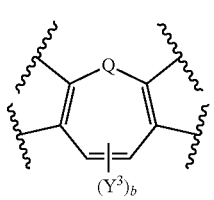

(3)

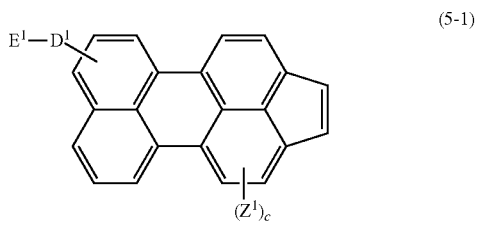

(4)

wherein in general Formula (4), Q denotes an O atom, an S atom, a Se atom, or an N atom or a P atom having an alkyl group as a substituent group.

[3]

The compound according to [1] or [2] above, wherein in the general Formula (1), the $B^1$ and $B^2$ have any structure of general Formulas (5-1) to (5-3):

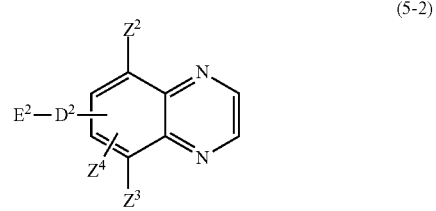

(5-1)

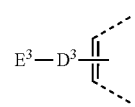

(5-2)

(5-3)

wherein $Z^4$ in general Formula (5-2) is the same as the $Z^2$ and $Z^3$.

[4]

The compound according to any one of [1] to [3] above, wherein the $E^1$, $E^2$, and $E^3$ each denote a polymerizable substituent group.

[5]

The compound according to any one of [1] to [4] above, wherein the $D^1$, $D^2$, and D' have any of following structures:

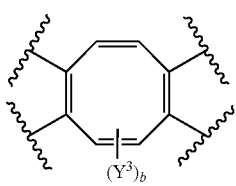
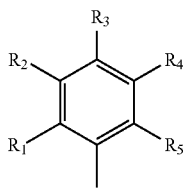
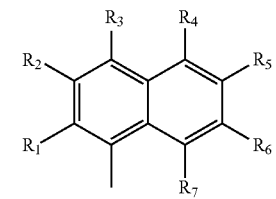

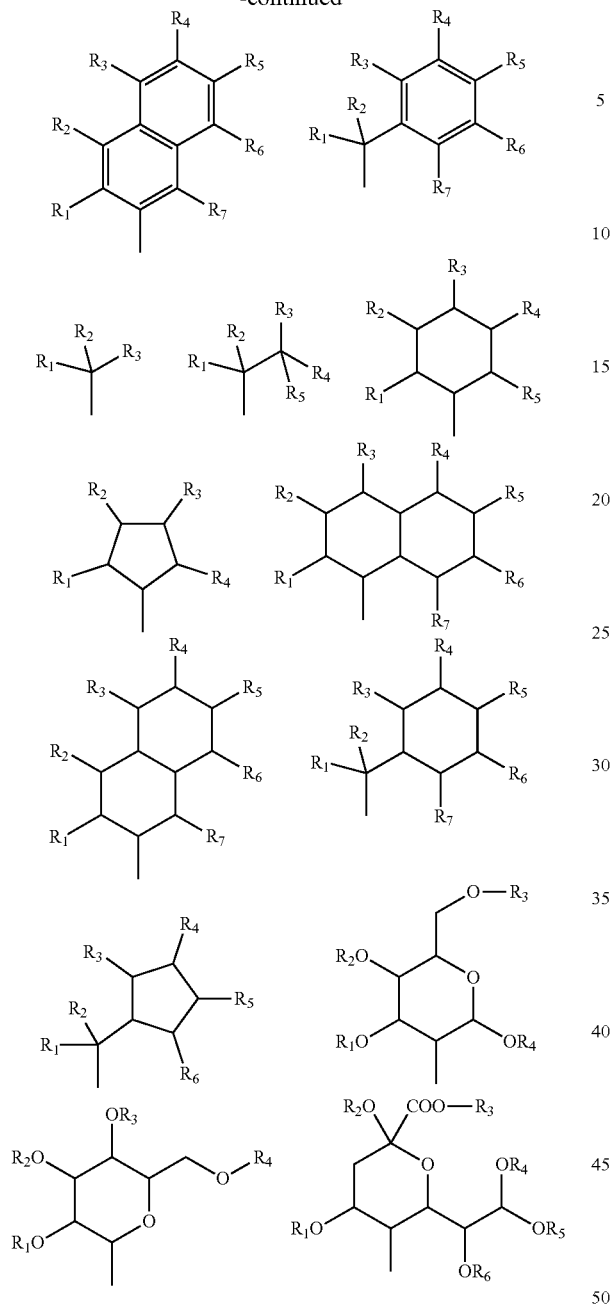
wherein $R_1$ to $R_7$ each denote H, a linear, branched, or cyclic alkyl group with 1-20 carbons, an aryl group with 6-20 carbons, F, Cl, Br, I, $CF_3$, $CCl_3$, CN, or $OCH_3$, and $R_1$ to $R_7$ may be the same or different.
[6]
The compound according to any one of [1] to [5] above, wherein the $E^1$, $E^2$, and $E^3$ are any of the Formulas (E-1) to (E-18):
(E-1)
(E-2)
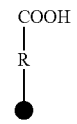
(E-3)
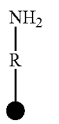
(E-4)
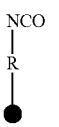
(E-5)
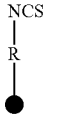
(E-6)
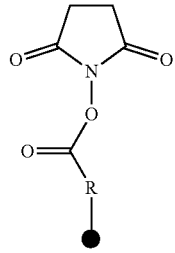
(E-7)
(E-8)
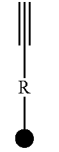
(E-9)
(E-10)
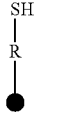
(E-11)
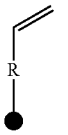

-continued

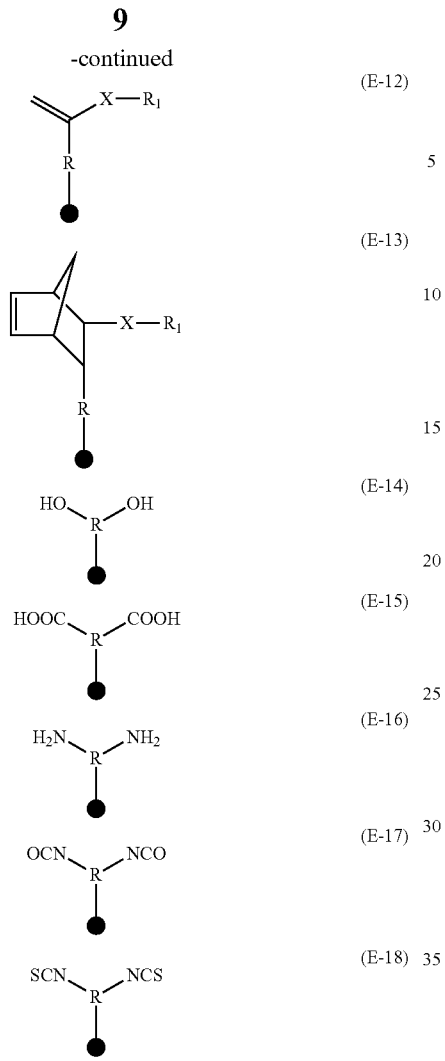

wherein in the Formulas (E-12) and (E-13), X denotes amide or ester but may not be included, $R_1$ in the Formulas (E-12) and (E-13) is the same as $R_1$ according to claim 5, R in Formulas (E-1) to (E-18) denotes a linear, branched, or cyclic alkyl group with 1-20 carbons or an aryl group with 6-20 carbons, R in Formulas (E-1) to (E-11) may not be included, and each filled circle represents $D^1$, $D^2$, or $D^3$.

[7]

The compound according to [3] above, wherein in the general Formula (1), the $B^1$ and $B^2$ have any of structures of the general Formulas (5-1) and (5-2).

[8]

The compound according to [3] above,
wherein in the general Formula (1), the $B^1$ and $B^2$ have a structure of the general Formula (5-3), and
wherein m and n of a compound represented by the general Formula (1) are 0 or 3.

[9]

The compound according to any one of [1] to [8] above, wherein in the general Formula (1),
the a1
denotes an integer of 0 to 3 when m is 0, and
denotes an integer that $Y^1$ can be substituted in accordance with the number 0 to m when m is an integer greater than or equal to 1 and less than or equal to 3,
the a2
denotes an integer of 0 to 3 when n is 0, and
denotes an integer that $Y^2$ can be substituted in accordance with the number 0 to n when n is an integer greater than or equal to 1 and less than or equal to 3, and
the b denotes an integer greater than or equal to 0 and less than or equal to 4, The compound according to any one of [2] to [9] above, wherein in the general Formula (1), the A is the general Formula (4).

The compound according to any one of [1] to [10] above, wherein in the general Formula (1), the b is an integer greater than or equal to 1 and less than or equal to 4.

A polymer compound made by polymerizing the compound described in any one of [1] to [11] above.

The polymer compound according to above, wherein the compound is bound to the polymer compound via a urethane binding in the polymer compound.

The polymer compound according to or above further comprising, in a main chain of the polymer compound, a chemical structure included in the compound.

The polymer compound according to or above further comprising a cross-linked site made of a chemical structure included in the compound.

Advantageous Effect of Invention

With a use of the compound of the present invention, fluorescence quantum yield can be increased, and optical stability is improved.

BRIEF DESCRIPTION OF DRAWINGS

FIG. 2A and FIG. 2B illustrate examples including a FLAP in the main chain of a polymer.

FIG. 3A and FIG. 3B illustrate examples including a FLAP as a cross-linkage point of a polymer.

FIG. 4A and FIG. 4B illustrate other examples including a FLAP as a cross-linkage point of a polymer.

FIG. 5 is a graph illustrating a result of fluorescence attenuation measured in Example 5 and Comparative example 1.

DESCRIPTION OF EMBODIMENTS

Figure 1A:
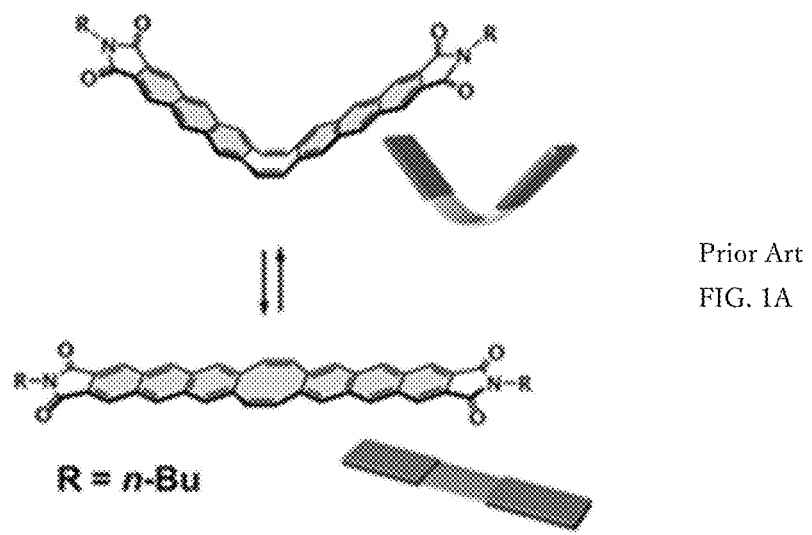
FIG. 1A and FIG. 1B illustrate a compound having condensed-ring luminescent anthraceneimide as two rigid "wings" at opposed positions of flexible conjugated eight-membered ring (cyclooctatetraene) disclosed in Non-Patent Literature 5.
Figure 1B:
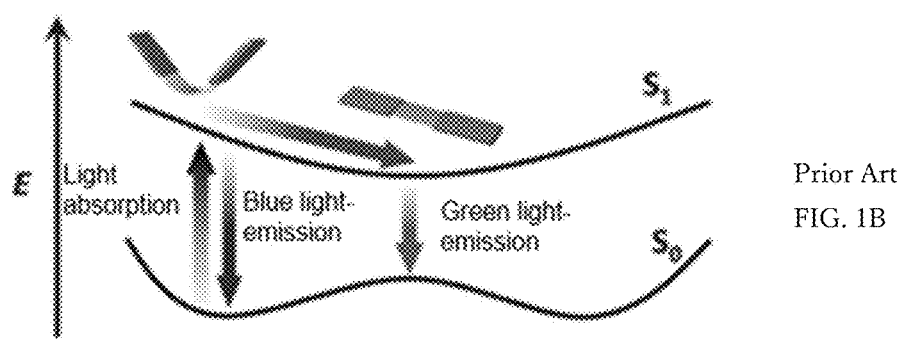

Embodiments of a compound (FLAP) and a polymer compound containing the compound will be specifically described below.

First, in the present invention, "FLAP" means a compound that can visualize stress because the light emission wavelength changes due to mechanical stress and the light emission color changes.

The compound (FLAP) of the present invention is represented by the following Formula (1).

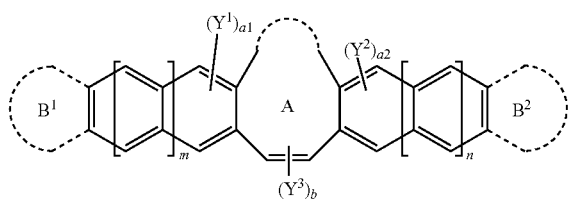

(1)

Symbols in the above general Formula (1) are defined as follows.

Symbol A denotes a seven-membered ring structure or an eight-membered ring structure that may have a substituent group and forms a conjugated system with a benzene ring bound to A.

Symbols $Y^1$ and $Y^2$ each denote, independently, a substituent group selected from a halogen atom, an aliphatic hydrocarbon group with 1-20 carbons that may have a substituent group, an aryl group with 6-20 carbons that may have a substituent group, an alkoxy group with 1-10 carbons that may have a substituent group, an cyano group, and a heterocyclic compound group having 5-8 atoms forming a ring. When a plurality of substituent groups $Y^1$ and $Y^2$ are provided, respective substituent groups may be the same as each other or may be different from each other.

Symbol a1 denotes the number of the substituent groups $Y^1$, and symbol a2 denotes the number of the substituent groups $Y^2$.

Symbol $Y^3$ denotes a substituent group selected from a halogen atom, an alkyl group with 1-20 carbons that may have a substituent group, an alkynyl group with 2-20 carbons that may have a substituent group, an aryl group with 6-20 carbons that may have a substituent group, an alkoxy group with 1-10 carbons that may have a substituent group, a carboxylic acid ester group with 2-20 carbons that may have a substituent group, a carboxyl group, a hydroxyl group, and a cyano group. When a plurality of substituent groups $Y^3$ are provided, respective substituent groups may be the same as each other or may be different from each other.

Symbol b denotes the number of the substituent groups $Y^3$. Symbol b denotes an integer greater than or equal to 0 and less than or equal to 4.

Symbol m and n each denote, independently, an integer greater than or equal to 0 and less than or equal to 3. Note that, when m is an integer greater than or equal to 1 and less than or equal to 3, $Y^1$ may be substituted with a structure portion defined by m. Similarly, when n is an integer greater than or equal to 1 and less than or equal to 3, $Y^2$ may be substituted with a structure portion defined by n.

Note that, when m is an integer greater than or equal to 1 and less than or equal to 3, a1 denotes an integer that $Y^1$ can be substituted in accordance with the number 0 to m. When m is 0, a1 denotes an integer of 0 to 3.

Further, when n is an integer greater than or equal to 1 and less than or equal to 3, a2 denotes an integer that $Y^2$ can be substituted in accordance with the number 0 to n. When n is 0, a2 denotes an integer of 0 to 3.

Symbols $B^1$ and $B^2$ each denote, independently, any of the structures represented by the following general Formulas (2-1) to (2-3). Note that the double bond at the right end of the structure represented by the following general Formulas (2-1) to (2-3) corresponds to the double bond at the right end of $B^1$ of the compound and the double bond at the left end of $B^2$ of the compound represented by the above general Formula (1).

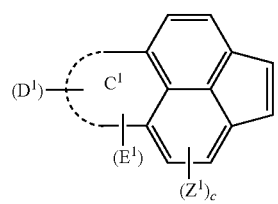

(2-1)

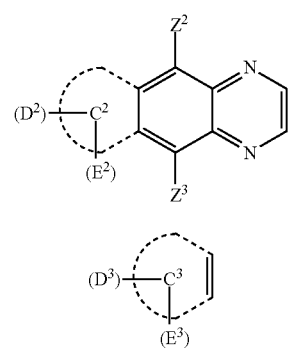

(2-2)

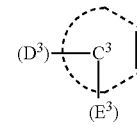

(2-3)

Symbols in general Formulas (2-1) to (2-3) are defined as follows.

Symbol $C^1$ denotes a structure containing a cyclic hydrocarbon compound.

Symbols $C^2$ and $C^3$ each denote a structure containing a cyclic hydrocarbon compound but may have no structure containing a cyclic hydrocarbon compound. When $C^2$ and $C^3$ have no structure containing a cyclic hydrocarbon compound, $D^2$, $D^3$, $E^2$, and $E^3$ are arranged in a framework of a compound represented by general Formula (1).

Symbols $D^1$, $D^2$, and $D^3$ each denote a substructure that inhibits aggregation.

Symbols $E^1$, $E^2$, and $E^3$ each denote a polymerizable substructure.

Note that, while $D^1$ to $D^3$ and $E^1$ to $E^3$ may be arranged in $C^1$ to $C^3$, respectively, $E^1$ to $E^3$ may be bound to $D^1$ to $D^3$.

Symbols $Z^1$ each denote, independently, a substituent group selected from a hydrogen atom, a halogen atom, an alkyl group with 1-20 carbons that may have a substituent group, an alkynyl group with 2-20 carbons that may have a substituent group, an aryl group with 6-20 carbons that may have a substituent group, an alkoxy group with 1-10 carbons that may have a substituent group, and a cyano group and may form a ring with $C^1$. When a plurality of substituent groups $Z^1$ are provided, respective substituent groups may be the same as each other or may be different from each other.

Symbol c denotes the number of substituent groups $Z^1$. Symbol c denotes an integer greater than or equal to 1 and less than or equal to 4.

Symbols $Z^2$ and $Z^3$ each denote, independently, a substituent group selected from a hydrogen atom, a halogen atom, an alkyl group with 1-20 carbons that may have a substituent group, an alkynyl group with 2-20 carbons that may have a substituent group, an aryl group with 6-20 carbons that may have a substituent group, an alkoxy group with 1-10 carbons that may have a substituent group, and a cyano group. Symbols $Z^2$ and $Z^3$ may each form a ring with $C^2$, independently.

In the above general Formula (1), A is not particularly limited as long as the electronic structure changes due to conformation (three-dimensional positional relationship of constituent atoms) change to form a π-conjugated system and may be, for example, an eight-membered ring represented by the following general Formula (3) or a seven-membered ring represented by the following general Formula (4).

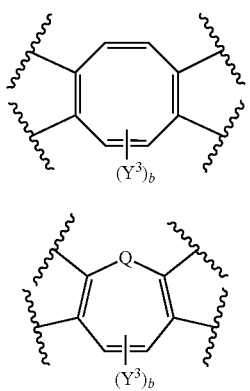

In the above general Formula (4), symbol Q denotes an O atom, an S atom, a Se atom, or an N atom or a P atom having an alkyl group as a substituent group. Q is preferably O atom, an S atom, or an N atom or a P atom having an alkyl group as a substituent group, more preferably O atom or an N atom having an alkyl group, and much more preferably an O atom.

The above aliphatic hydrocarbon group with 1-20 carbons that may have a substituent group described for $Y^1$ and $Y^2$ is not particularly limited and may be an alkyl group, an alkenyl group, an alkynyl group or the like with 1-20 carbons, and preferably an alkyl group with 1-20 carbons or an alkynyl group with 2-20 carbons.

With respect to the alkyl group with 1-20 carbons that may have the substituent group described for the above $Y^1$, $Y^2$, $Y^3$, $Z^1$, $Z^2$, and $Z^3$, the alkyl group with 1-20 carbons may be any form of a straight chain, a branch, or a ring and may be, as a specific example, methyl, ethyl, n-propyl, 2-propyl, n-butyl, 1-methylpropyl, 2-methylpropyl, tert-butyl, n-pentyl, 1-methylbutyl, 1-ethylpropyl, tert-pentyl, 2-methylbutyl, 3-methylbutyl, 2,2-dimethylpropyl, n-hexyl, 1-methylpentyl, 1-ethylbutyl, 2-methylpentyl, 3-methylpentyl, 4-methylpentyl, 2-methylpentane-3-yl, 3,3-dimethylbutyl, 2,2-dimethylbutyl, 1,1-dimethylbutyl, 1,2-dimethylbutyl, 1,3-dimethylbutyl 2,3-dimethylbutyl, 1-ethylbutyl, 2-ethylbutyl, heptyl, octyl, nonyl, decyl, undecyl, dodecyl, tridecyl, tetradecyl, pentadecyl, hexadecyl, heptadecyl, octadecyl, nonadecyl, equosyl, cyclopropyl, cyclobutyl, cyclopentyl, cyclohexyl, or the like, for example. Among the alkyl groups described above, the alkyl group with 1-16 carbons is preferable. Further, a substituent group may be phenyl, mesityl, 2,6-diisopropylphenyl, 3,5-di(tert-butyl)phenyl, 4-tert-butylphenyl, or the like.

With respect to the alkynyl group with 6-20 carbons that may have the substituent group described for the above $Y^1$, $Y^2$, $Y^3$, $Z^1$, $Z^2$, and $Z^3$, the alkynyl group may be ethynyl group, 1-propynyl group, 1-butynyl group, 1-pentynyl group, 1-hexynyl group, 1-heptynyl group, 1-octinyl group, 1-nonynyl group, 1-decynyl group, 1-undecynyl group, 1-dodecynyl group, 1-tridecynyl group, 1-tetradecynyl group, 1-pentadecynyl group, 1-hexadecynyl group, 1-heptadecynyl group, 1-octadecynyl group, 1-nonadecynyl group, 1-icosynyl group, 1-henicosynyl group, 1-docosynyl group, 1-tricosynyl group, 1-tetracosynyl group, 1-pentacosynyl group, 1-hexacosynyl group, 1-heptacosynyl group, 1-octacosynyl group, 1-nonacosynyl group, and 1-triakontinyl group. Preferably, the alkynyl may be ethynyl group, 1-propynyl group, 1-butynyl group, 1-pentinyl group, 1-hexynyl group, 1-heptynyl group, 1-octinyl group, 1-nonynyl group, 1-decynyl group, 1-undecynyl group, 1-dodecynyl group, 1-tridecynyl group, 1-tetradecynyl group, 1-pentadecynyl group, 1-hexadecynyl group, 1-heptadecynyl group, 1-octadecynyl group, 1-nonadecynyl group, 1-icosynyl group, and the like. A specific example of the substituent group may be trimethylsilyl, triethylsilyl, triisopropylsilyl, triphenylsilyl, tert-butyl-dimethylsilyl, tert-butyl-diphenylsilyl, phenyl, mesityl, 2,6-diisopropylphenyl, 3,5-di(tert-butyl)phenyl, 4-tert-butylphenyl, or the like.

With respect to the aryl group with 6-20 carbons that may have the substituent group described for the above $Y^1$, $Y^2$, $Y^3$, $Z^1$, $Z^2$, and $Z^3$, a specific example of the aryl group with 6-20 carbons may be phenyl, indenyl, pentalenyl, naphthyl, azulenyl, fluorenyl, phenanthrenyl, anthracenyl, acenaphthylenyl, biphenylenyl, naphthacenyl, pyrenyl, or the like. Note that the substituent group may be the same as the substituent group of the above alkyl group with 1-20 carbons.

With respect to the alkoxy group with 1-10 carbons that may have the substituent group described for the above $Y^1$, $Y^2$, $Y^3$, $Z^1$, $Z^2$, and $Z^3$, a specific example of the alkoxy group with 1-10 carbons may be methoxy group, ethoxy group, propoxy group, isopropoxy group, butoxy group, isobutoxy group, tert-butoxy group, pentyloxy group, hexyloxy group, cyclohexyloxy group, heptyloxy group, octyloxy group, 2-ethylhexyloxy group, nonyloxy group, decyloxy group, or the like. Note that the substituent group may be the same as the substituent group of the above alkyl group with 1-20 carbons.

With respect to the heterocyclic compound group having 5-8 atoms forming a ring described for the above $Y^1$ and $Y^2$, a specific example may be pyrrolidine, tetrahydrofuran, tetrahydrothiophene, pyrrole, furan, thiophene, piperidine, tetrahydropyran, tetrahydrothiopyran, pyridine, pyrillium ion, thiapyran, hexamethyleneimine, hexamethylene oxide, hexamethylene sulfide, azatropyridene, oxycycloheptatriene, thiotropyridene, imidazole, pyrazole, oxazole, thiazole, imidazoline, dioxane, morpholine, thiazine, triazole, tetrazole, dioxolane, pyridazine, pyrimidine, pyrazine, or the like.

With respect to the carboxylic acid ester group with 2-20 carbons that may have a substituent group described for the above $Y^3$, a specific example of the carboxylic acid ester group may be carboxylic acid methyl ester group, carboxylic acid ethyl ester group, carboxylic acid propyl ester group, carboxylic acid butyl ester group, or the like. Note that the substituent group may be the same as the substituent group of the above alkyl group with 1-20 carbons.

With respect to the above $Y^1$, $Y^2$, $Y^3$, $Z^1$, $Z^2$, and $Z^3$, any combination by which aggregation of the synthesized FLAP is inhibited may be employed, and the combination having a solubility that enables sufficient dissolution to a solvent is preferable. In terms of the above, a smaller number of substituent groups described above is preferable, and a compound having none of the above $Y^1$, $Y^2$, $Y^3$, $Z^1$, $Z^2$, and $Z^3$, specifically, having no substituent group is preferable.

Note that, in the above general Formula (4), a specific chemical substructure when one $Y^3$ described above is provided (that is, b=1) may preferably be, for example, a ring structure (4-1) as included in a methylated dibenzoxepine based compound, a ring structure (4-2) as included in an N-methylated dibenzoazepine based compound, or the like as described below.

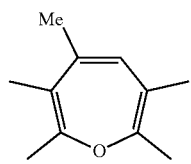
(4-1)

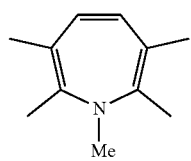
(4-2)

Further, a more specific example of any of the structures represented by the above general Formulas (2-1) to (2-3) may be any of the structures of the following general Formulas (5-1) to (5-3).

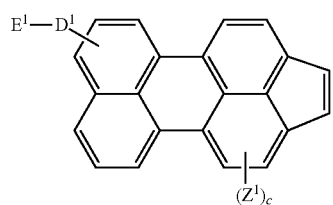
(5-1)

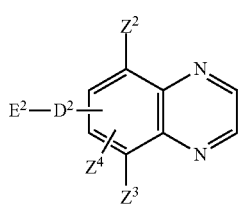
(5-2)

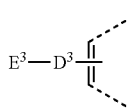
(5-3)

$Z^4$ in the above general Formula (5-2) is the same as the above $Z^2$ and $Z^3$.

A specific example of each substructure of the above $D^1$, $D^2$, and $D^3$ that inhibits aggregation may be the structure described below. Note that, since the substructure that inhibits aggregation can suppress aggregation of a compound (FLAP) in a solution, reaction for cross-linkage to a polymer chain or introduction of the compound (FLAP) into a polymer chain becomes easier.

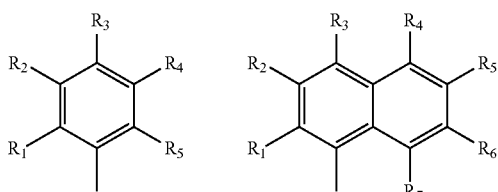

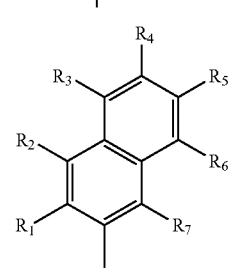

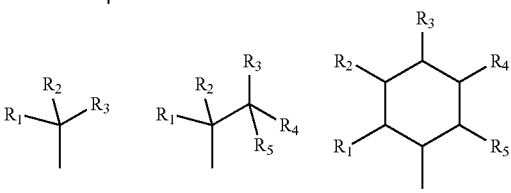

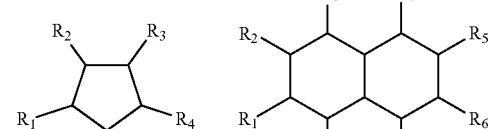

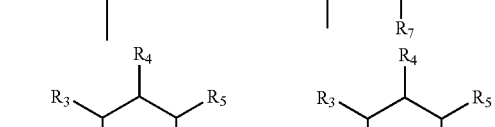

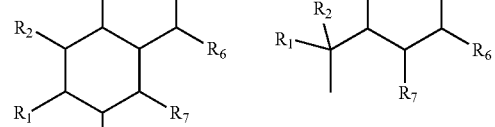

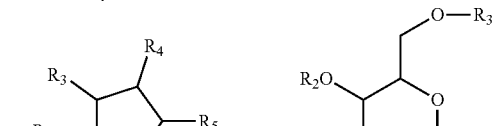

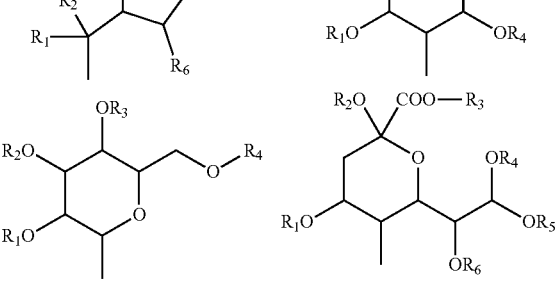

Symbols $R_1$ to $R_7$ of the above substructure that inhibits aggregation each denote H, a linear, branched, or cyclic alkyl group with 1-20 carbons, an aryl group with 6-20 carbons, F, Cl, Br, I, $CF_3$, $CCl_3$, CN, or $OCH_3$. $R_1$ to $R_7$ may be the same or different. Note that the linear, branched, or cyclic alkyl group with 1-20 carbons and the aryl group with 6-20 carbons are the same as the specific example described for the above $Y^1$, $Y^2$, $Y^3$, $Z^1$, $Z^2$, and $Z^3$.

A specific example of the polymerizable substituent group denoted as the above $E^1$, $E^2$, and $E^3$ may be (E-1) to (E-18) represented below.

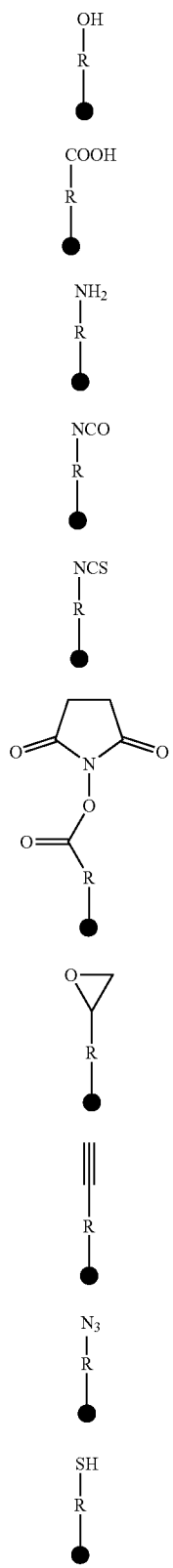

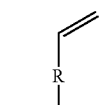

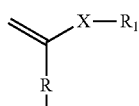

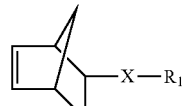

While R in Formulas (E-1) to (E-18) denotes a linear, branched, or cyclic alkyl group with 1-20 carbons or an aryl group with 6-20 carbons, R in Formulas (E-1) to (E-13) may not be included. Each symbol. (filled circle) represents $D^1$, $D^2$, or $D^3$.

Each substituent group represented by the above Formulas (E-1) to (E-7) is a monomer for polyaddition and polycondensation reaction. The monomer represented by (E-1) may be hydroxymethyl, hydroxyethyl, hydroxypropyl, hydroxybutyl, hydroxypentyl, hydroxyhexyl, hydroxycyclopropyl, hydroxyphenyl, or the like. The monomer represented by (E-2) may be carboxymethyl, carboxyethyl, carboxypropyl, carboxybutyl, carboxypentyl, carboxyhexyl, carboxycyclopropyl, carboxyphenyl, or the like. The monomer represented by (E-3) may be aminomethyl, aminoethyl, aminopropyl, aminobutyl, aminopentyl, aminohexyl, aminocyclopropyl, aminophenyl, or the like. The monomer represented by the above Formula (E-4) may be methyl isocyanate, ethyl isocyanate, propyl isocyanate, butyl isocyanate, pentyl isocyanate, hexyl isocyanate, cyclopropyl isocyanate, phenyl isocyanate, or the like. The monomer represented by (E-5) may be methyl isothiocyanate, ethyl isothiocyanate, propyl isothiocyanate, butyl isothiocyanate, pentyl isothiocyanate, hexyl isothiocyanate, cyclopropyl isothiocyanate, phenyl isothiocyanate, or the like. The monomer represented by the above Formula (E-6) is a monomer resulted by activating a general ester by N-hydroxysuccinimide (NHS) and may be methyl NHS ester, ethyl NHS ester, propyl NHS ester, butyl NHS ester, pentyl NHS ester, hexyl NHS ester, cyclopropyl NHS ester, phenyl NHS ester, or the like. The monomer represented by the above Formula (E-7) may be glycidyl, ethyl epoxy, propyl epoxy, butyl epoxy, pentyl epoxy, hexyl epoxy, cyclopropyl epoxy, phenyl epoxy, or the like.

Each substituent group represented by the above Formulas (E-8) to (E-11) is a click-reaction monomer. The monomer represented by the above Formula (E-8) may be methylacetylene, ethylacetylene, propylacetylene, butylacetylene, pentylacetylene, hexylacetylene, cyclopropylacetylene, phenylacetylene, or the like. The monomer represented by the above Formula (E-9) may be methyl azide, ethyl azide, propyl azide, butyl azide, pentyl azide, hexyl azide, cyclopropyl azide, phenyl azide, or the like. The monomer represented by the above Formula (E-10) may be methylthiol, ethylthiol, propylthiol, butylthiol, pentylthiol, hexylthiol, cyclopropylthiol, thiophenol, or the like. The monomer represented by the above Formula (E-11) may be vinyl, ethyl vinyl, propyl vinyl, butyl vinyl, pentyl vinyl, hexyl vinyl, cyclopropyl vinyl, phenyl vinyl, maleimide, or the like. Note that, in the case of click reaction, azide and alkynes are reacted, and vinyl and thiol are reacted. Therefore, when the monomer of Formula (E-8) is used as a polymerizable group, the polymerizable monomer forming a polymer chain described later can use a monomer having azide. Similarly, a polymerizable monomer having alkyne can be used when the monomer of Formula (E-9) is used as a polymerizable group, a polymerizable monomer having vinyl can be used when the monomer of Formula (E-10) is used as a polymerizable group, and a polymerizable monomer having thiol can be used when the monomer of Formula (E-11) is used as a polymerizable group.

In the above Formulas (E-12) and (E-13), symbol X denotes amide or ester but may not be included. $R_1$ in the above Formulas (E-12) and (E-13) is the same as $R_1$ of the above substructure that inhibits aggregation.

The substituent group represented by the above Formula (E-12) is a radical polymerization monomer and, specifically, may be alkyl(meth)acrylamides such as methyl(meth)acrylamide, ethyl(meth)acrylamide, n-propyl(meth)acrylamide, 2-propyl(meth)acrylamide, n-butyl(meth)acrylamide, 1-methylpropyl(meth)acrylamide, 2-methylpropyl(meth)acrylamide, tert-butyl(meth)acrylamide, n-pentyl(meth)acrylamide, 1-methylbutyl(meth)acrylamide, 1-ethylpropyl(meth)acrylamide, tert-pentyl(meth)acrylamide, 2-methylbutyl(meth)acrylamide, 3-methylbutyl(meth)acrylamide, 2,2-dimethylpropyl(meth)acrylamide, n-hexyl(meth)acrylamide, or the like; alkyl(meth)acrylates such as methyl(meth)acrylate, ethyl(meth)acrylate, n-propyl(meth)acrylate, 2-propyl(meth)acrylate, n-butyl(meth)acrylate, 1-methylpropyl(meth)acrylate, 2-methylpropyl(meth)acrylate, tert-butyl(meth)acrylate, n-pentyl(meth)acrylate, 1-methylbutyl(meth)acrylate, 1-ethylpropyl(meth)acrylate, tert-pentyl(meth)acrylate, 2-methylbutyl(meth)acrylate, 3-methylbutyl(meth)acrylate, 2,2-dimethyl propyl(meth)acrylate, n-hexyl(meth)acrylate, 1-methylpentyl(meth)acrylate, 1-ethylbutyl(meth)acrylate, 2-methylpentyl(meth)acrylate, 3-methylpentyl(meth)acrylate, 4-methylpentyl(meth)acrylate, 2-methylpentane-3-yl(meth)acrylate, 3,3-dimethylbutyl(meth)acrylate, 2,2-dimethylbutyl(meth)acrylate, 1,1-dimethylbutyl(meth)acrylate, 1,2-dimethylbutyl(meth)acrylate, 1,3-dimethylbutyl(meth)acrylate, 2,3-dimethylbutyl(meth)acrylate, 1-ethylbutyl(meth)acrylate, 2-ethylbutyl(meth)acrylate, heptyl(meth)acrylate, or the like; cyclopentene or cyclohexene such as propylene, 2-methyl-1-propylene, 1-butene, 2-methyl-1-butene, 3-methyl-1-butene, 3,3-dimethyl-1-butene, 3-methyl-2-ethyl-1-butene, 2,3-dimethyl-1-butene, 2-tert-butyl-3,3-dimethyl-1-butene, 1-pentene, 2-methyl-1-pentene, 3-methyl-1-pentene, 4-methyl-1-pentene, 2-methyl-3-ethyl-1-pentene, 2,4,4-trimethyl-1-pentene, 1-hexene, or the like; vinylaryls such as vinylbenzene (styrene), 1-vinylindene, 5-vinylindene, 1-vinylpentarene, 1-vinylnaphthalene, 2-vinylnaphthalene, 2-vinylazulene, 9-vinyl-9H-fluorene, 2-vinyl-9H-fluorene, 1-vinylphenanthrene, 2-vinylphenanthrene, 3-vinylphenanthrene, 6-vinylphenanthrene, 8-vinylphenanthrene, 1-vinylanthracene, 2-vinylanthracene, 9-vinylanthracene, 1-vinylacenaphthylene, 2-vinylbiphenylene, 1-vinylnaphthacene, 2-vinylnaphthacene, 1-vinylpyrene, 4-vinylpyrene, or the like; or the like.

The substituent group represented by the above Formula (E-13) may be a metathesis ring-opening polymerization monomer and, specifically, may be norbornene, acetyl norbornene, 5-methyl norbornene, 5-ethyl norbornene, 5-butyl norbornene, 5-phenyl norbornene, 5-benzyl norbornene, 5-acetyl norbornene, 5-acetyloxy norbornene, 5-methoxycarbonyl norbornene, 5-ethoxycarbonyl norbornene, 5-methyl-5-methoxycarbonyl norbornene, or the like.

Each substituent group represented by the above Formulas (E-14) to (E-18) is a bifunctional monomer. The monomer represented by the above Formula (E-14) may be methyl diol, ethyl diol, propyl diol, butyl diol, pentyl diol, hexyl diol, cyclopropyl diol, phenyl diol, or the like. The monomer represented by the above Formula (E-15) may be methyl dicarboxylic acid, ethyl dicarboxylic acid, propyl dicarboxylic acid, butyl dicarboxylic acid, pentyl dicarboxylic acid, hexyl dicarboxylic acid, cyclopropyl dicarboxylic acid, phenyl dicarboxylic acid, or the like. The monomer represented by the above Formula (E-16) may be methyl diamine, ethyl diamine, propyl diamine, butyl diamine, pentyl diamine, hexyl diamine, cyclopropyl diamine, phenyl diamine, or the like. The monomer represented by the above Formula (E-17) may be methyl diisocyanate, ethyl diisocyanate, propyl diisocyanate, butyl diisocyanate, pentyl diisocyanate, hexyl diisocyanate, cyclopropyl diisocyanate, phenyl diisocyanate, or the like. The monomer represented by the above Formula (E-18) may be methyl diisothiocyanate, ethyl diisothiocyanate, propyl diisothiocyanate, butyl diisothiocyanate, pentyl diisothiocyanate, hexyl diisothiocyanate, cyclopropyl diisothiocyanate, phenyl diisothiocyanate, or the like. In the same manner as the case of click reaction, also when a bifunctional monomer is used, a polymerizable monomer that can react with the bifunctional monomer can be suitably selected as a polymerizable monomer used for polymer chain. For example, when the polymerizable group contains dicarboxylic acid, a polymerizable monomer containing diamine or diol can be selected.

The compound represented by the above general Formula (1) may be the following compounds, for example. Note that the following examples are provided for better understanding and are not intended to limit the compound represented by general Formula (1).

21 22
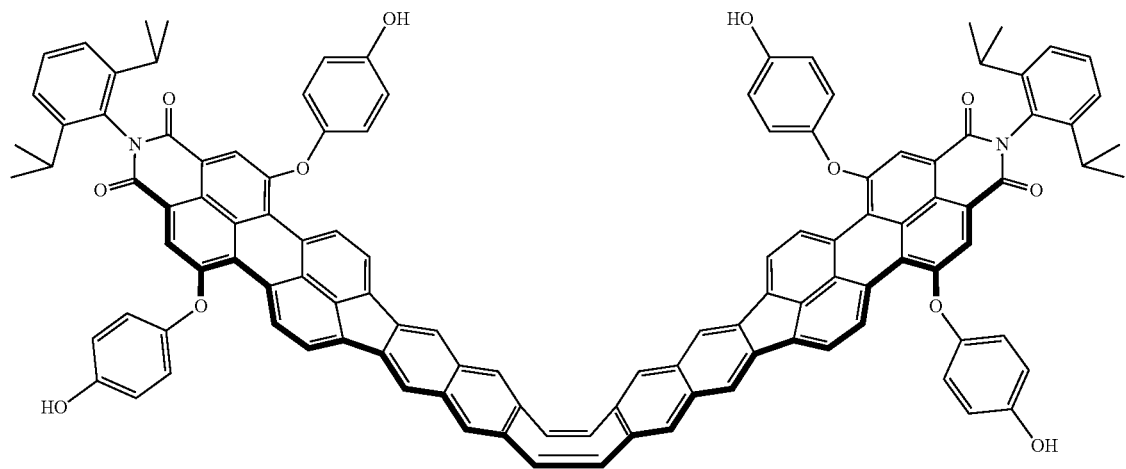
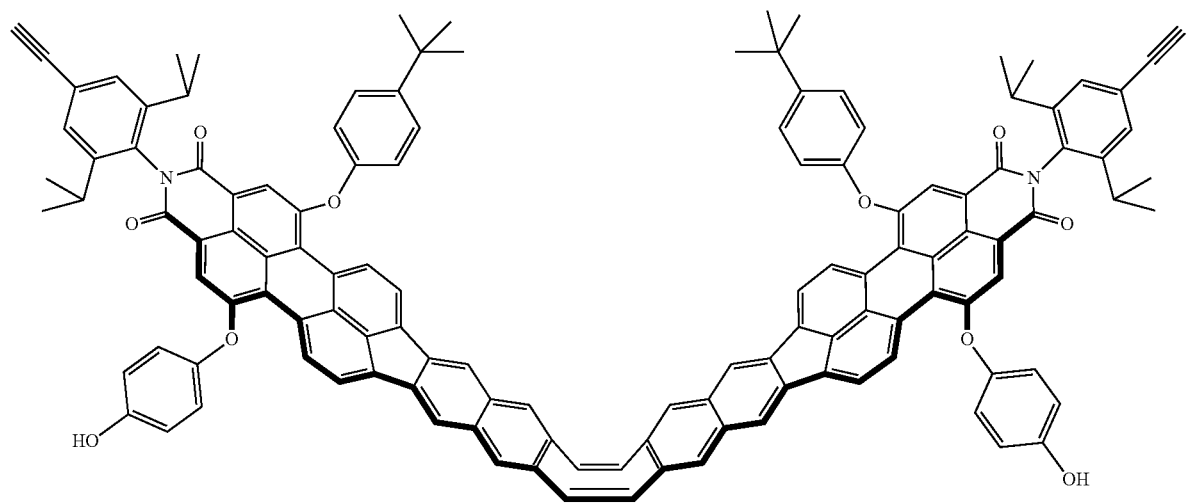
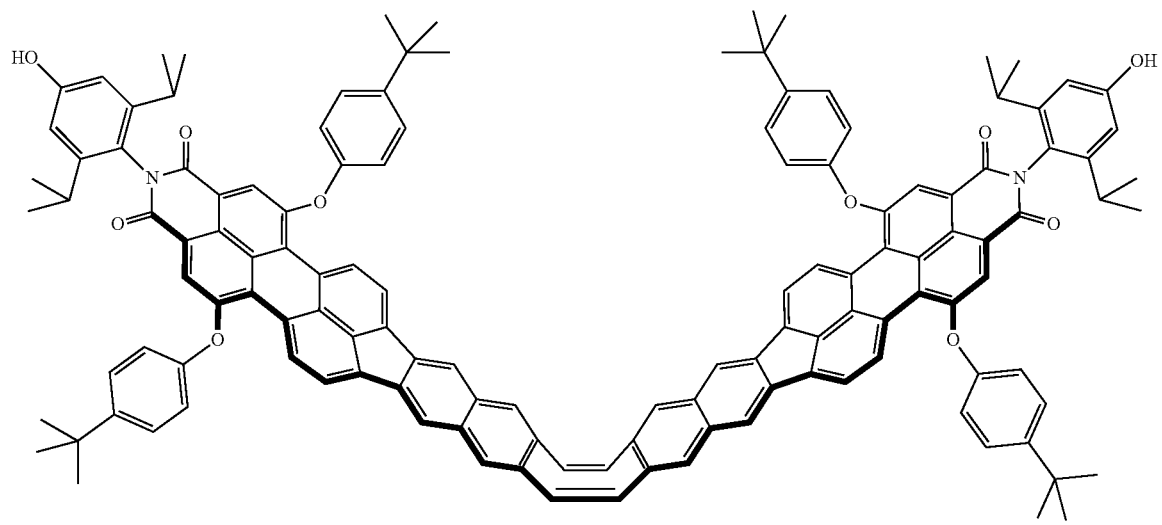

-continued
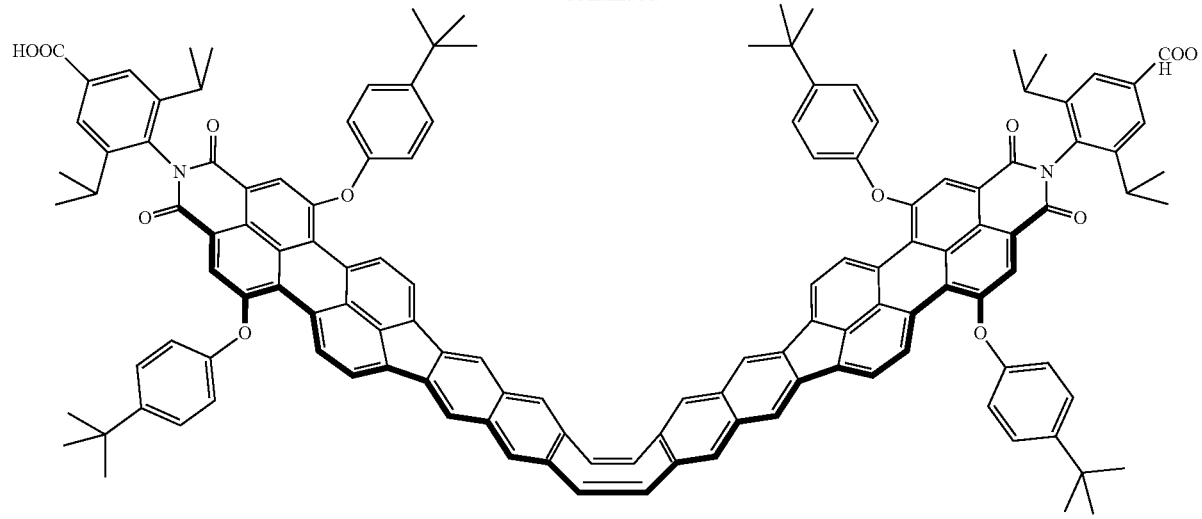
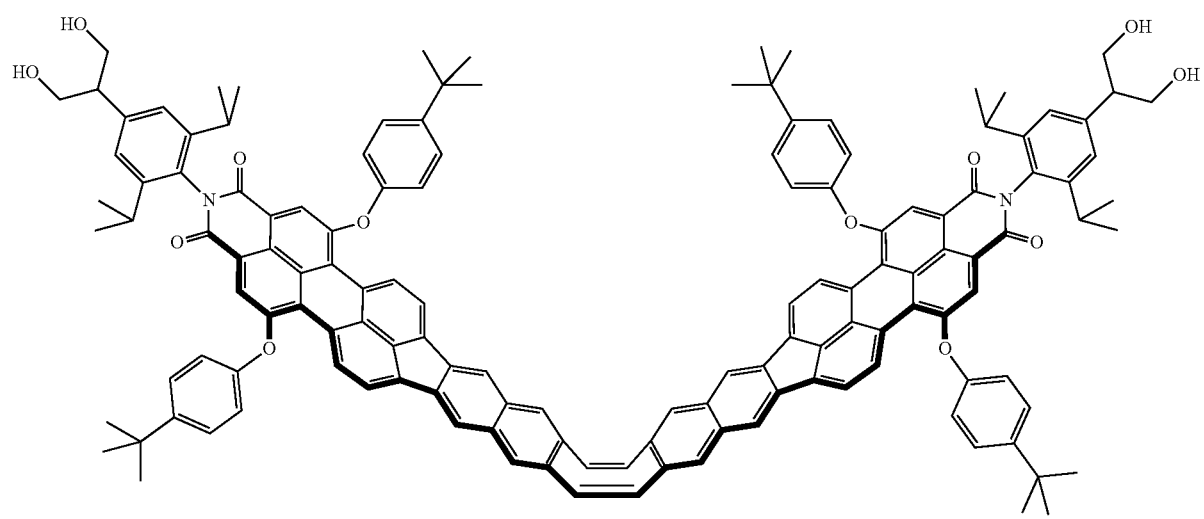
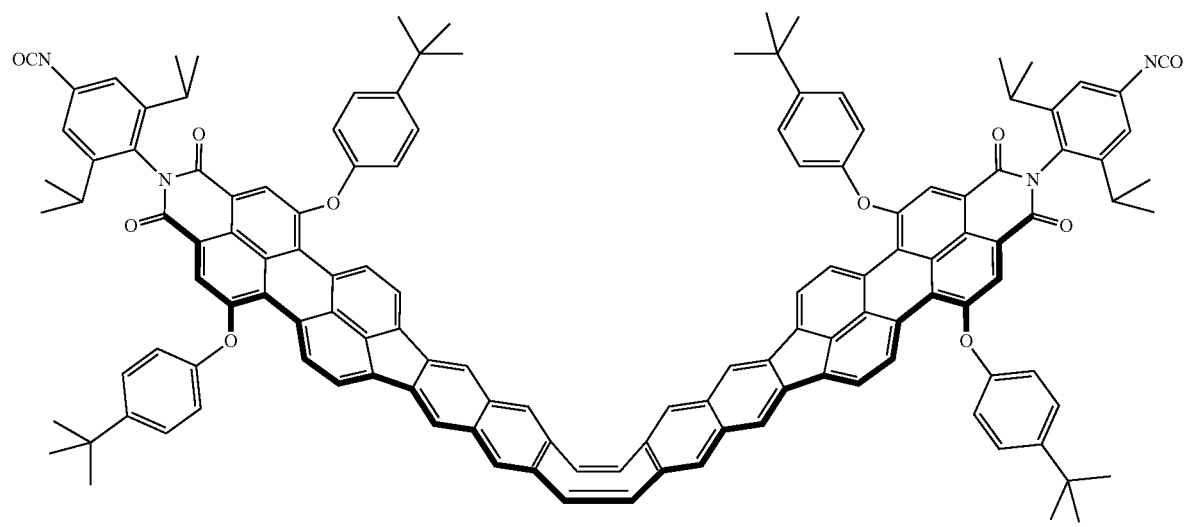

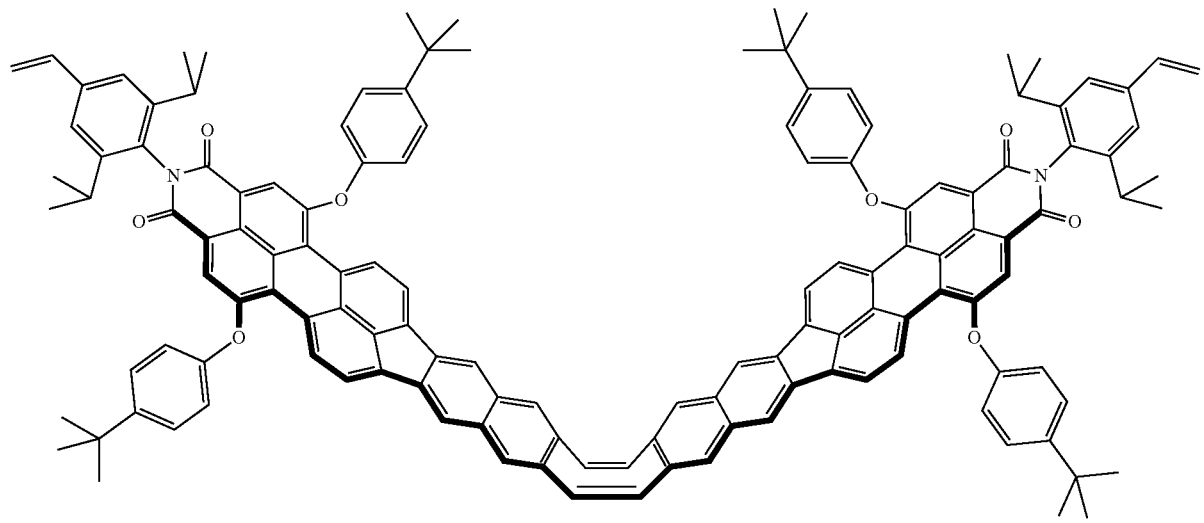
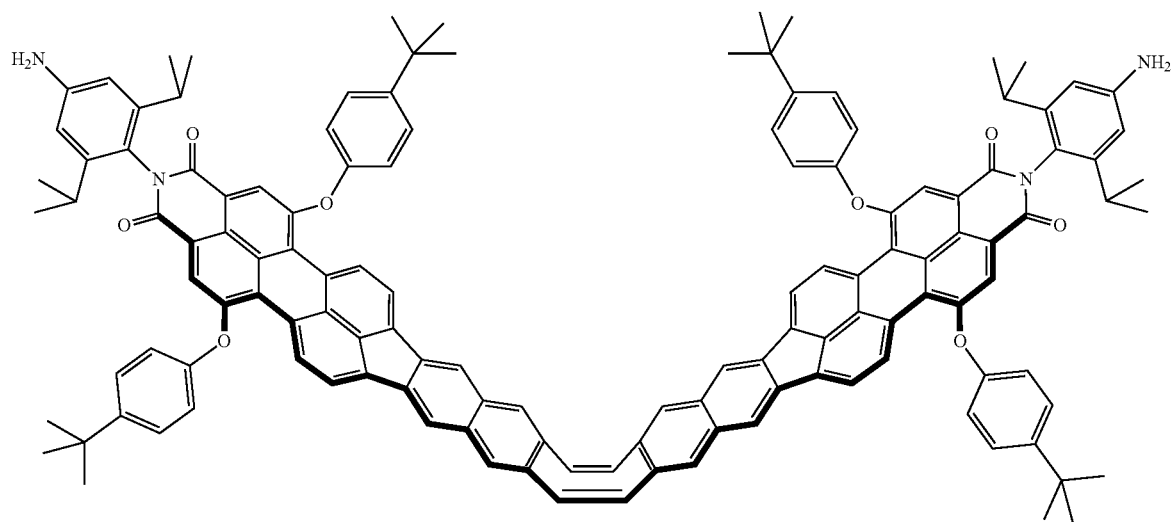
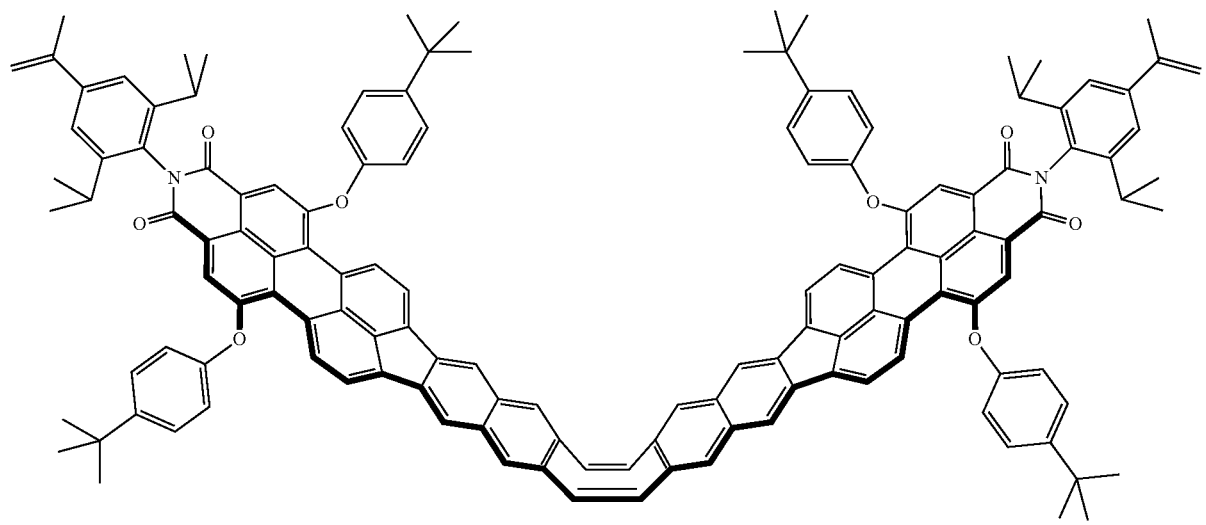

27
28
-continued
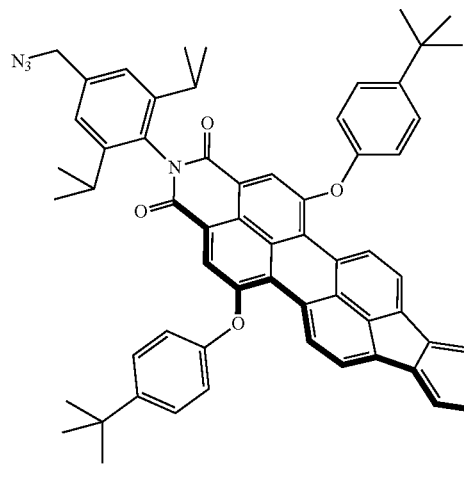
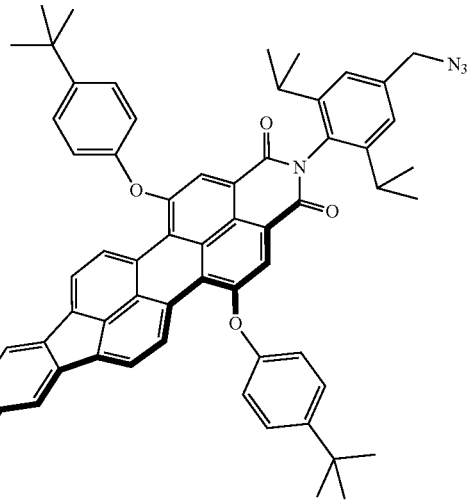
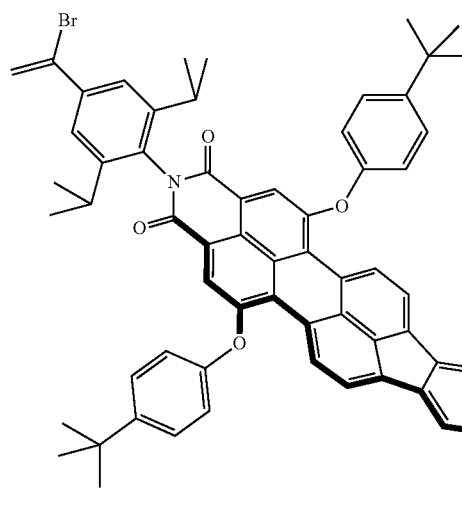
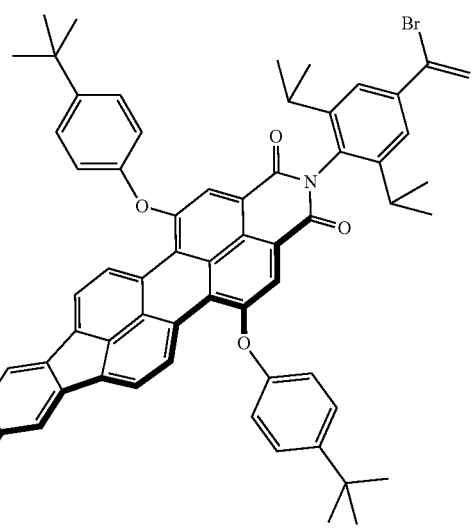
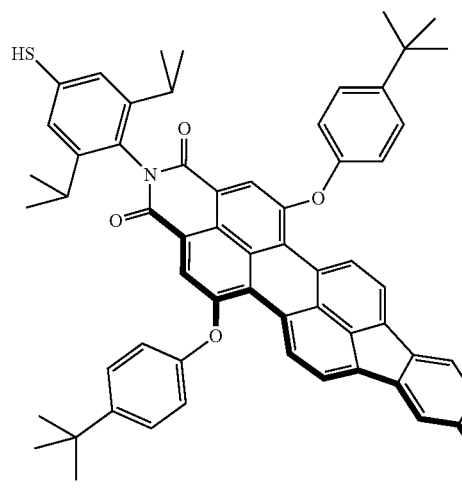
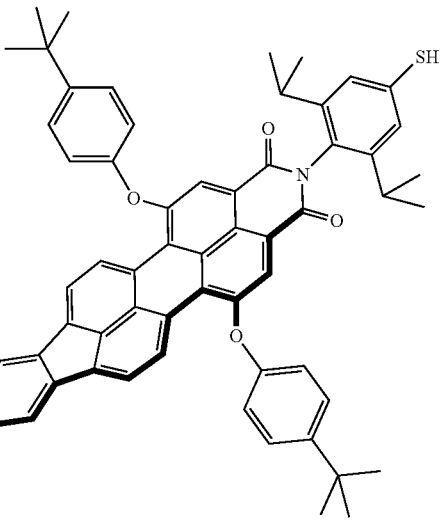

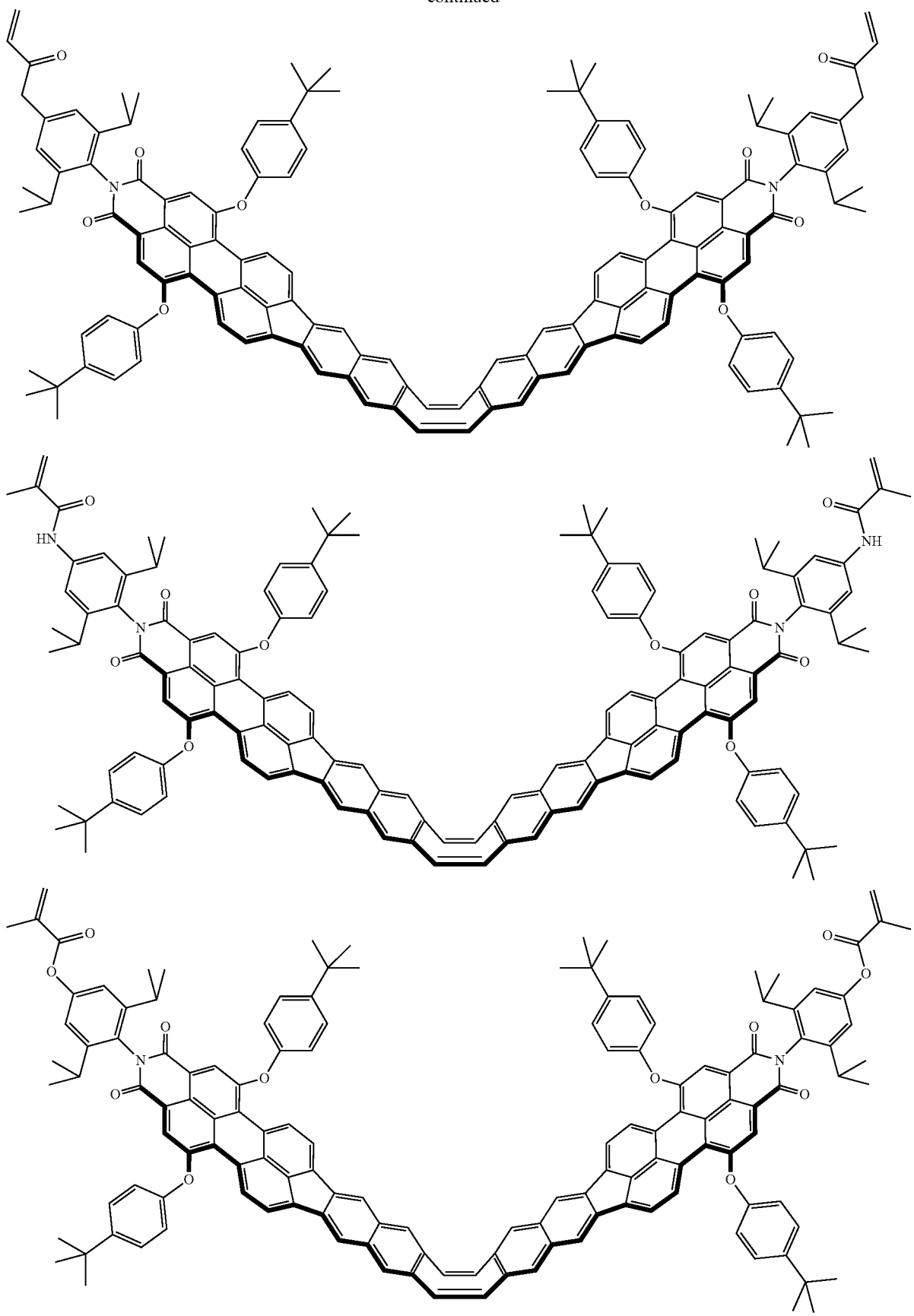

-continued
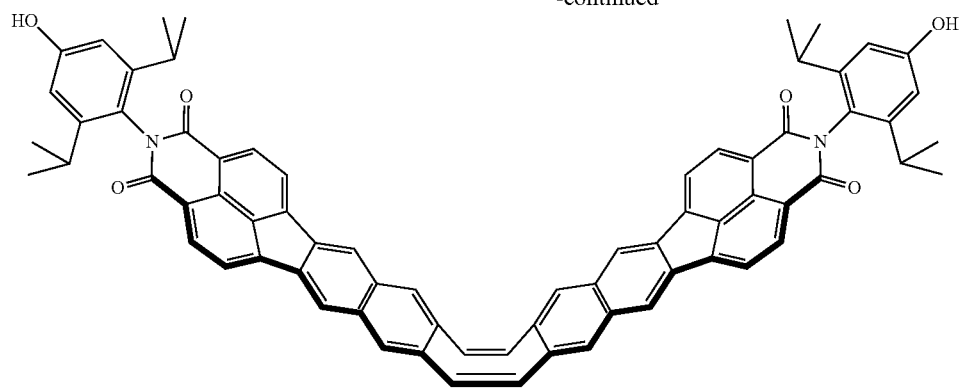
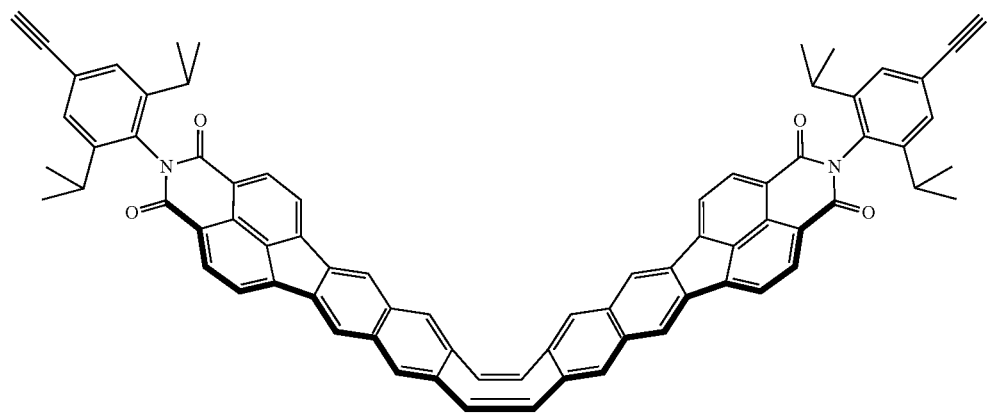
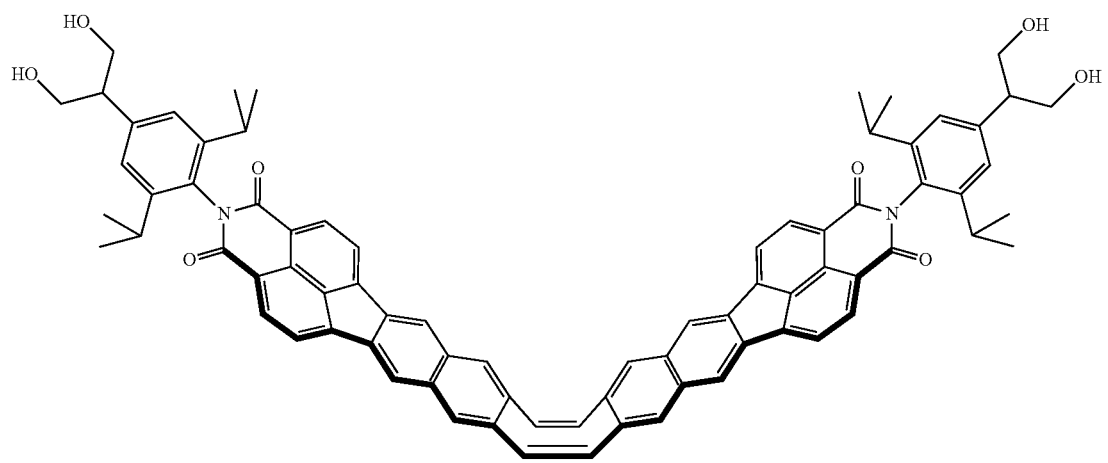
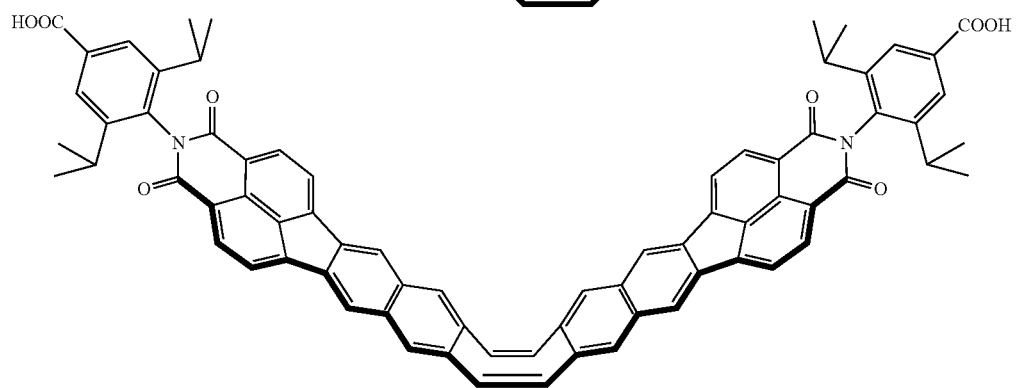

-continued
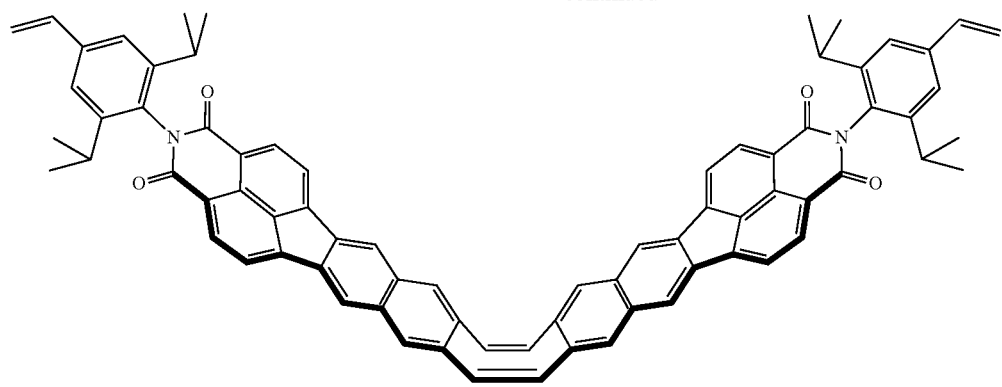
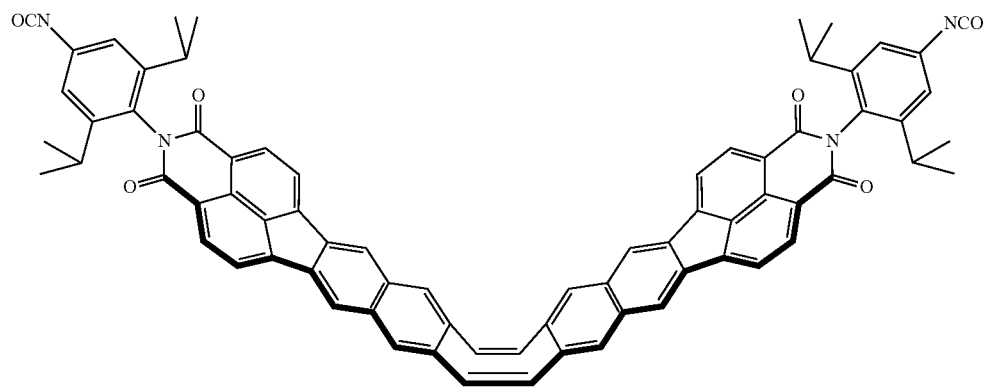
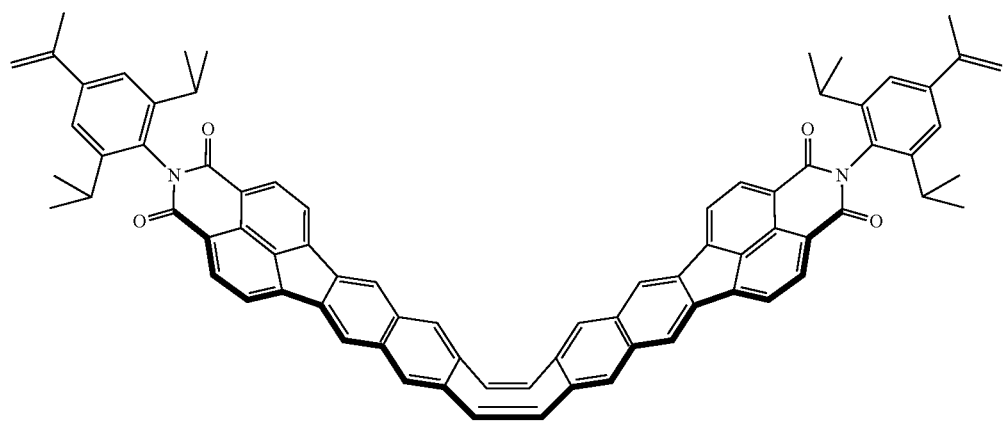
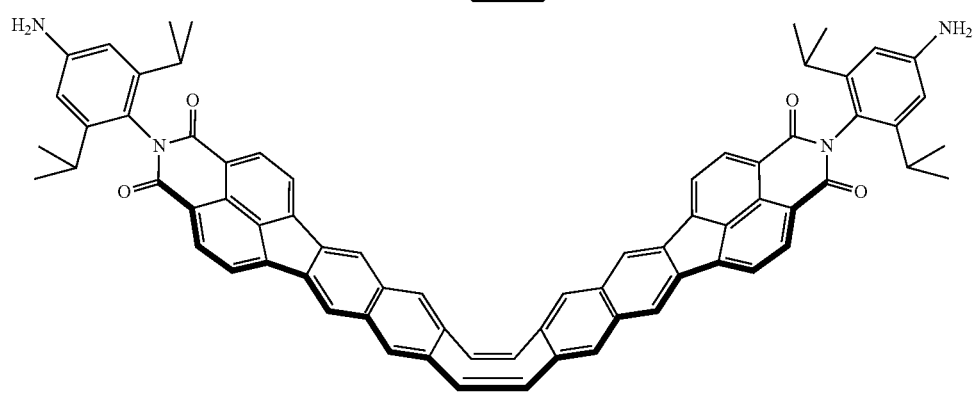

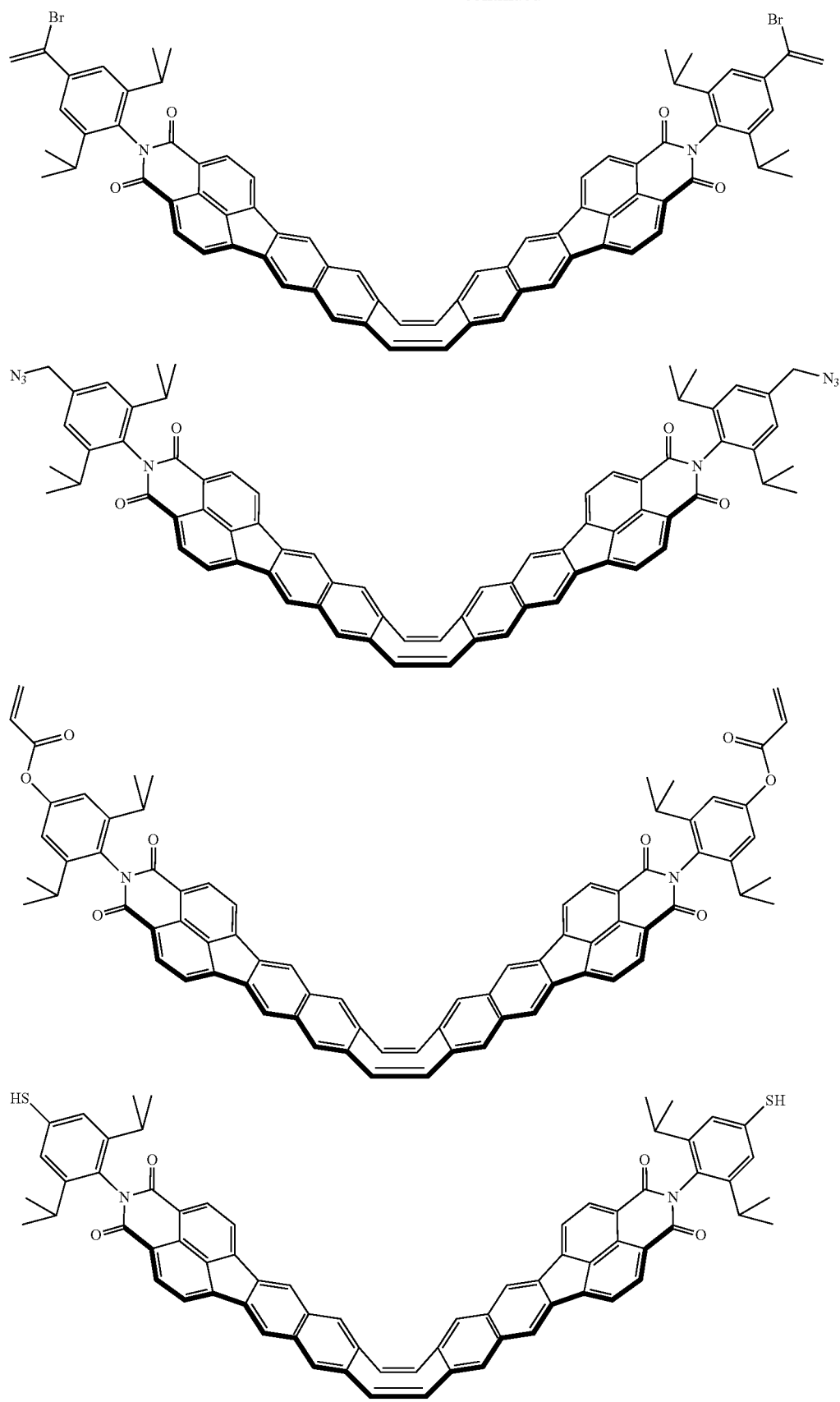

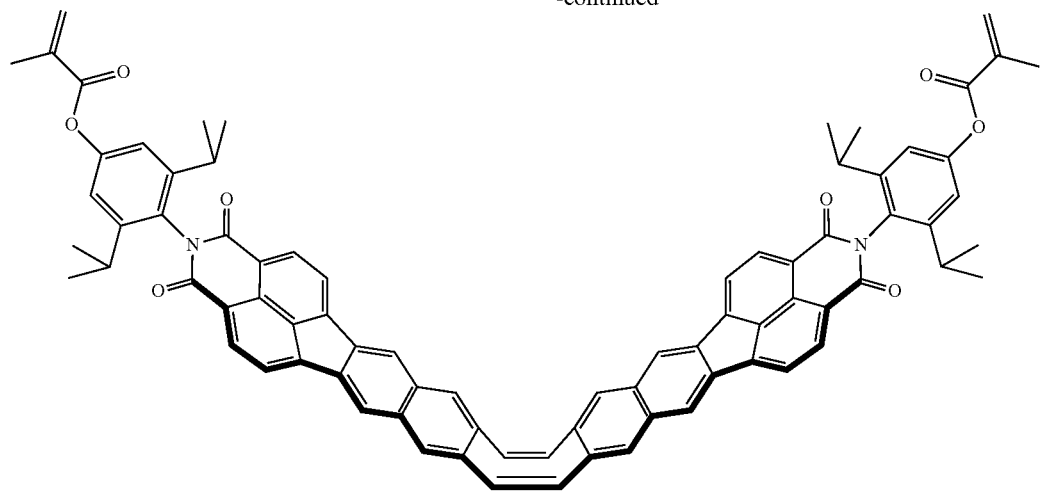
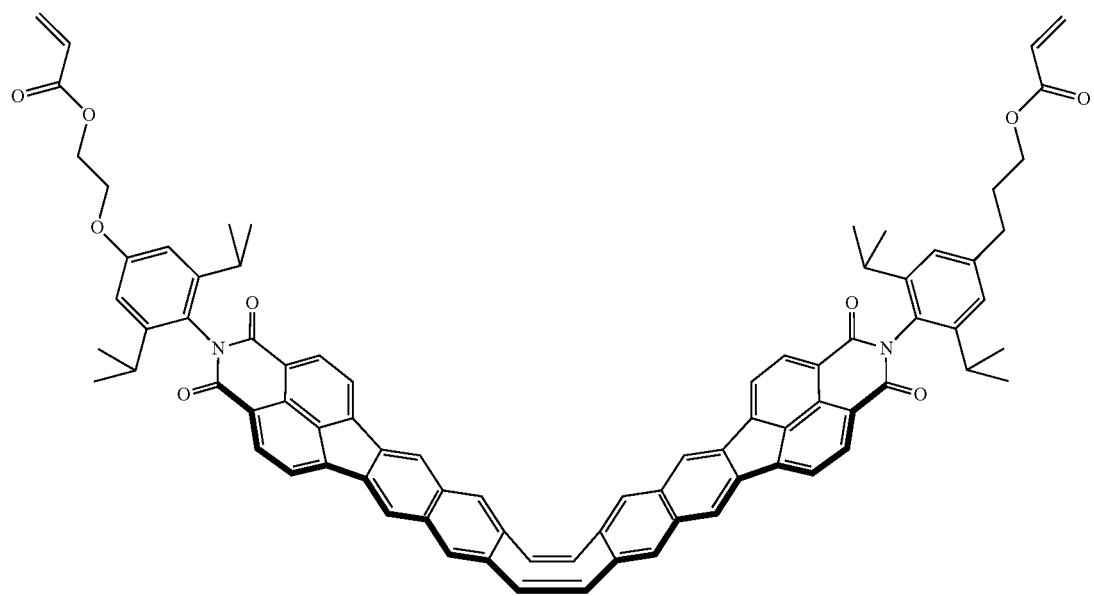
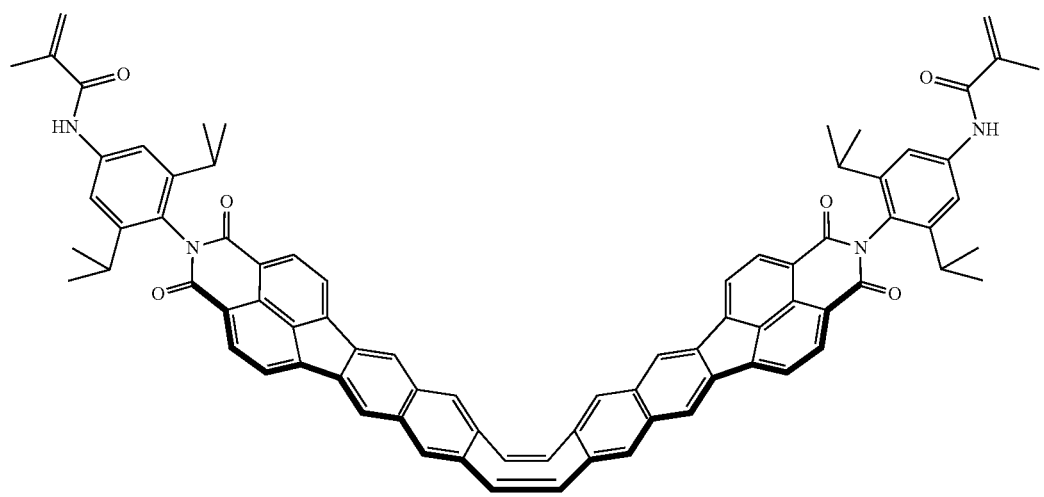

-continued
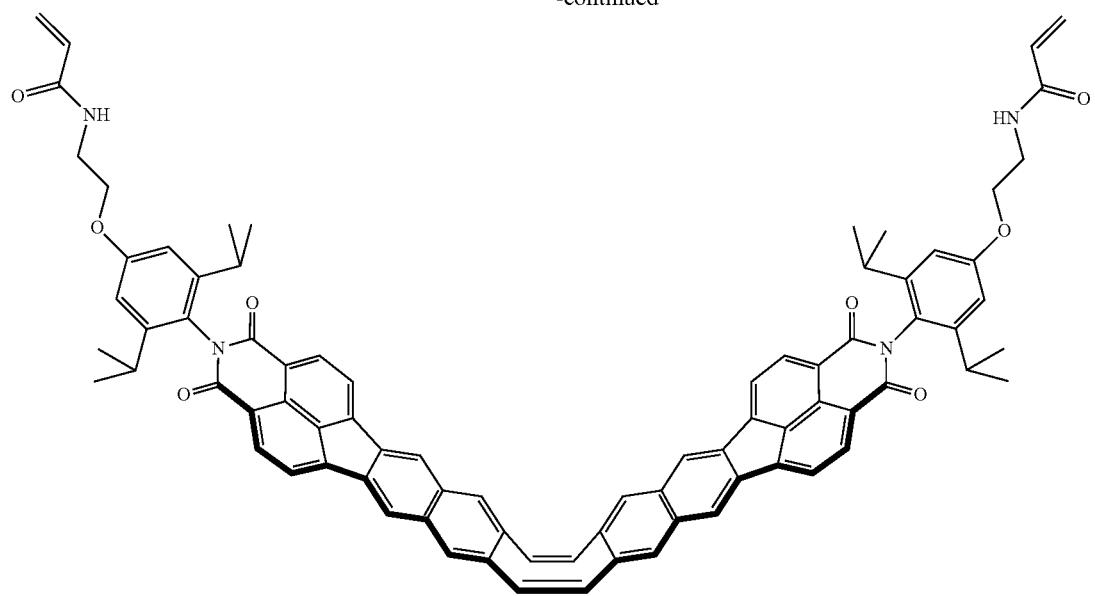
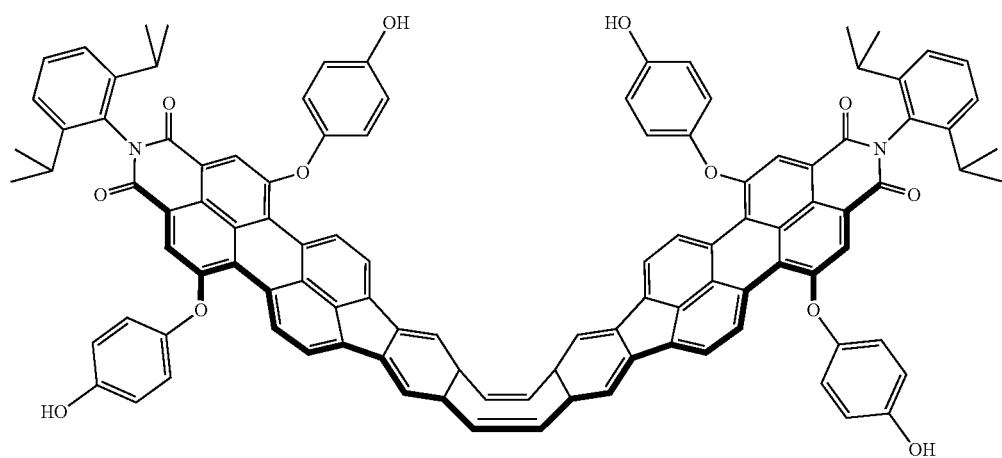
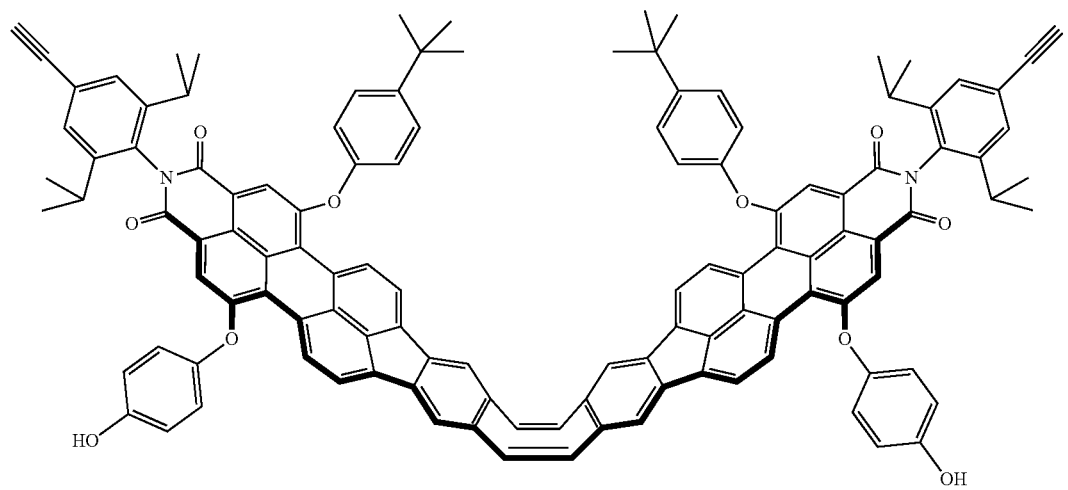

-continued
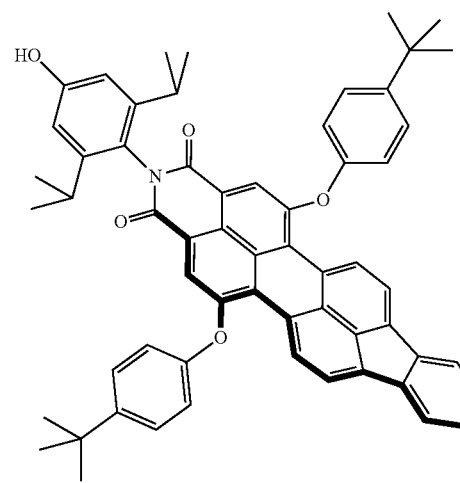
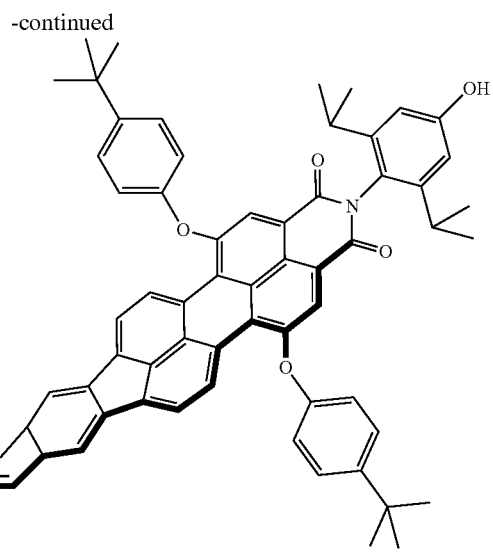
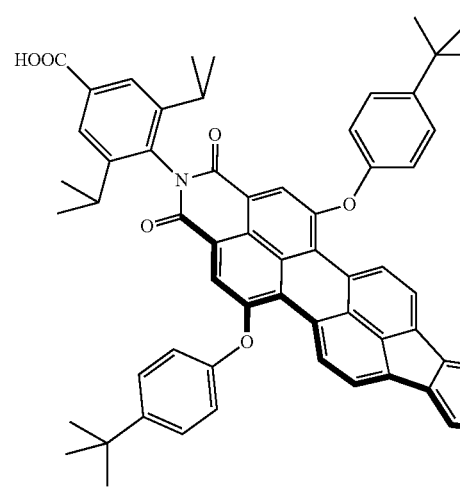
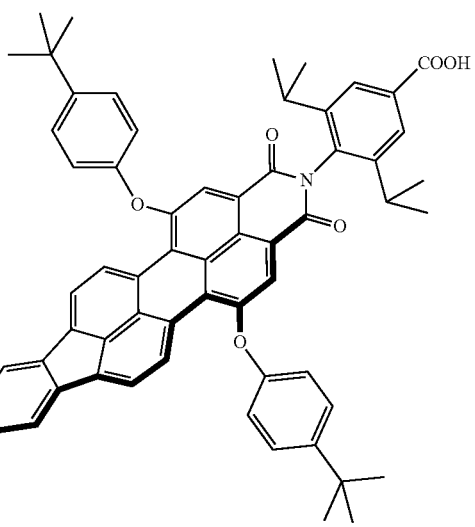
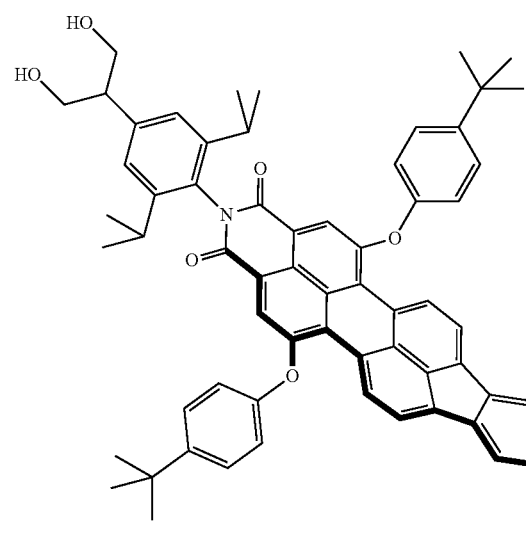
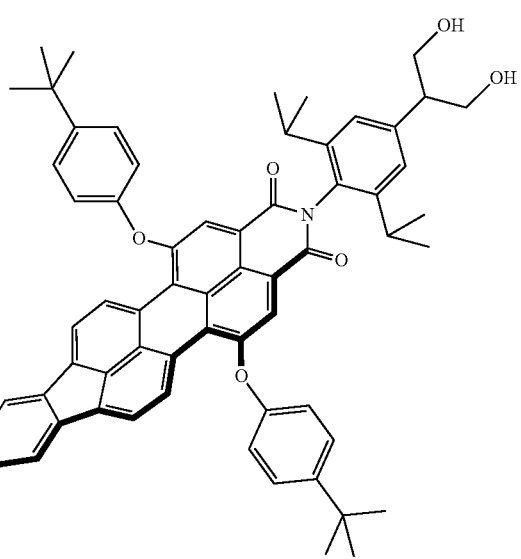

-continued
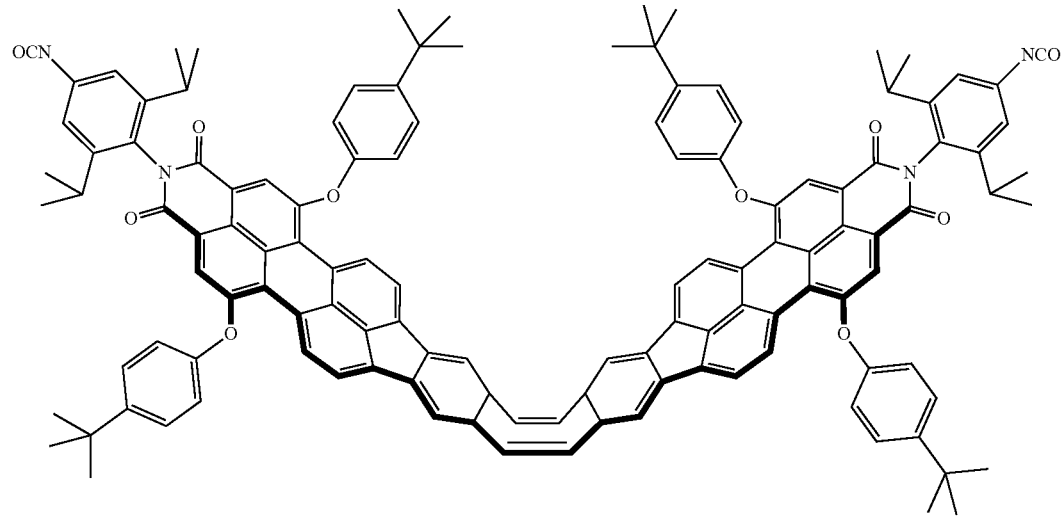
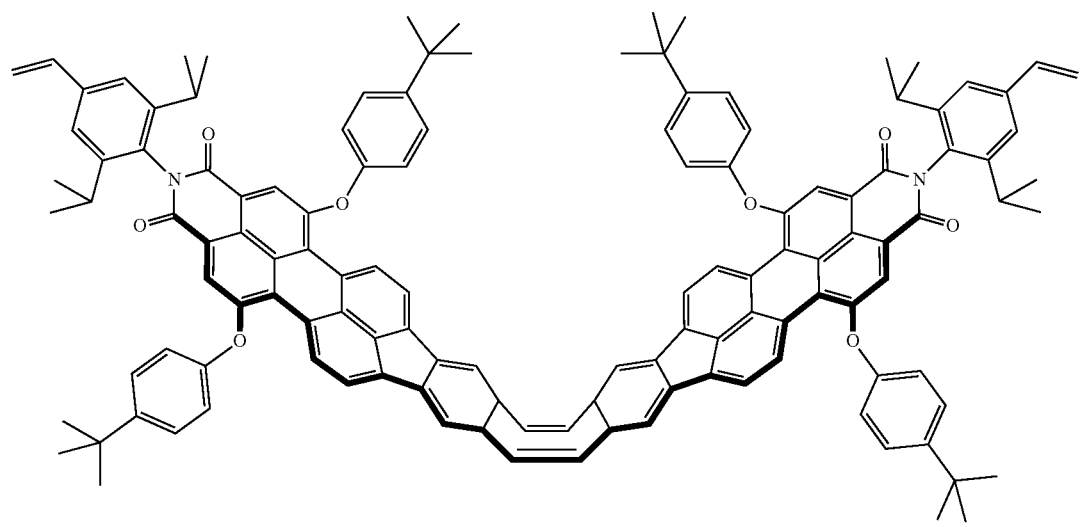
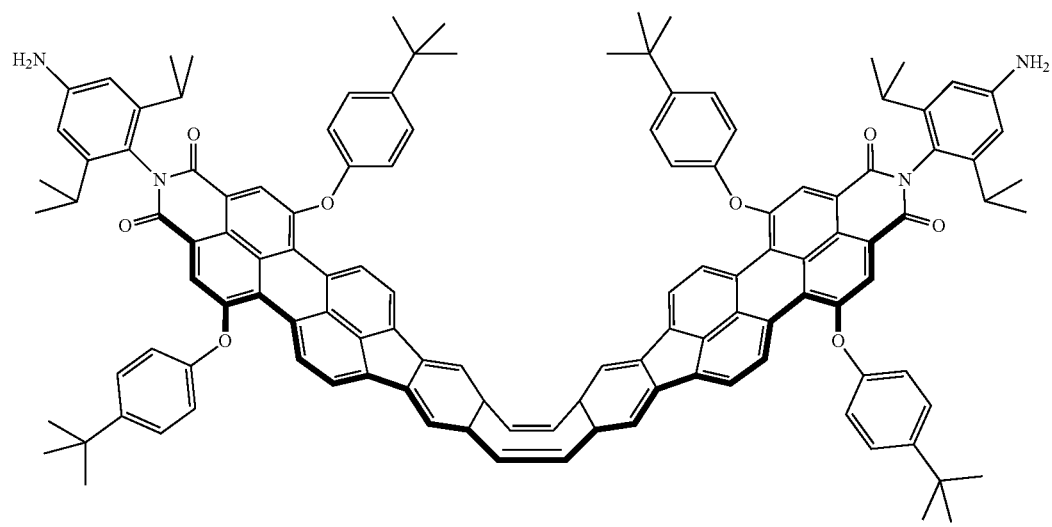

-continued
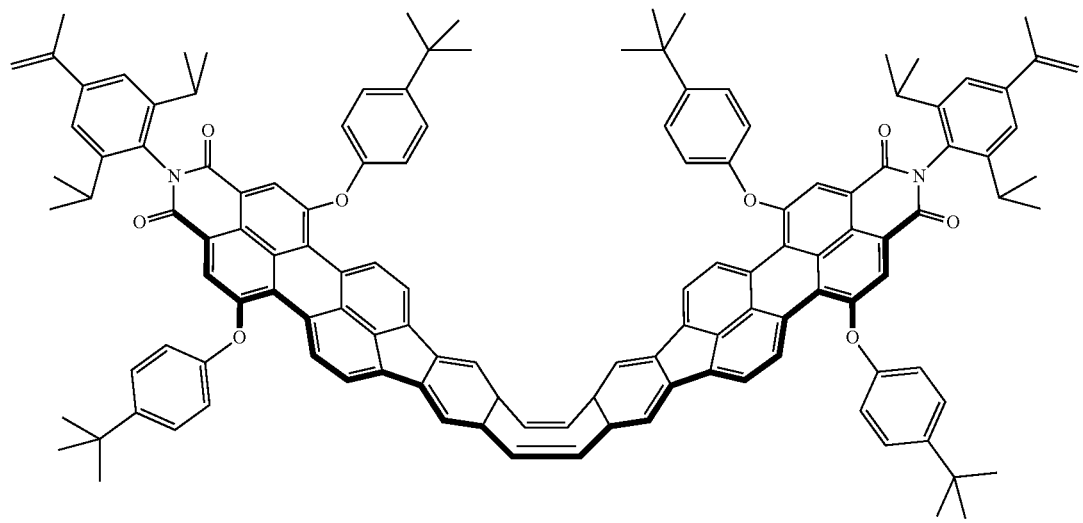
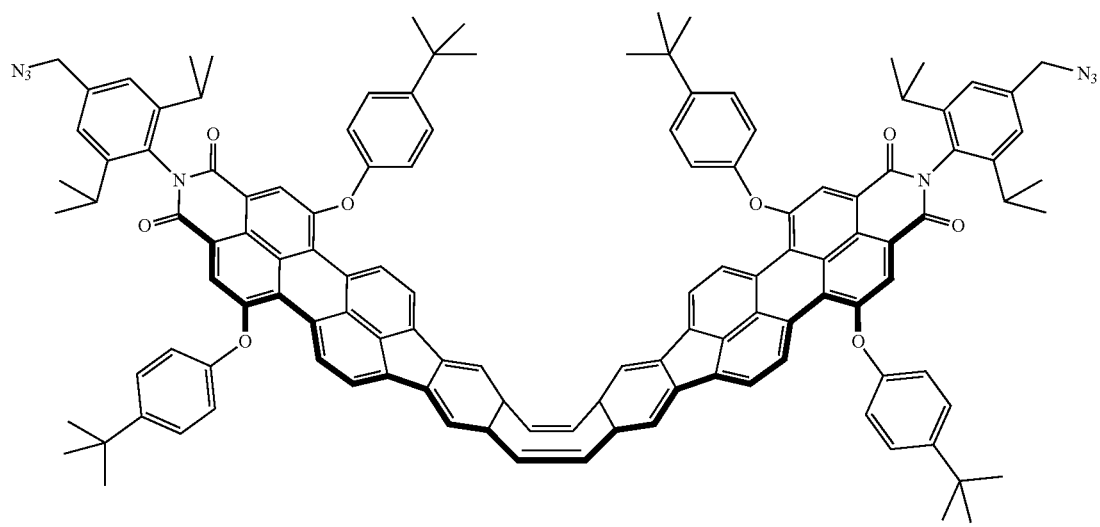
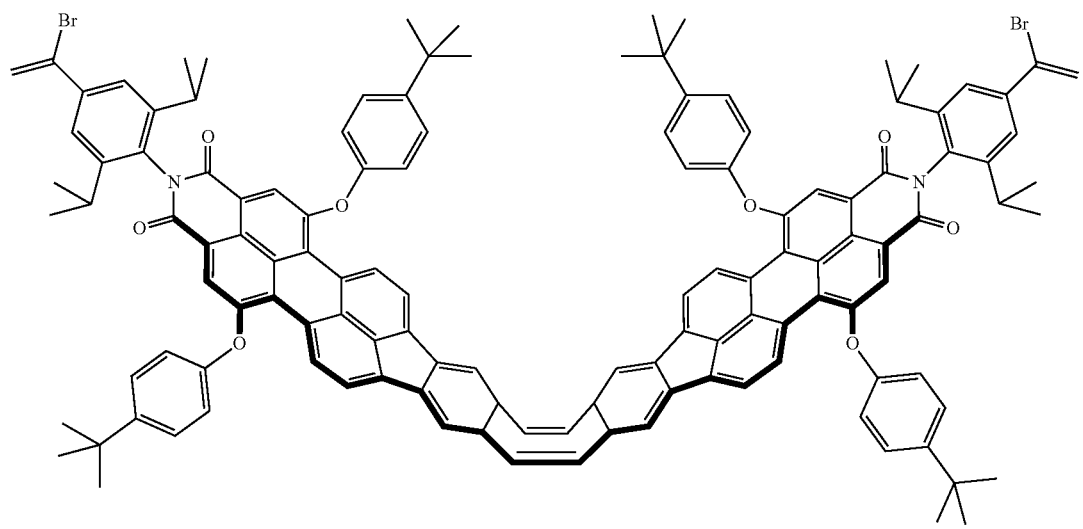

-continued
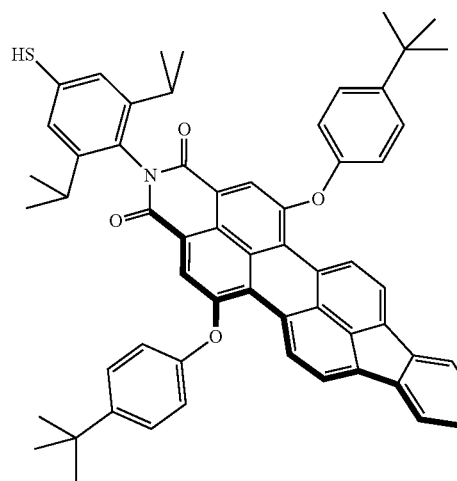 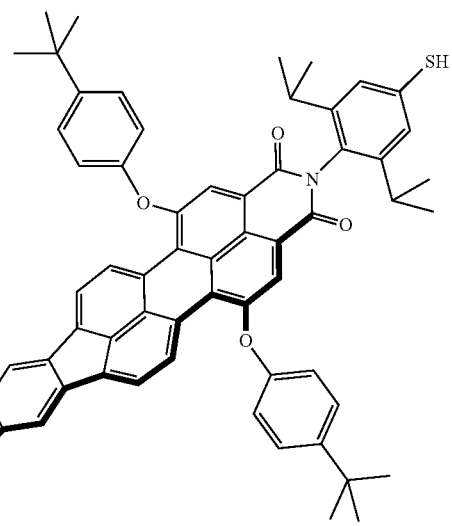
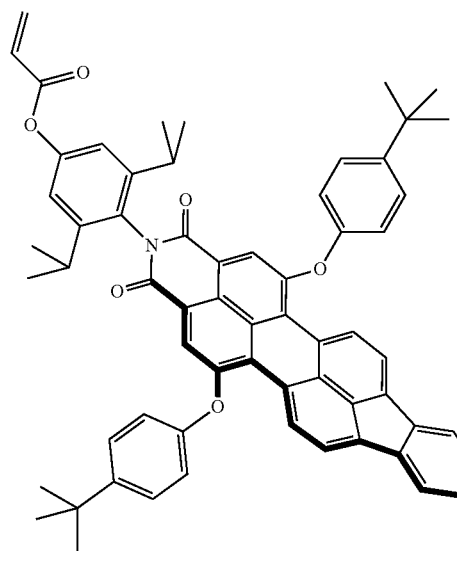 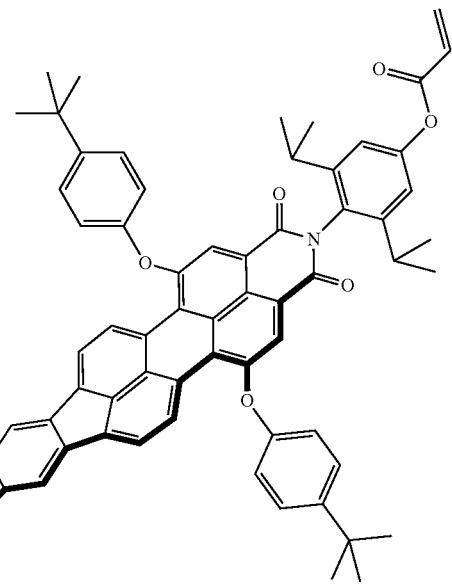
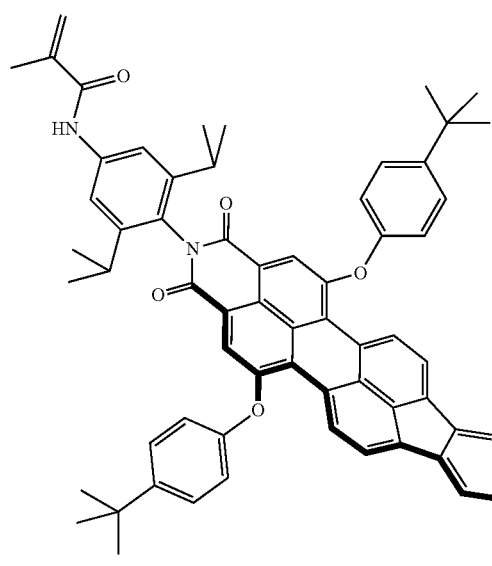 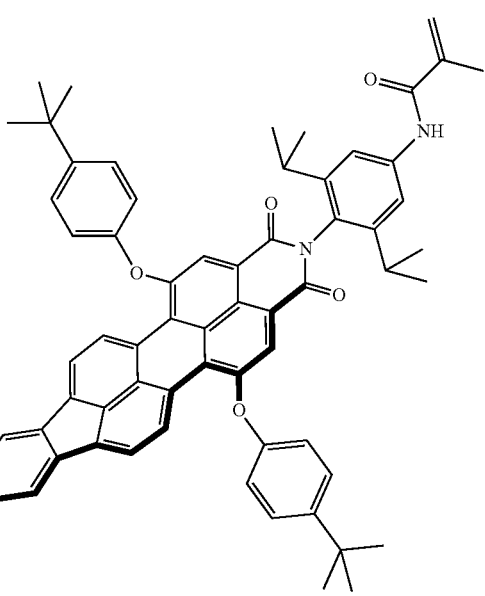

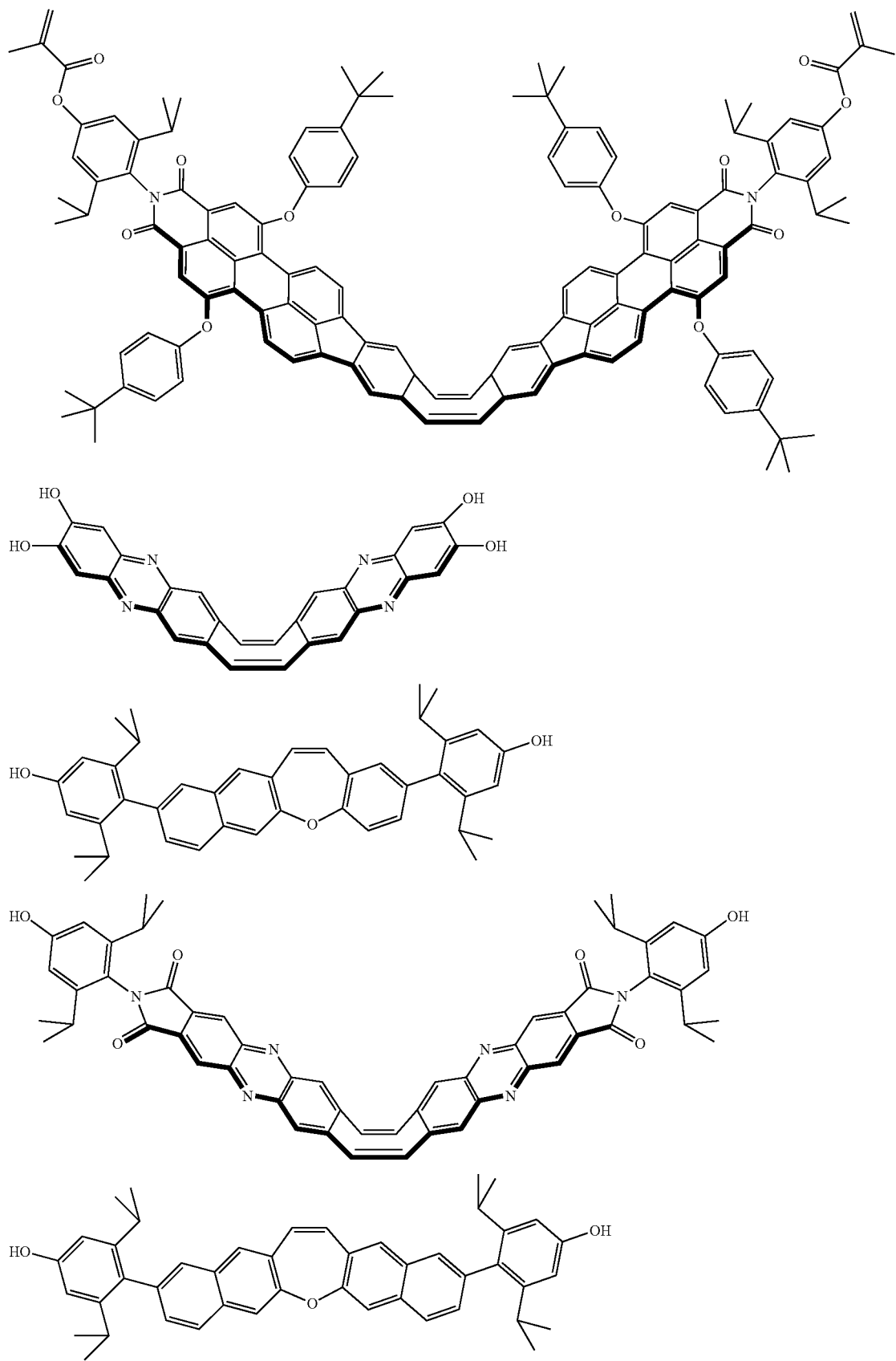

-continued
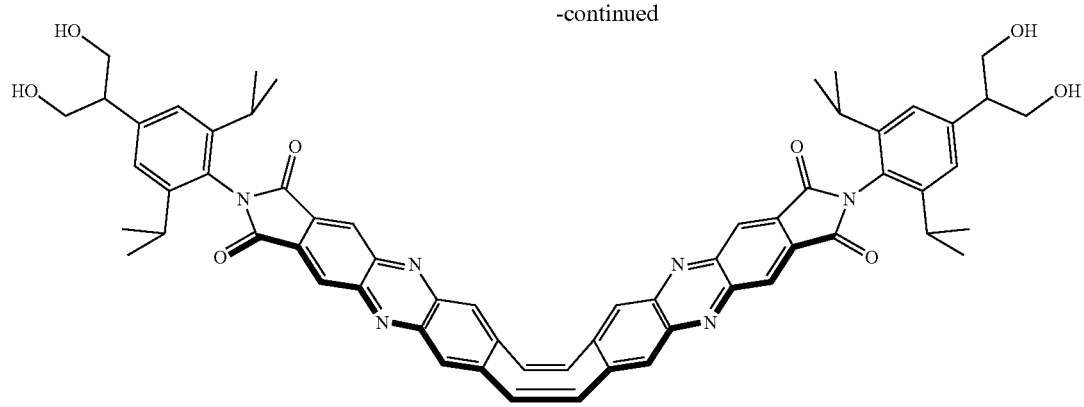
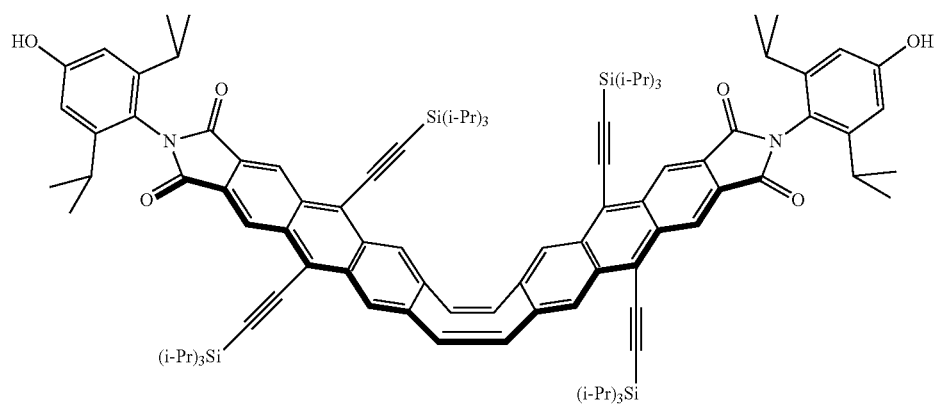
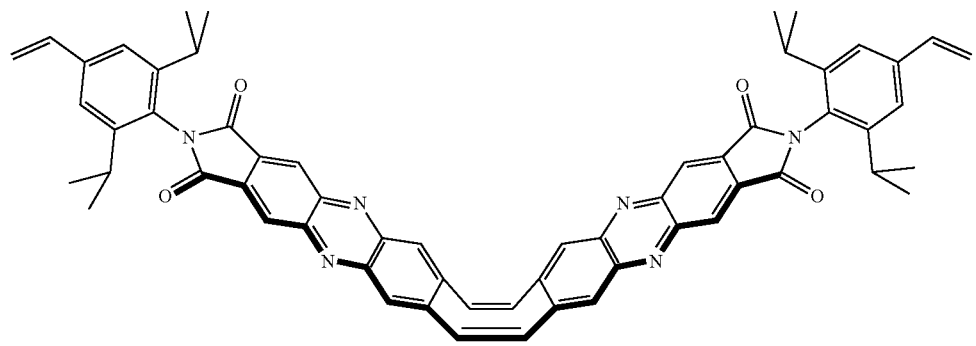
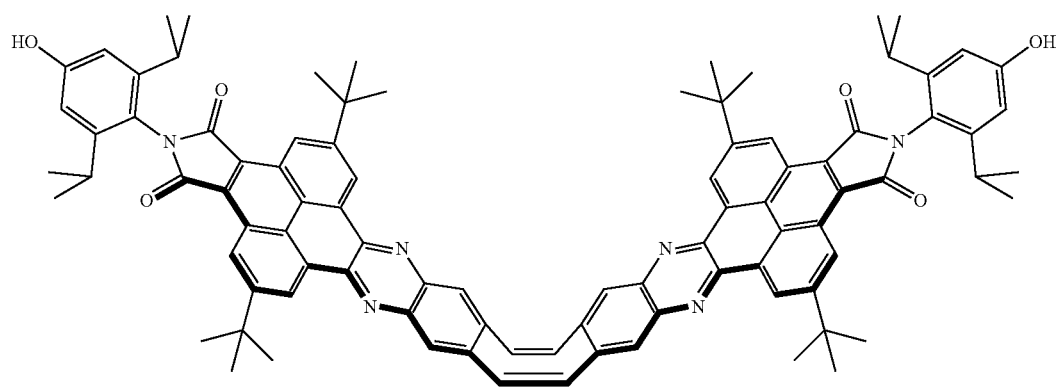

The compound (FLAP) represented by general Formula (1) can be synthesized by performing a coupling reaction using a palladium (Pd) catalyst or the like, for example, on a precursor represented by Formula (6) and a π-conjugated compound.

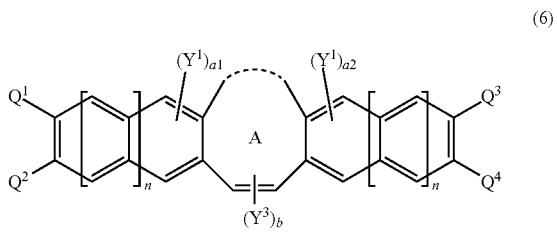

(6)

In the above general Formula (6), A, $Y^1$ to $Y^3$, a1, a2, b, m, and n are the same as those of general Formula (1).

Q1 to Q4 are halogen atoms or amino groups.

The mechanochromic light-emitting materials represented by Formulas (P1) and (P2) disclosed in Patent Literature 3 described above are synthesized by performing an acene elongation reaction on the compounds represented by the following Formulas (P3) and (P4).

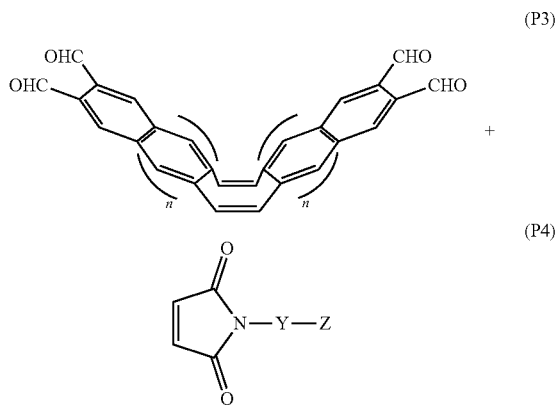

(P3)

(P4)

In the above Formula (P3), n denotes an integer of 0 to 3. In the above Formula (P4), Y denotes a substituent group that inhibits aggregation of mechanochromic light-emitting materials represented by Formulas (P1) or (P2), and Z denotes a polymerizable group. Specific examples of Y and Z are disclosed in Patent Literature 3 described above.

However, when the compound represented by Formula (P3) is used as a starting compound to synthesize mechanochromic light-emitting material, there is a problem of limited π-conjugated systems that can be synthesized because the aldehyde group of (P3) has carbon. On the other hand, the embodiment disclosed in the present specification, by using the precursor represented by Formula (6), it is possible to introduce a π-conjugated system to the positions of $Q_1$ to Q4 of Formula (6) by a coupling reaction. Therefore, the absence of carbon of aldehyde disclosed in Patent Literature 3 provides wider options of π-conjugated based compounds to be coupled to a precursor. This enables introduction of a heterocyclic structure such as a perylene ring, and a compound (FLAP) having high spatial resolution is obtained. In addition, for example, by performing a coupling reaction of a precursor with a π-conjugated based compound whose π-conjugated based structure has been slightly changed, it is also possible to synthesize a series compound (FLAP) having a different wavelength when the same stress is applied. Further, because of easy adjustment of the wavelength range for light emission, it is possible to synthesize a FLAP or the like that emit light of a wavelength out of the ultraviolet wavelength range that may adversely affect living things, for example.

The coupling reaction may be the Suzuki-Miyaura coupling that causes coupling to a π-conjugate compound having organic boron by using a Pd catalyst, the Negishi coupling that causes coupling to a π-conjugate compound having organic zinc by using a Pd catalyst, the Stille coupling that causes coupling to a π-conjugate compound having organic tin by using a Pd catalyst, the Hiyama coupling that causes coupling to a π-conjugate compound having organic silicon by using a Pd catalyst, the Sonogashira coupling that causes coupling to a π-conjugate compound having acetylene by using a Pd and Cu catalyst, the Buckwald-Hartwig coupling that causes coupling to a π-conjugate compound having an amino group by using a Pd catalyst, the Kumada-Tamao coupling that causes coupling to a π-conjugate compound having organic magnesium by using a Ni catalyst, a C—H aryl chemical reaction that causes coupling to a π-conjugate compound having no functional group by using a transition metal catalyst such as Pd, and the like, and these schemes may be used stepwise in combination.

An example of a synthesis procedure of a FLAP from the precursor represented by general Formula (6) will be described below.

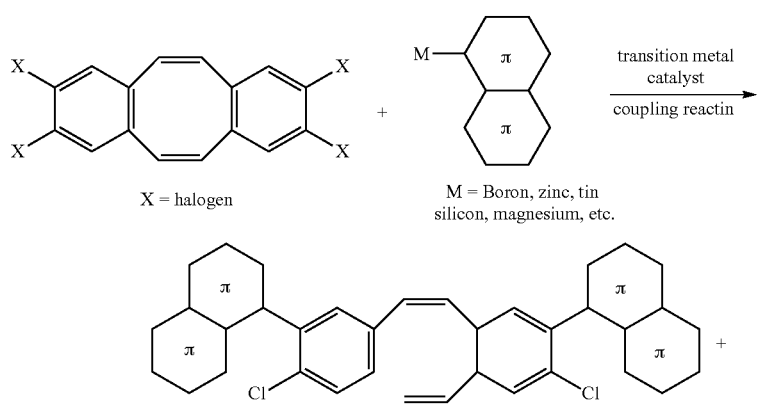

-continued

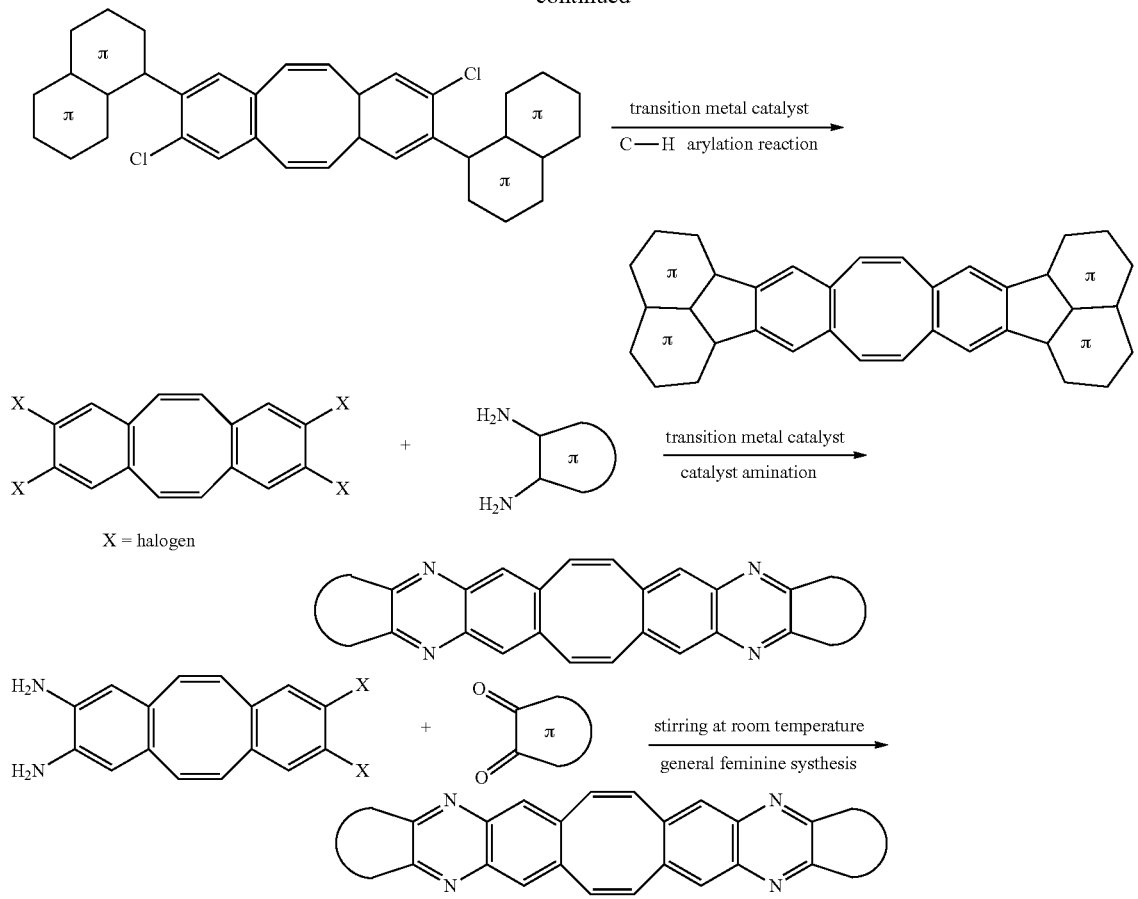

X = halogen

The embodiment of a polymer compound includes a compound (FLAP) as a polymerizable component. FIG. 2A to FIG. 4B illustrate examples of the embodiment of the polymer compound. FIG. 2A illustrates an example including a FLAP as a main chain of a polymer. The embodiment illustrated in FIG. 2A is obtained by using a FLAP in which one monofunctional polymerizable group is introduced to each of both terminals (two polymerizable groups in total), as illustrated in FIG. 2B. In the embodiment illustrated in FIG. 2A and FIG. 2B, the polymerizable group illustrated as an example in E-1 to E-11 can be used as a polymerizable group. Note that FIG. 2B illustrates an example for describing the position of the polymerizable group, and other compounds (FLAP) may be used. The same applies for FIG. 3B and FIG. 4B described later.

FIG. 3A illustrates an example including a FLAP as a cross-linkage point of a polymer. The embodiment illustrated in FIG. 3A is obtained by using a FLAP in which one bifunctional polymerizable groups is introduced to each of both terminals (four polymerizable groups in total), as illustrated in FIG. 3B. In the embodiment illustrated in FIG. 3A and FIG. 3B, the polymerizable group illustrated as an example in E-12 to E-18 can be used as a polymerizable group.

FIG. 4A illustrates another example including a FLAP as a cross-linkage point of a polymer. The embodiment illustrated in FIG. 4A is obtained by using a FLAP in which two monofunctional polymerizable groups are introduced to each of both arms (four polymerizable groups in total), as illustrated in FIG. 4B. In the embodiment illustrated in FIG. 4A and FIG. 4B, the polymerizable group illustrated as an example in E-1 to E-11 can be used as a polymerizable group.

The polymer compounds illustrated in FIG. 2A to FIG. 4A can be synthesized by mixing the FLAP illustrated in FIG. 2B to FIG. 4B, a polymerizable monomer, and a catalyst or an initiator in an organic solvent.

The polymerizable monomer forming the main chain of the polymer compound can include the FLAP illustrated in FIG. 2B to FIG. 4B and is not particularly limited as long as the FLAP can cause a conformation change when stress is applied to the main chain. For example, the polymerizable monomer may be a monomer that can cause sequential polymerization such as polyaddition or polycondensation, radical polymerization, ring-opening polymerization, or click reaction.

The monomer that can cause polyaddition (for example, polyurethane synthesis) and polycondensation may be a monomer containing the polymerizable group illustrated in the above Formulas (E-1) to (E-7) as examples. Further, as the monomer that can cause click reaction, a polymerizable monomer having azide can be used when the monomer of Formula (E-8) is used as the polymerizable groups ($E^1$ to $E^3$) of the FLAP described in general Formula (1), as described above. Similarly, a polymerizable monomer having alkyne can be used when the monomer of Formula (E-9) is used as the polymerizable groups ($E^1$ to $E^3$), a polymerizable monomer having vinyl can be used when the monomer of Formula (E-10) is used as the polymerizable groups ($E^1$ to $E^3$), and a polymerizable monomer having thiol can be used when the monomer of Formula (E-11) is used as the polymerizable groups ($E^1$ to $E^3$).

The monomer that can cause ring-opening polymerization may be norbornene, acetyl norbornene, ethylene oxide, propylene oxide, ethyleneimine, trimethylene oxide, tetrahydrofuran, β-propiolactone, γ-butyrolactone, ε-caprolactone, or the like.

The monomer that can cause radical polymerization may be an ethylene; a vinyl aromatic monomer, for example, styrene, α-methylstyrene, o-chlorostyrene or vinyl toluene; an ester of vinyl alcohol and monocarboxylic acid having 1-18 carbon atoms, for example, vinyl acetate, vinyl propionate, vinyl-n-butyrate, vinyl laurate, and vinyl stearate; advantageously, an ester of α,β-monoethylene unsaturated monocarboxylic or dicarboxylic acid having 3-6 carbon atoms (particularly, acrylic acid, methacrylic acid, maleic acid, fumaric acid, and itaconic acid) and alkanol having generally 1-12, advantageously 1-8, and particularly 1-4 carbon atoms, for example, particularly, methyl acrylate, methyl methacrylate, ethyl acrylate, ethyl methacrylate, n-butyl acrylate, n-butyl methacrylate, isobutyl acrylate, isobutyl methacrylate, 2-ethylhexyl acrylate, 2-ethylhexyl methacrylate, dimethyl maleate, di-n-butyl maleate, nitrile of α,β-monoethylene unsaturated carboxylic acid such as acrylonitrile, and a C4-C8 conjugated diene such as 1,3-butadiene and isoprene; or the like.

In synthesis, the above monomer may be used alone, or two or more types of monomers may be used to form a random copolymer.

The catalyst or the initiator is not particularly limited as long as a polymer compound can be synthesized from a polymerizable monomer and a compound (FLAP). For example, the catalyst may be Grubb's catalyst, Hoveyda-Grubb's catalyst, Ru complex, tungsten chloride, tetramethyltin, or the like. Further, the initiator may be azobis isobutyronitrile, benzoyl peroxide, di-tert-butyl peroxide, hydrogen peroxide-iron (II) salt, persulphate-sodium hydrogen sulfite, triethyl borane, or the like.

With respect to the main chain, the above polymerizable monomer can be suitably selected so as to have a desired resin characteristic. For example, when a hard polymer (high Tg, high yield stress, small elongation) is intended to be synthesized, a polymerizable monomer whose main chain is polystyrene, polymethyl methacrylate, or the like can be used. Further, when a soft polymer (low Tg, low yield stress, large elongation) is intended to be synthesized, a polymerizable monomer whose main chain is polyurethane, polybutadiene, polyacetyl norbornene, polydimethylsiloxane, or the like can be used.

The compound illustrated in the embodiment can be used for a viscosity probe by using the same method as illustrated in Patent Literature 2, for example.

While the present invention will be specifically described below with examples, these examples are solely provided for reference of specific aspects. These examples are neither to limit the scope of the invention disclosed by this application nor to imply such limitation.

EXAMPLES

In the following examples, purchased reagents were used without change unless otherwise specified.

Wakogel, C-300 or C-400 (by Wako Pure Chemical Co.) was used for silica gel column chromatography.

$^1$H and $^{13}$C NMR spectrum measurement was used for structural determination of a resultant compound.

($^1$H and $^{13}$C NMR Spectrum Measurement)
Equipment: ECA-600 by JOEL Ltd.
Measured frequency: 600 MHz at $^1$H-NMR measurement, 151
MHz at $^{13}$C-NMR measurement
Internal reference: $CDCl_3$ Molecular weights were measured by mass spectrometry based on high-resolution atmospheric pressure chemical ionization (APCI).

(Mass Spectrometry)
Equipment: micro TOF Time-of-flight mass spectrometer by BRUKER Further, various optical analysis was performed under the following conditions.

(Ultraviolet and Visible Absorption Spectrum Measurement)
Equipment: Shimadzu, UV-3600 and UV-2550 by Shimadzu Corporation (Ultraviolet and Visible Fluorescence Spectrum Measurement)
Equipment: Shimadzu, RF5300PC by Shimadzu Corporation (Absolute Fluorescence Quantum Yield Measurement)
Equipment: HAMAMATSU, C9920-02S by Hamamatsu Photonics K. K.

(Single-Molecule Fluorescence Imaging)
Equipment: inverted microscope IX71 by Olympus Corporation, imaging spectrometer for microscope Connection CLP-50 by Bunkoukeiki Co., Ltd., and electron multiplying CCD camera iXon by Andor Technology, Inc. (used in combination of three items)

[Synthesis 1 of Precursor]

A compound (b) was synthesized along the following synthesis route.

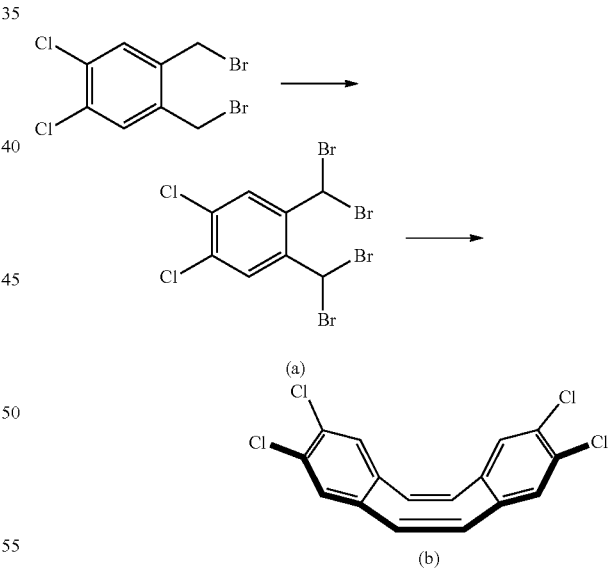

Synthesis of
1,2-bis(dibromomethyl)-4,5-dichlorobenzene
(Compound (a))

1,2-bis(bromomethyl)-4,5-dichlorobenzene (synthesized in accordance with a method described in Synthetic communication, 1983, 13, p 639-648, 5.0 g, 15 mmol), N-bromosuccinimide (8.0 g, 45 mmol), and azobis isobutyronitrile (20 mg, 0.08 mmol) were dissolved in benzotrifluoride (100 mL) in a UV irradiation reaction vessel. This solution was stirred under UV irradiation by using a high-pressure mercury lamp at 100 degrees Celsius for 7 hours under $N_2$ atmosphere. Subsequently, after this solution was cooled to room temperature, the mixture was filtered to distill the solvent. After purification by column chromatography using hexane, a compound (a) was obtained as a white solid (3.9 g, yield 53%). The spectrum data of the compound (a) was as follows.

$^1$H NMR (CDCl$_3$, 600 MHZ): δ 7.78 (br, 2H), 6.99 (br, 2H): $^{13}$C NMR (CDCl$_3$, 150 MHz): δ 137.32 (br), 134.78, 131.45 (br), 33.96: APCI-HRMS: m/z 406.7249 ([M−Br]$^+$, C$_5$H$_4$Br$_3$Cl$_2$ requires: 406.7235).

Synthesis of 2,3,8,9-tetrachlorodibenzo[a,e]cyclooctatetraene (Compound (b))

1,2-bis(dibromomethyl)-4,5-dichlorobenzene (0.85 g, 1.7 mmol) and NaI (1.6 g, 10 mmol) were dissolved in anhydrous dimethylformamide (10 mL). This solution was heated and refluxed and then stirred for 4.5 hours under $N_2$ atmosphere. Subsequently, after this solution was cooled to room temperature, a compound (b) was obtained as a white solid (64 mg, yield 22%) by column chromatography using hexane. The spectrum data of the compound (b) was as follows.

$^1$H NMR (CDCl$_3$/C$_6$D$_6$ (1%), 600 MHZ): δ 7.18 (s, 4H), 6.70 (s, 4H); $^{13}$C NMR (CDCl$_3$/C$_6$D$_6$ (1%), 150 MHz): δ 136.53, 132.60, 131.53, 130.70; APCI-HRMS: m/z 339.9375 ([M]$^+$, C$_{16}$H$_8$Cl$_4$ requires: 339.9380).

[Synthesis 2 of Precursor]

A compound (f) was synthesized along the following synthesis route.

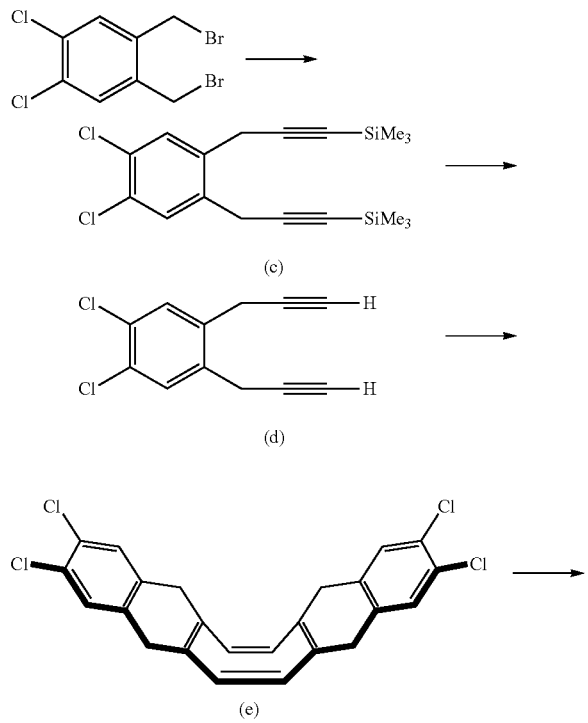

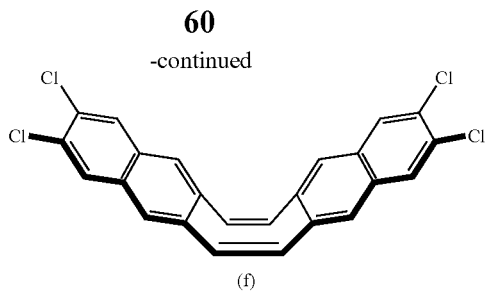

(f)

Synthesis of 1,2-bis(trimethylsilylpropyl)-4,5-dichlorobenzene (Compound (c))

All the procedures described below were performed under $N_2$ atmosphere.

Trimethylsilylacetylene (15 mL, 110 mmol) was dissolved in THF (60 mL), which was cooled in an ice water bath. Next, a tetrahydrofuran (THF) solution of isopropyl magnesium chloride (2 M, 54 mL, 110 mmol) was slowly added to the above solution, and after completion of the addition, the mixture was stirred at room temperature for 1 hour. Copper bromide (I) (2.8 g, 19 mmol) was then added, and this mixture was stirred for another 30 minutes. Furthermore, 1,2-bis(bromomethyl)-4,5-dichlorobenzene (7.1 g, 21 mmol) was added, and the mixture was heated and refluxed for 4.5 hours. Then, after cooled to room temperature, the mixture was poured into a saturated ammonium chloride aqueous solution (800 mL), and the product was extracted with hexane. A compound (c) was obtained as white powder (4.3 g, yield 55%) by column chromatography (hexane/ethyl acetate, 100/0.5, v/v). The spectrum data of the compound (c) was as follows.

$^1$H NMR (CDCl$_3$, 600 MHZ): δ 7.54 (s, 2H), 3.56 (s, 4H), 0.19 (s, 18H): $^{13}$C NMR (CDCl$_3$, 150 MHz): δ 134.49, 131.08, 130.66, 102.02, 88.84, 23.44, 0.12: APCI-HRMS: m/z 367.0883 ([M+H]$^+$, C$_{18}$H$_{28}$Cl$_2$Si$_2$ requires: 367.0866).

Synthesis of 1,2-dipropynyl-4,5-dichlorobenzene (Compound (d))

1,2-bis(trimethylsilylpropynyl)-4,5-dichlorobenzene (210 mg, 0.57 mmol) synthesized as described above and silver nitrate (0.97 g, 5.7 mmol) were added to a mixture solution of dichloromethane (10 mL), water (1.4 mL), and acetone (1 mL). This mixture solution was vigorously stirred at room temperature for 1 hour, and 35 mass % of concentrated hydrochloric acid was gently added to the suspension. This mixture was stirred for another 1 hour and filtered. The organic phase was washed with a saturated saline solution, passed through an anhydrous sodium sulfate pad, and then passed through a celite pad. A compound (d) was obtained as a colorless solid (128 mg, yield 100%). The spectrum data of the compound (d) was as follows.

$^1$H NMR (CDCl$_3$, 600 MHZ): δ 7.57 (s, 2H), 3.55 (d, J=2.8 Hz, 4H), 2.25 (t, J=2.8 Hz, 2H); $^{13}$C NMR (CDCl$_3$, 150 MHz): δ 134.14, 131.38, 130.65, 79.82, 72.21, 22.07; APCI-HRMS: m/z 223.0069 ([M+H]$^+$, C$_{12}$H$_9$Cl$_2$ requires: 223.0076).

<Synthesis of Compound (e)>

Next, the compound (d) (130 mg, 0.57 mmol) synthesized by the method described above, NiBr$_2$ (DME) (43 mg, 0.14 mmol), activated zinc powder (17 mg, 0.28 mmol), and water (2.4 μL, 0.14 mmol) were dissolved in THE (2.5 mL) in a Schlenk. The above mixture was frozen and deaired, the Schlenk was then sealed under $N_2$ atmosphere, and the mixture was heated at 60 degrees Celsius for 1 hour while being stirred. The mixture was then cooled to room temperature and filtered with celite. The solvent was distilled, and a compound (e) was obtained as light yellow powder (120 mg, yield 94%). The spectrum data of the compound (e) was as follows.

$^1$H NMR (CDCl$_3$, 600 MHZ): δ 7.20 (s, br, 4H), 5.83 (s, br, 4H), 3.25 (s, br, 8H); $^{13}$C NMR (CDCl$_3$, 150 MHz): δ 134.30, 133.01, 131.50, 129.76, 129.46, 34.36: APCI-HRMS: m/z 445.0088 ([M+H]$^+$, C$_{24}$H$_{17}$Cl$_4$ requires: 445.0079).

<Synthesis of Compound (f)>

The compound (e) (120 mg, 0.27 mmol) obtained by the method described above and 2,3-Dichloro-5,6-dicyano-1,4-benzoquinone (Tokyo Chemical Industry Co., Ltd., 134 mg, 0.59 mmol) were dissolved in toluene (3.5 mL), which was stirred at room temperature for 1 hour. The obtained mixture was filtered, silica gel was added to the filtrate to distill the solvent, and thereby the residue was adsorbed in the silica gel. The silica gel to which a compound (f) was absorbed was used to perform purification by silica gel column chromatography (hexane and then dichloromethane), and the compound (f) was obtained as white powder (26 mg, yield 22%). The spectrum data of the compound (f) was as follows.

$^1$H NMR (CDCl$_3$, 600 MHz): δ 7.79 (s, 4H), 7.48 (s, 4H), 7.03 (s, 4H); $^{13}$C NMR (CDCl$_3$, 150 MHz): δ 136.10, 133.24, 131.30, 130.47, 128.47, 126.94: APCI-HRMS: m/z 440.9763 ([M+H]$^+$, C$_{24}$H$_{13}$Cl$_4$ requires: 440.9766).

[Synthesis 1 of FLAP Precursor]

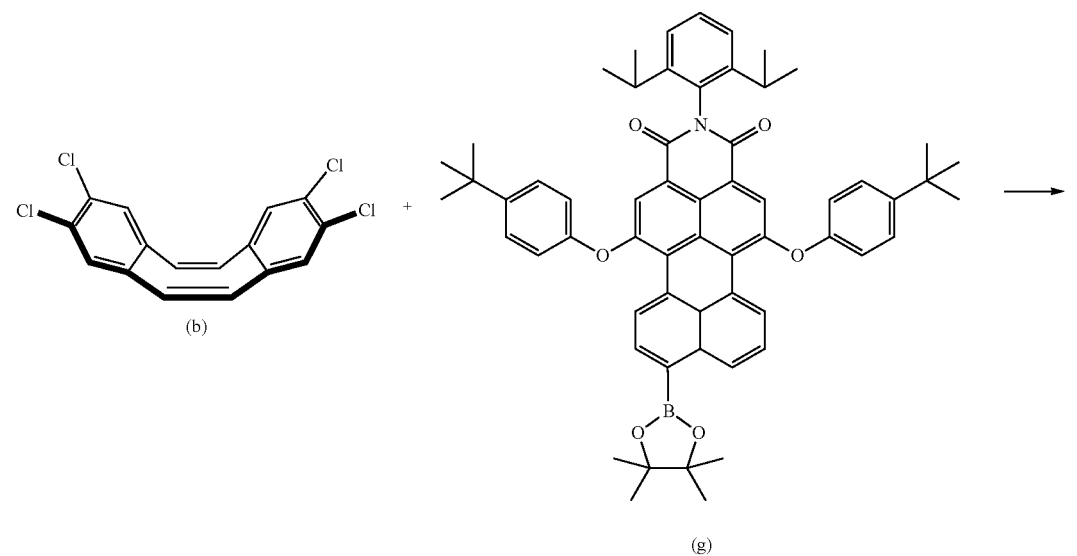

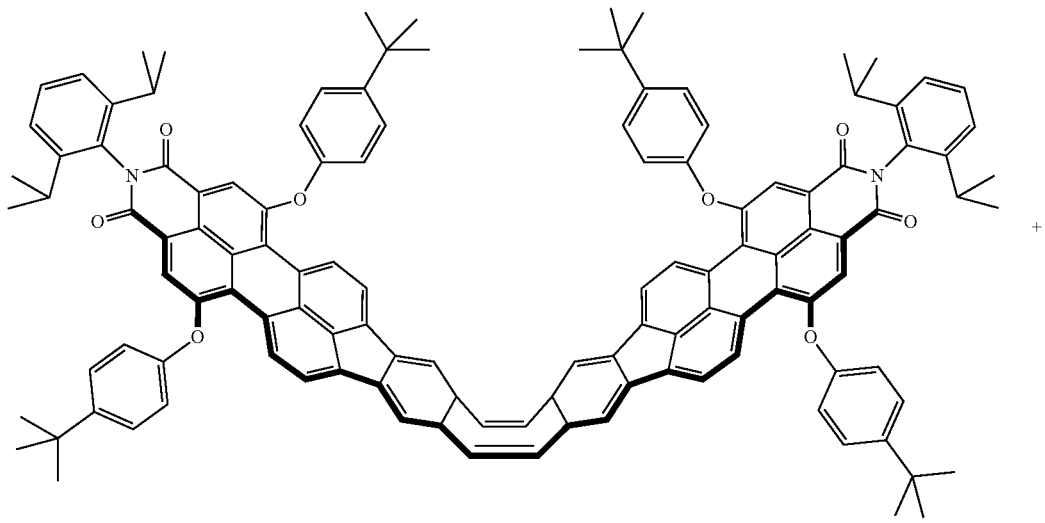

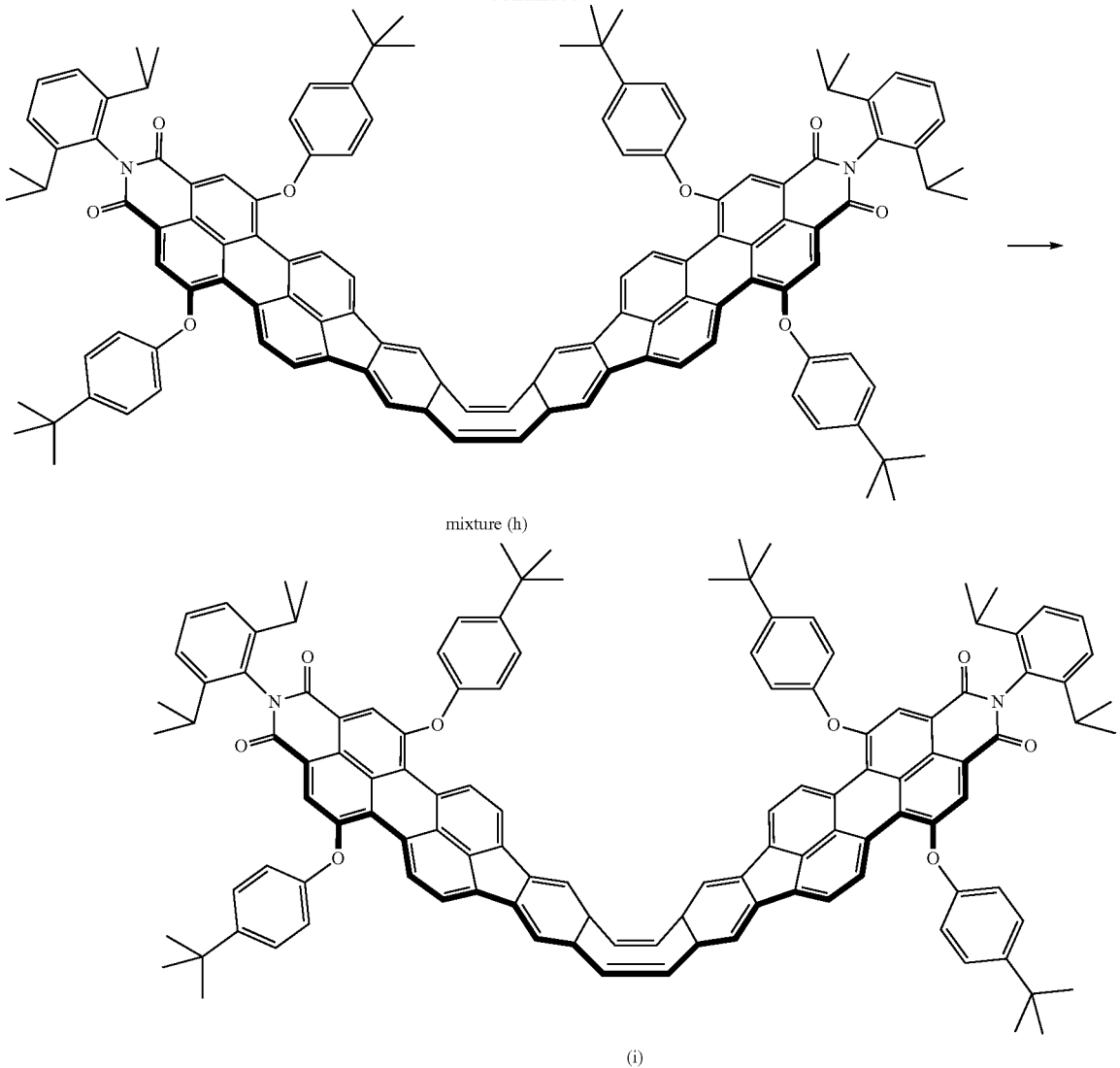

mixture (h)

(i)

A mixture of 9-(4,4,5,5-tetramethyl-1,3,2-dioxaborolanyl)-N-(2,6-diisopropylphenyl)-1,6-bis(4-tert-butylphenoxy) perylene-3,4-dicarboxymide (compound (g); synthesized by a method described in New Journal of Chemistry, 2016, 40, p 8032-8052, 200 mg, 0.22 mmol), the compound (b) synthesized in the section of [Synthesis 1 of precursor] (34 mg, 0.10 mmol), palladium (II) acetate (Pd(OAc)$_2$) (2.3 mg, 10 μmol), 2-cyclohexylphosphino-2',4',6'-triisopropyl biphenyl (XPhos; 9.5 mg, 20 μmol), tripotassium phosphate (K$_3$PO$_4$; 110 mg, 0.50 mmol), and water (30 μL) was dissolved in THF (5 mL) in a Schlenk.

The obtained mixture was frozen and deaired, the Schlenk was then sealed under N$_2$ atmosphere, and the mixture was heated at 60 degrees Celsius overnight while being stirred. The mixture was then cooled to room temperature, the solvent was evaporated, and an isomeric mixture (h) was obtained as a red solid (62 mg, yield 34%) by column chromatography (hexane/dichloromethane, 1/1, v/v). The spectrum data of the above (h) was as follows.

$^1$H NMR (CDCl$_3$, 600 MHZ): δ 9.38-9.36 (m, 4H), 8.33-8.32 (m, 4H), 7.58-7.46 (m, 4H), 7.46-7.39 (m, 11H), 7.34 (s, 1H), 7.30-7.28 (m, 5H), 7.16 (s, 1H), 7.12-7.07 (m, 11H), 6.88 (d, J=5.0 Hz, 1H), 6:80 (d, J=2.8 Hz, 1H), 6.74 (d, J=5.0 Hz, 1H), 2.73-2.71 (m, 4H), 1.34-1.33 (m, 36H), 1.15-1.13 (m, 24H).

Next, the above isomeric mixture (h) (45 mg, 0.025 mmol) and PdCl$_2$ (PCy$_3$)$_2$ (6.0 mg, 8.1 μmol) were dried in vacuum in a Schlenk. 1,8-diazabicyclo[5.4.0]undeca-7-ene (25 μL, 0.17 mmol) and dimethylacetamide (2.5 mL) were added to this and mixed. The obtained mixture was frozen and deaired, the Schlenk was then sealed under N$_2$ atmosphere, and the mixture was heated at 140 degrees Celsius for 24 hours while being stirred. The mixture was then cooled to room temperature and separated by using silica gel column chromatography (hexane/dichloromethane, 1/2, v/v), and a compound (i) was obtained as a violet solid (13 mg, yield 30%). The spectrum data of the compound (i) was as follows.

$^1$H NMR (CDCl$_3$/C$_6$D$_6$ (1%), 600 MHZ): δ 9.48 (d, J=8.3 Hz, 4H), 8.38 (s, 4H), 7.93 (d, J=8.3 Hz, 4H), 7.67 (s, 4H), 7.48-7.46 (m, 10H), 7.32 (d, J=7.8 Hz, 4H), 7.17-7.15 (m, 8H), 7.01 (s, 4H), 2.79-2.75 (m, 4H), 1.39 (s, 36H), 1.18 (d, J=6.9 Hz, 24H); $^{13}$C NMR (CDCl$_3$/C$_6$D$_6$ (1%), 150 MHz):

δ 163.33, 155.15, 153.09, 147.65, 145.77, 138.10, 137.50, 137.02, 134.00, 129.78, 129.56, 128.38, 127.38, 126.81, 126.23, 124.05, 123.85, 122.80, 122.32, 121.55, 118.95, 34.60, 31.60, 29.23, 24.15. UV-vis-NIR (toluene): $\lambda_{max}$ (ε) 319 (9.1×10$^4$), 522 (8.9×10$^5$), 566 (1.3×10$^5$).
[Synthesis 2 of FLAP Precursor]
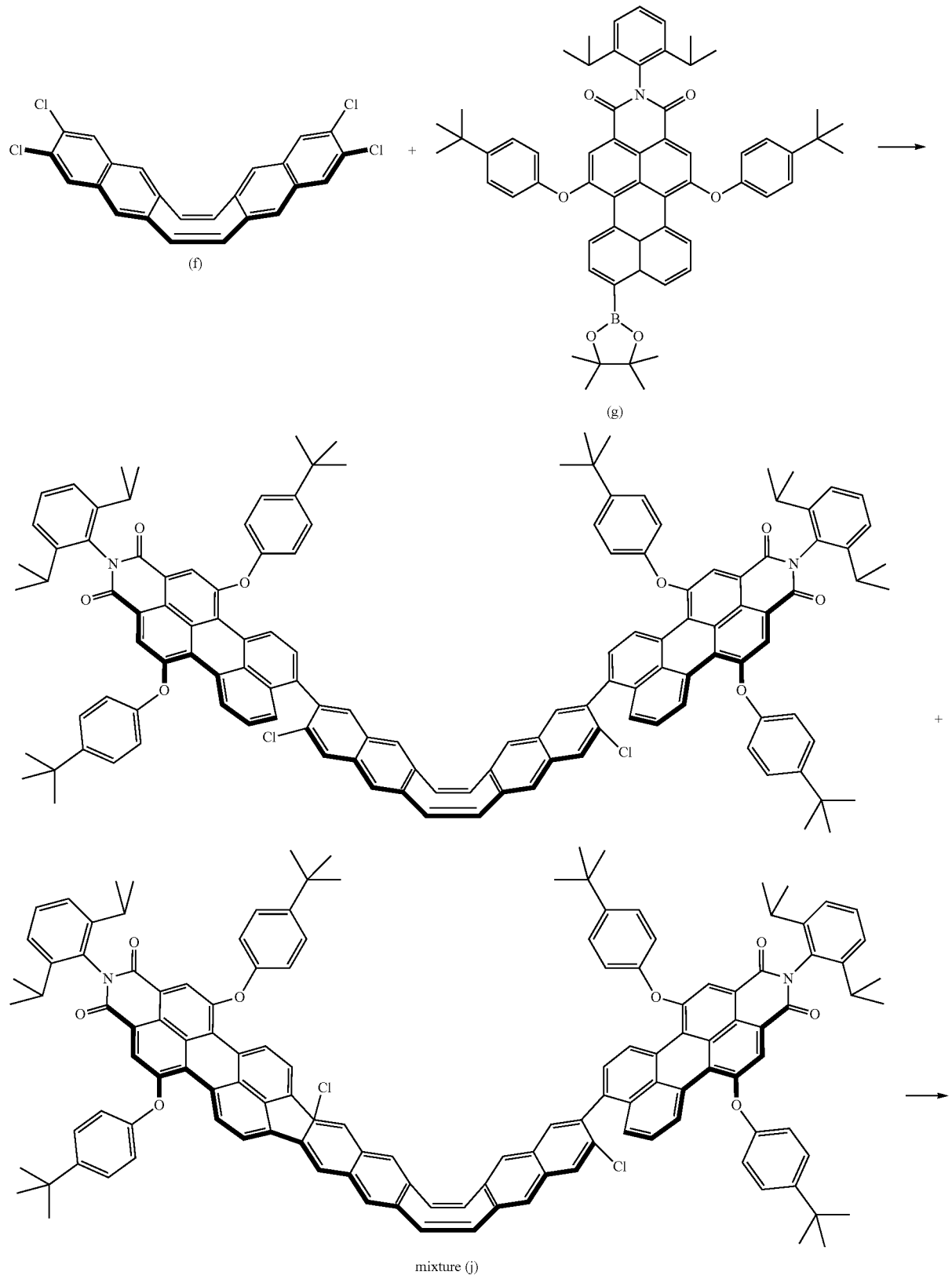

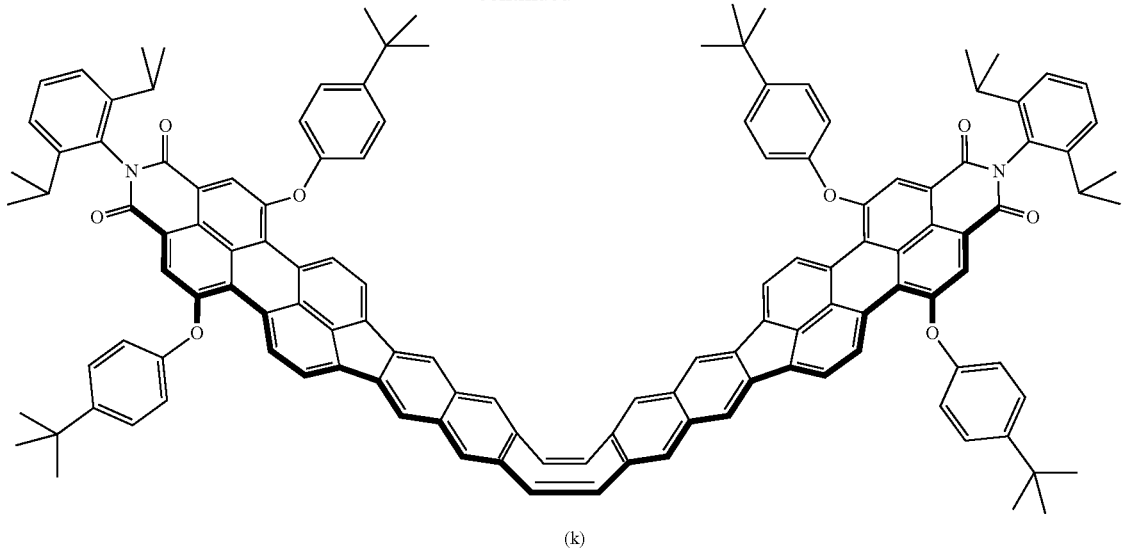

(k)

A mixture of the compound (g) synthesized in the section of [Synthesis 1 of FLAP precursor] (45 mg, 50 μmol), the compound (f) synthesized in the section of [Synthesis 2 of precursor] (8.8 mg, 20 μmol), palladium (II) acetate (Pd(OAc)$_2$) (0.45 mg, 2.0 μmol), 2-dicyclohexylphosphino-2',4',6'-triisopropyl biphenyl (XPhos; 1.9 mg, 4.0 μmol), tripotassium phosphate (21 mg, 0.10 mmol), and water (20 μL) was dissolved in THF (1.5 mL) in a Schlenk. The obtained mixture was frozen and deaired, the Schlenk was then sealed under N$_2$ atmosphere, and the mixture was heated at 60 degrees Celsius overnight while being stirred. The mixture was then cooled to room temperature, the solvent was evaporated. Purification was performed by column chromatography (hexane/dichloromethane, 1/1, v/v), and an isomeric mixture (j) was obtained as a red solid (16 mg, yield 42%). The spectrum data of the above (j) was as follows.

$^1$H NMR (CDCl$_3$, 600 MHz): δ 9.42-9.40 (m, 2H), 9.36-9.34 (m, 2H), 8.34-8.33 (m, 4H), 7.91 (d, J=11 Hz, 2H), 7.45 (d, J=11 Hz, 2H), 7.66-7.60 (m, 4H), 7.54-7.49 (m, 4H), 7.47-7.40 (m, 12H), 7.30-7.29 (m, 4H), 7.16-7.06 (m, 12H), 2.74-2.72 (m, 4H), 1.34-1.33 (m, 36H), 1.16-1.15 (m, 24H): ESI-HRMS: m/z 1923.7869 ([M+H]$^+$, C$_{132}$H$_{113}$Cl$_2$N$_2$O$_8$ requires: 1923.7869).

The above isomeric mixture (j) (30 mg, 0.016 mmol) and PdCl$_2$ (4.0 mg, 5.4 μmol) were dried in vacuum in a Schlenk. A mixture was made by adding 1,8-diazabicyclo[5.4.0]undeca-7-ene (15 μL, 0.10 mmol) and dimethylacetamide (2.5 mL) thereto. The obtained mixture was frozen and deaired, the Schlenk was then sealed under N$_2$ atmosphere, and the mixture was heated at 140 degrees Celsius for 22 hours while being stirred. The mixture was then cooled to room temperature and separated by using column chromatography (hexane/dichloromethane, 1/2, v/v). With precipitation of a benzene/methanol co-solvent system, a compound (k) was obtained as a dark blue solid (9.0 mg, 30%). The spectrum data of the compound (k) was as follows. The fluorescent wavelength of the compound (k) in a toluene solution was 603 nm, and the fluorescent quantum yield was 72%.

$^1$H NMR (CDCl$_3$/C$_6$D$_6$ (1%), 600 MHz): δ 9.54 (d, J=7.8 Hz, 4H), 8.42 (s, 4H), 8.17 (s, 4H), 8.03 (d, J=7.8 Hz, 4H), 7.74 (s, 4H), 7.50-7.47 (m, 10H), 7.35 (d, J=7.8 Hz, 4H), 7.16-7.15 (m, 12H); $^{13}$C NMR (CDCl$_3$/C$_6$D$_6$ (1%). 150 MHz): δ 163.34, 154.66, 153.21, 147.51, 145.78, 137.91, 137.37, 135.58, 134.98, 133.42, 132.57, 131.57, 130.84, 130.18, 129.56, 129.36, 127.36, 126.69, 124.19, 124.04, 123.76, 122.10, 120.86, 120.80, 118.72, 34.58, 31.60, 29.24, 24.16; ESI-HRMS: m/z 1851.8486 ([M+H]$^+$, C$_{132}$H$_{111}$N$_2$O$_8$ requires: 1851.8335); UV-vis-NIR (toluene): λ$_{max}$ (ε) 338 (7.3×10$^4$), 503 (2.7×10$^4$), 542 (7.8×10$^4$), 590 (1.3×10$^5$).

[Synthesis 3 of FLAP Precursor]

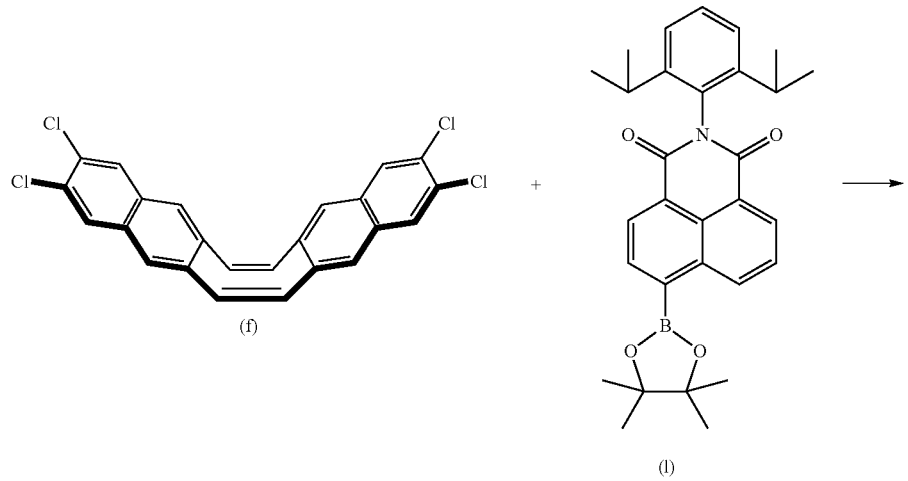

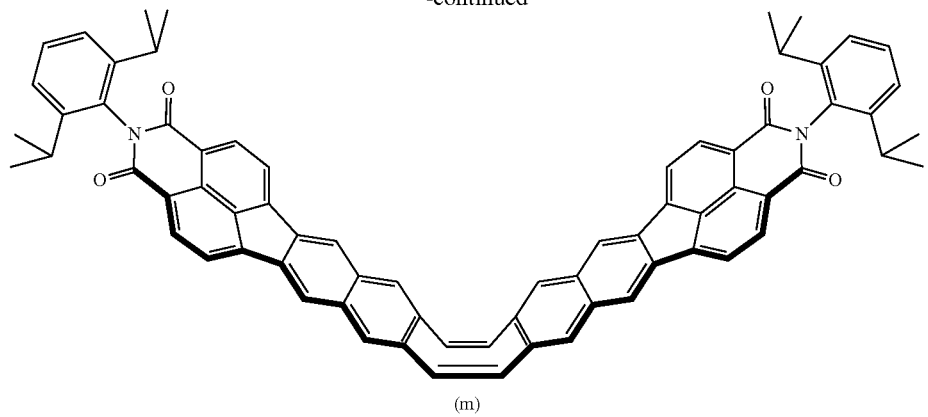

(m)

The compound (I) (synthesized in accordance with a method described in Chemistry of Materials, 2014, 26, p 4433-4446, 73 mg, 0.16 mmol), the compound (f) synthesized in the section of [Synthesis 2 of precursor] (28 mg, 63 μmol), Pd(OAc)$_2$ (1.5 mg, 6.6 μmol), XPhos (6.0 mg, 21 μmol), K$_3$PO$_4$ (67 mg, 0.32 mmol), and H$_2$O (10 μL) were dissolved in THF (2.5 mL) in a Schlenk. After the same operation as that in the synthesis method of the compound (j) in the section of [Synthesis 2 of FLAP precursor], the mixture was heated at 60 degrees Celsius for 12 hours. Then, after separation by silica gel column chromatography using methylene chloride as a solvent, the Suzuki coupling product was obtained as a mixture.

The obtained mixture was mixed to PdCl$_2$ (9.0 mg, 12 μmol) and dried in vacuum in a Schlenk. Furthermore, 1,8-diazabicyclo[5.4.0]undeca-7-ene (45 μL, 0.32 mmol), and dimethylacetamide (2.1 mL) were added, and after the same operation as the synthesis method of the compound (k) in the section of [Synthesis 2 of FLAP precursor], the mixture was heated at 140 degrees Celsius for 24 hours to cause reaction. The mixture was cooled to room temperature and separated by using column chromatography (hexane/dichloromethane, 1/4, v/v). By precipitation with a dichloromethane/methanol co-solvent system, a compound (m) was obtained as an orange solid (20 mg, yield 31%). The spectrum data of the compound (m) was as follows. The fluorescent wavelength in a toluene solution of the compound (m) was 497 nm, and the fluorescent quantum yield was 52%.

$^1$H NMR (CDCl$_3$, 600 MHz): δ 8.57 (d, J=7.2 Hz, 4H), 8.19 (s, 4H), 8.05 (d, J=7.2 Hz, 4H), 7.72 (s, 4H), 7.46 (t, J=7.8 Hz, 2H), 7.32 (d, J=7.8 Hz, 4H), 7.14 (s, 4H), 2.79-2.76 (m, 4H), 1.15 (d, J=6.4 Hz, 24H); $^{13}$C NMR (CDCl$_3$, 150 MHz): δ 164.11, 145.95, 142.75, 137.55, 136.65, 134.52, 133.52, 133.30, 132.97, 131.30, 129.67, 129.55, 126.67, 124.09, 122.93, 121.84, 120.06, 29.24, 24.13; APCI-HRMS: m/z 1010.4168 ([M]; C$_{72}$H$_{54}$N$_2$O$_4$ requires: 1010.4078); UV-vis-NIR (toluene): λ$_{max}$ (ε) 343 (1.1×10$^5$), 447 (6.3×10$^4$), 477 (8.2×10$^4$).

[Synthesis 4 of FLAP Precursor]

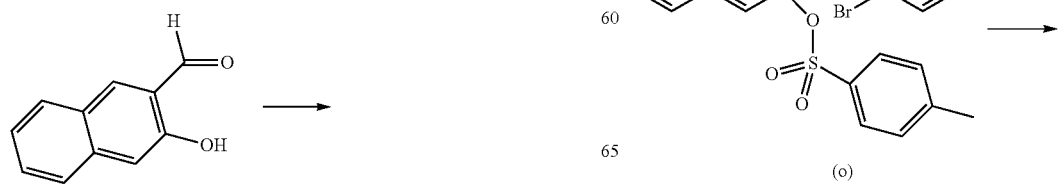

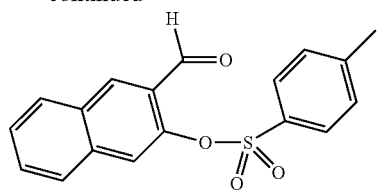

(n)

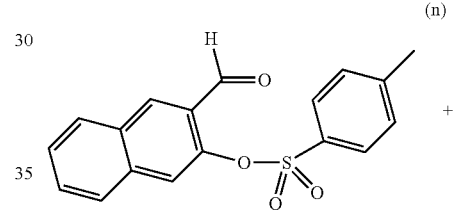

(n)

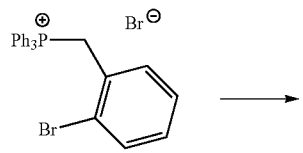

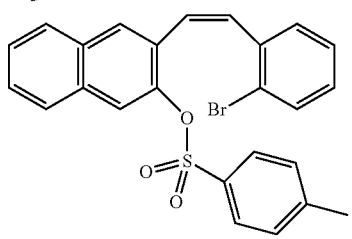

(o)

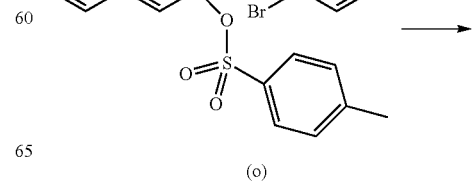

(o)

-continued

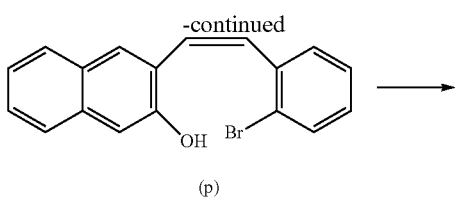

(p)

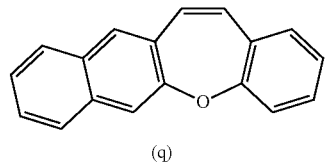

(q)

<Synthesis of Oxepine FLAP (Compound (q))>

2-Hydroxy-3-naphthaldehyde (synthesized in accordance with a method described in Journal of Organic Chemistry, 1988, 53, p 5345-5348, 90 mg, 0.50 mmol) and potassium carbonate (0.14 g, 1.0 mmol) were dissolved in acetonitrile (2 mL), which was cooled in an ice bath. An acetonitrile (2 mL) solution of tosylchloride (0.12 g, 0.60 mmol) was added to this solution. Next, the ice bath was removed, and this solution was stirred at room temperature for 2 hours. Water was added for quenching reaction, and the product was then extracted with ethyl acetate. The organic layer was passed through anhydrous sodium sulfate and silica gel column, and a compound (n) was obtained as a crude product.

Next, 2-bromobenzyl triphenylphosphonium bromide (synthesized in accordance with a method described in Organic Letters, 2013, 15, p 5448-5451, 0.31 g, 0.6 mmol) is suspended in anhydrous THE, which was cooled in an ice bath. Potassium t-butoxide (t-BuOK: 80 mg, 0.71 mmol) was added to the solution in the ice bath, and the mixture was stirred at 0 degree Celsius for 30 minutes under a nitrogen atmosphere. The compound (n) that was a crude product was then dissolved in THE (5 mL) and added to a reaction mixture in the ice bath, and the mixture was stirred for 12 hours while the reaction temperature was gradually increased back to room temperature. Water (25 mL) and ethyl acetate (50 mL) were added to extract a product, and the organic layer was passed through anhydrous sodium sulfate and silica gel column. The solvent was distilled, and a compound (o) was obtained as a crude product.

The compound (o) was dissolved in ethanol (15 mL) and water (15 mL), potassium hydroxide (0.9 g, 16 mmol) was added, and the reaction product were heated and refluxed for 1 hour and then cooled back to room temperature. Next, 10 mass % of hydrochloric acid was used to adjust pH to 4, and extraction was performed with dichloromethane. The organic layer was washed with a sodium hydrogen carbonate solution, and the organic layer was passed through anhydrous sodium sulfate and silica gel column. The solvent was then distilled, and a compound (p) was obtained as a crude product.

The crude product (p) was mixed with potassium carbonate (0.28 g, 2.0 mmol) and dissolved in NMP (6 mL), and the mixture was heated at 120 degrees Celsius for 20 hours under a nitrogen atmosphere. The reaction product was subjected to silica gel column chromatography (hexane/dichloromethane, 3/1 by volume), and a compound (q) was obtained as a colorless solid (69 mg, 57%). The spectrum data of the compound (q) was as follows. The fluorescent wavelength in a dichloromethane solution of the compound (q) was 476 nm, and the fluorescent quantum yield was 10%.

$^1$H NMR (CDCl$_3$, 600 MHz): δ 7.77-7.75 (m, 2H), 7.62 (s, 1H), 7.60 (s, 1H), 7.44-7.38 (m, 2H), 7.32-7.28 (m, 2H), 7.21-7.18 (m, 1H), 7.14-7.11 (m, 1H), 6.87 (d, J=12 Hz, 1H), 6.70 (d, J=12 Hz, 1H); 18C NMR (CDCl$_3$, 150 MHz): δ 157.60, 156.38, 134.51, 131.24, 130.74, 130.51, 130.18, 129.87, 129.77, 128.89, 127.90, 127.20, 126.62, 125.65, 125.05, 121.67, 117.96.

[Synthesis 5 of FLAP Precursor]

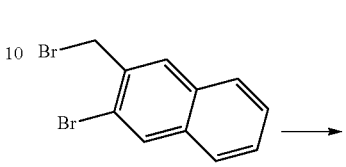

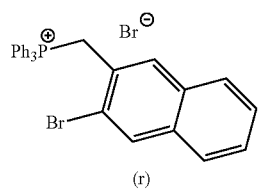
(r)

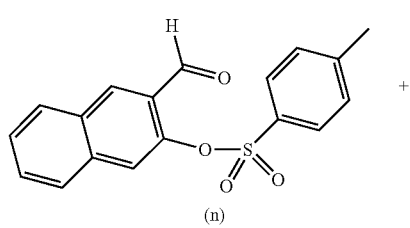
(n)

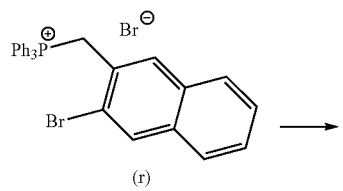
(r)

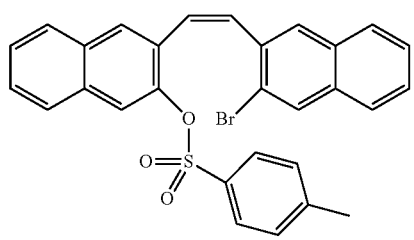
(s)

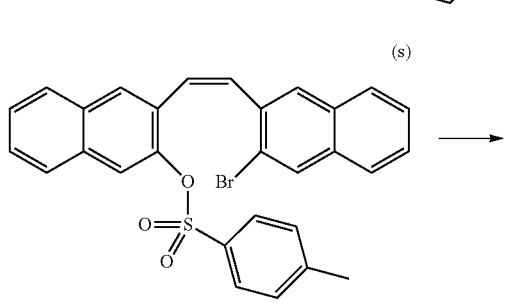
(s)

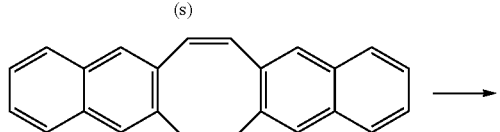
(t)

-continued

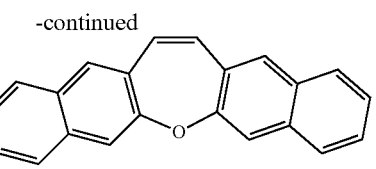

(u)

<Synthesis of Compound (r)>

2-bromo-3-bromomethylnaphthalene (synthesized in accordance with a method described in Angewandte Chemistry International Edition, 2016, 55, p 11120-11123, 60 mg, 0.20 mmol) and triphenylphosphine ($PPh_3$, 60 mg, 0.23 mmol) were dissolved in dehydrated dimethylformamide (2 mL), which was stirred at room temperature for 12 hours under a nitrogen atmosphere. Methylene chloride (2 mL) and diethyl ether (40 mL) were then added, and a product was precipitated. The suspension was filtered, washed with diethyl ether, and thereby a compound (r) was obtained as a white solid (87 mg, yield 80%). The spectrum data of the compound (r) was as follows.

$^1$H NMR ($CDCl_3$, 600 MHz): δ 8.09 (d, J=3.7 Hz, 1H), 7.89 (s, 1H), 7.80-7.71 (m, 9H), 7.67-7.60 (m, 8H), 7.50-7.43 (m, 2H), 5.88 (d, J=14 Hz, 2H); $^{13}$C NMR ($CDCl_3$, 150 MHz): δ 135.25, 134.40, 134.33, 133.81, 132.94, 132.89, 132.08 131.57, 130.33, 130.24, 128.17, 127.82, 127.05, 126.55, 124.22, 124.15, 123.62, 117.64, 117.08, 31.09, 30.76; $^{31}$P NMR ($CDCl_3$, 243 MHz): δ 22.96.

<Synthesis of Oxepine FLAP (Compound (u))>

The above compound (r) (87 mg, 0.16 mmol) was suspended in anhydrous THF (2.5 mL), which was cooled in an ice bath. To the solution in the ice bath, t-BuOK (20 mg, 0.18 mmol) was added, and the mixture was stirred at 0 degree Celsius for 30 minutes under a nitrogen atmosphere. A crude product of the compound (n) synthesized at 25 mol % of scale of the method described in Example 6 was then dissolved in THF (1 mL) and added to the reaction mixture in the ice bath, and the mixture was stirred for 12 hours while the reaction temperature was gradually increased back to room temperature. Water (7 mL) and ethyl acetate (15 mL) were added to extract a product, and the organic layer was passed through anhydrous sodium sulfate and silica gel column. The solvent was distilled, and a compound(s) was obtained as a crude product.

The compound(s) was dissolved in ethanol (5 mL) and water (5 mL), potassium hydroxide (0.30 g, 5.3 mmol) was added, the reaction mixture was refluxed for 1 hour, and the temperature was increased back to room temperature. This reaction liquid was subjected to the same operation as that for the compound (p) of Example 6 below, and a compound (t) was obtained as a crude product.

The crude product (t) was mixed with potassium carbonate (90 mg, 0.64 mmol) and dissolved in NMP (2 mL), which was heated at 120 degrees Celsius for 20 hours under nitrogen. The reaction mixture was subjected to silica gel column chromatography (hexane/dichloromethane, 4/1 by volume), a compound (u) was obtained as an insoluble colorless solid (6.0 mg, yield 13%). The spectrum data of the compound (u) was as follows. The fluorescent wavelength of the compound (u) in a dichloromethane solution was 479 nm, and the fluorescent quantum yield was 5%.

$^1$H NMR (DMSO-$d_6$, 120° C., 600 MHz): δ 7.88-7.85 (m, 6H), 7.79 (s, 2H), 7.49-7.45 (m, 4H), 6.98 (s, 2H); $^{13}$C NMR (DMSO-$d_6$, 120° C., 150 MHz): δ 154.80, 133.38, 130.30, 129.54, 128.93, 128.52, 127.11, 126.34, 126.10, 125.05, 116.96.

[Synthesis 6 of FLAP Precursor]

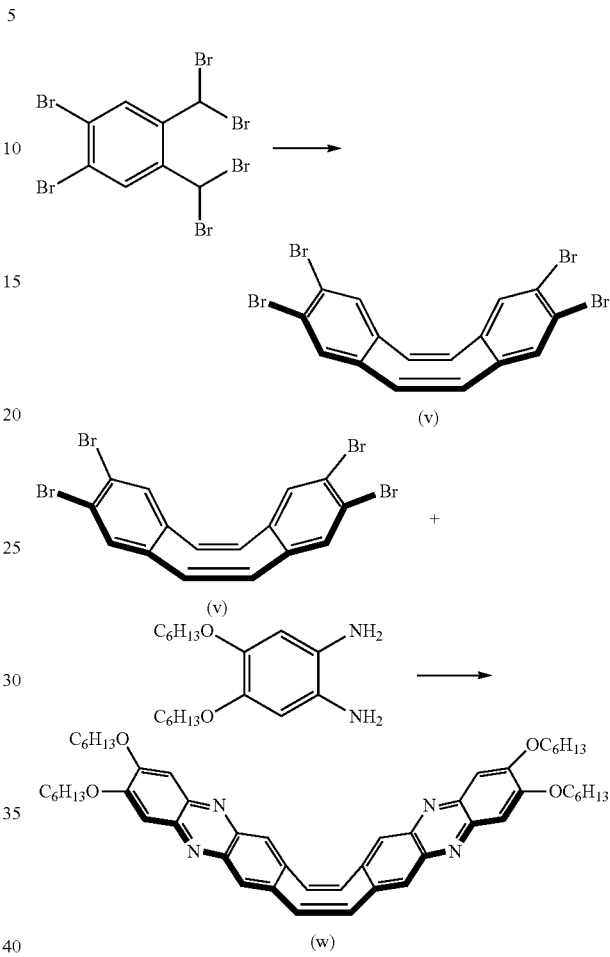

<Synthesis of Compound (v)>

After α,α,α',α',4,5-hexabromo-o-xylene (Tokyo Chemical Industry Co., Ltd.) (1.21 g, 2.0 mmol) and sodium iodide (3.0 g, 20 mmol) were dried in vacuum for 10 minutes in a Schlenk, 3 mL of ultra-dehydrated DMF was added under an argon atmosphere, and the mixture was heated to 170 degrees Celsius and stirred for 4 hours. This reaction mixture was allowed to be cooled to room temperature, a sodium thiosulfate solution was added, and extraction was performed with hexane/dichloromethane mixture solvent (10:1 by volume). The organic layer was passed through anhydrous sodium sulfate to remove water, the solvent was distilled, and thereby a dark brown solid of a crude product was obtained. Purification by silica gel column chromatography (hexane/dichloromethane mixture solvent, 30:1) was performed on the crude product, and a compound (v) was obtained as a white solid (158 mg, 30%). The spectrum data of the compound (v) was as follows.

$^1$H NMR ($CDCl_3$, 600 MHz): δ/ppm=7.31 (s, 4H), 6.65 (s, 4H); $^{13}$C NMR ($CDCl_3$, 600 MHz): δ/ppm=137.32 (4C), 133.8141 (4C), 133.8141 (4C), 132.5693 (4C); MARDI-TOF-MS: m/z=519.73.

<Synthesis of Phenazine Based FLAP Precursor (Compound (W))>

The compound (v) (156 mg, 0.30 mmol), 4,5-dihexyl oxy-1,2-phenylenediamine (synthesized by a method described in J. Mater. Chem., 2012, 22, 4450, 196 mg, 0.64 mmol), palladium (II) acetate (14 mg, 0.06 mmol), 2-dicyclohexylphosphino-2',6'-dimethoxybiphenyl (SPhos; 25 mg, 0.06 mmol), and cesium carbonate (650 mg, 6.6 mmol) were dried in vacuum for 10 minutes in a Schlenk, toluene 2.4 mL deaired under an argon atmosphere was added, and the mixture was heated at 110 degrees Celsius for 32 hours. Palladium (II) acetate (14 mg, 0.06 mmol) and SPhos (25 mg, 0.06 mmol) were added, and the mixture was further heated at 110 degrees Celsius for 16 hours. This reaction mixture was allowed to be cooled to room temperature, diluted with excessive amount of chloroform, and suctioned and filtered, and the filtrate was condensed by using a rotary evaporator to obtain a dark brown solid crude product. The crude product was purified by silica gel column chromatography (dichloromethane/ethyl acetate mixture solvent, 5:1 by volume) and then gel filtration chromatography (chloroform, 0.5% triethylamine mixture solvent), and a dark brown crude crystal was obtained. Recrystallization was performed using chloroform as a good solvent and methanol as a poor solvent, a compound (w) was obtained as a yellow crystal (11 mg, 4%). The spectrum data of the compound (w) was as follows. The fluorescent wavelength in a dichloromethane solution of the compound (w) was 518 nm, and the fluorescent quantum yield was 42%. Further, in a polymer thin film, the fluorescent wavelength was 460 nm, and the fluorescent quantum yield was 13%. While long wavelength fluorescence due to the planar shape was exhibited in the dichloromethane solution, short wavelength fluorescence due to the V-shape was exhibited in the polymer thin film. Since this indicates that the planar shape and the V-shape have different π-conjugate structures, respectively, it is expected that the compound (w) functions as a stress probe.

$^1$H NMR (CDCl$_3$, 600 Hz): δ/ppm=7.92 (s, 4H), 7.24 (s, 4H), 7.23 (s, 4H), 7.30 (s, 4H), 4.18 (t, J=6.6 Hz, 8H), 1.92 (tt, J$_1$=6.7 Hz, J$_2$=6.7 Hz, 8H), 1.35-1.38 (m, 24H), 0.91 (t, J=7.0 Hz, 12H). $^{13}$C NMR (CDCl$_3$, 600 MHz): δ/ppm=154.63 (4C, C), 142.49 (4C, CH), 140.86 (4C, C), 137.95 (4C, C), 133.27 (4C, CH), 128.38 (4C, C), 105.57 (4C, CH), 69.40 (4C, CH$_2$), 31.65 (4C, CH$_2$), 28.81 (4C, CH$_2$), 25.82 (4C, CH$_2$), 22.73 (4C, CH$_2$), 14.15 (4C, CH$_3$). MARDI-TOF-MS: m/z=808.71.

[Synthesis 7 of FLAP Precursor]

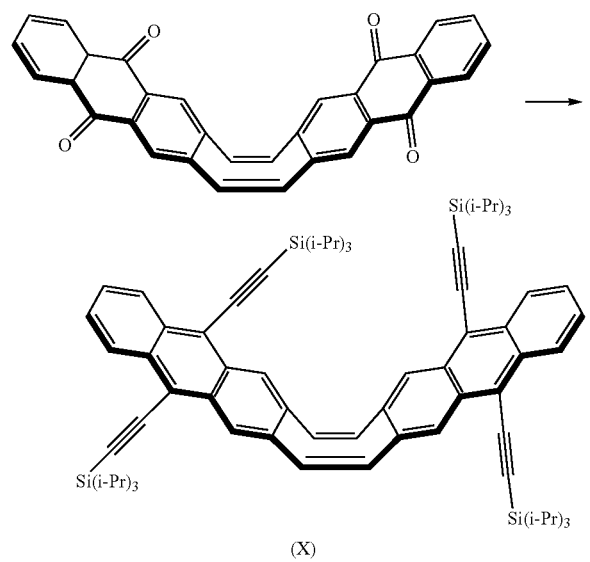

(X)

<Synthesis of Acetylene Modified FLAP Precursor>

An isopropyl magnesium chloride solution (2.0 M, 11 mL of tetrahydrofuran, 22 mol) and tetrahydrofuran (20 mL) were put in a Schlenk, and triisopropylsilylacetylene (4.9 mL, 22 mmol) was dripped under argon. The reaction mixture liquid was heated to 60 degrees Celsius and stirred for 20 minutes. After cooled back to room temperature, a cyclooctatetraene condensed-ring anthraquinone dimer (synthesized in accordance with a method described in Zhurnal Organicheskoi Khimii (1977), 13 (6), 1341) (0.84 g, 1.8 mmol) and tetrahydrofuran (5 mL) were added to the reaction mixture liquid, and the suspension was stirred at 60 degrees Celsius for 35 hours. After cooled back to room temperature, tin (II) chloride (2.1 g, 11 mmol) dissolved in 10 mass % of dilute hydrochloric acid (10 mL) was added, and the mixture was stirred at 60 degrees Celsius for 2 hours. The reaction liquid was diluted with methylene chloride and extracted. After the organic layer was washed with a saturated saline solution and dehydrated with anhydrous sodium sulfate, the solvent was distilled away. The residue was subjected to silica gel column chromatography (eluate: hexane and then hexane/dichloromethane mixture liquid, 20/1 by volume), and a compound (x) was obtained as a yellow solid (250 mg, 12%). Furthermore, recrystallization was performed with dichloromethane and a methanol solvent, and thereby a product was able to be purified. The spectrum data of the product was as follows. The fluorescent wavelengths of the compound (x) in the dichloromethane solution were 470 nm and 504 nm, and the fluorescent quantum yield was 18%. In the crystal, the fluorescent wavelengths were 544 nm and 588 nm, and the fluorescent quantum yield was 10%. While short wavelength fluorescence due to the V-shape was exhibited in the dichloromethane solution, long wavelength fluorescence due to the planar shape was exhibited in the crystal. Since this result indicates that the planar shape and the V-shape have different π-conjugate structures, respectively, it is expected that the compound (x) functions as a stress probe.

$^1$H NMR (600 MHZ, CDCl$_3$): δ 8.51 (dd, J=6.9, 3.3 Hz, 4H), 8.45 (s, 4H), 7.51 (dd, J=6.6, 3.0 Hz, 4H), 7.17 (s, 4H), 1.34-1.29 (m, 12H), and 1.27 (d, J=5.4 Hz, 72H) ppm; $^{13}$C NMR (101 MHz, CDCl$_3$): δ 135.8, 133.4, 132.6, 131.6, 128.1, 127.4, 126.9, 118.4, 105.2, 103.5, 19.0, and 11.7 ppm; melting point: >200° C.; UV-visible absorption (in CH$_2$Cl$_2$): λ$_{max}$=319, 410, 434, and 461 nm; fluorescence (in CH$_2$Cl$_2$, λ$_{ex}$=410 nm): λ$_{max}$=470 and 504 nm, Φ$_F$=0.18.

[Synthesis 3 of Precursor]

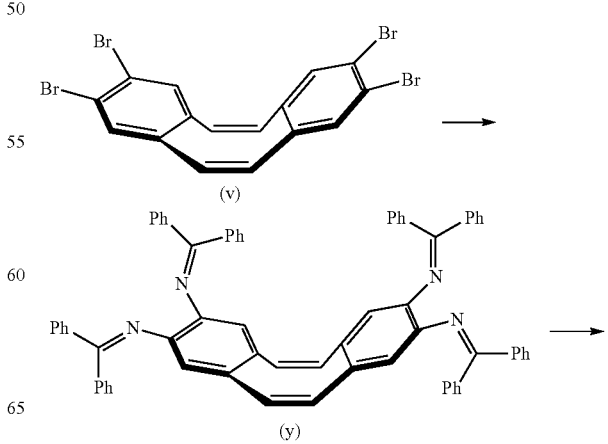

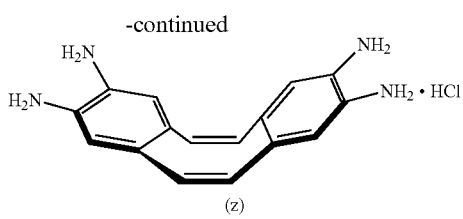

<Synthesis of Compound (y)>

Tris(dibenzylidene acetone) dipalladium (44 mg, 48 µmol) and rac-BINAP (60 mg, 96 µmol) were put in a flask, and toluene (7.5 mL) was added under an argon atmosphere. After frozen and deaired for three times, the mixture was stirred at 110 degrees Celsius for 30 minutes. After allowed to be cooled to room temperature, benzophenone-imine (0.26 mL, 1.6 mmol), the compound (v) (160 mg, 0.30 mmol), and t-butoxy sodium (150 mg, 1.56 mmol) were added and stirred at 110 degrees Celsius for 13 hours. After allowed to be cooled to room temperature, the reaction mixture was filtered with celite, and the solvent was distilled away. The residue was purified by silica gel column chromatography (eluate: ethyl acetate/hexane/triethylamine=10/88/2), and a crude product of a compound (y) was obtained. Furthermore, the crude product was re-precipitated with dichloromethane/hexane, and thereby the compound (y) was obtained as a yellow solid (190 mg, yield 67%).

$^1$H NMR (CDCl$_3$, 600 MHZ): δ/ppm=7.66 (d, 8H), 7.38 (t, 4H), 7.33-7.27 (m, 12H), 7.19 (t, 8H), 6.85 (d, 8H), 6.20 (s, 4H), 6.09 (4H).

<Synthesis of Precursor Modified by Amino Group (Compound (z))>

The compound (y) (46 mg, 50 µmol), tetrahydrofuran (3.0 mL), and 2.0 M of hydrochloric acid (0.1 mL) were put in and stirred at room temperature for 3 hours. The solvent was distilled away from a reaction liquid, and a compound (z) was obtained as a light-brown solid (21 mg, 10%) by filtration.

$^1$H NMR (DMSO-d$_6$, 600 MHz): δ/ppm=6.67 (s), 6.55 (s), 3.7 (s, broad).

[Synthesis 8 of FLAP Precursor]

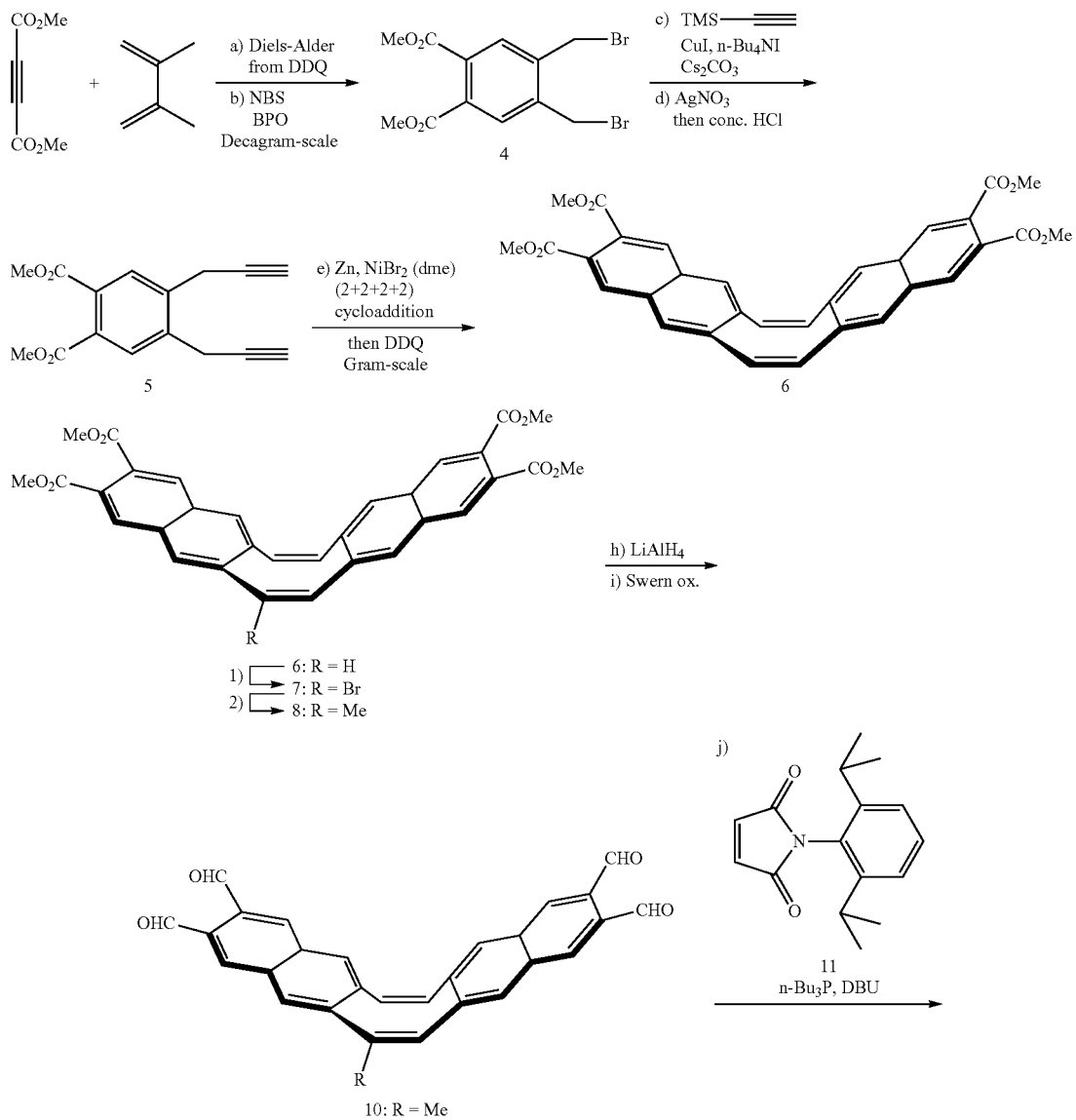

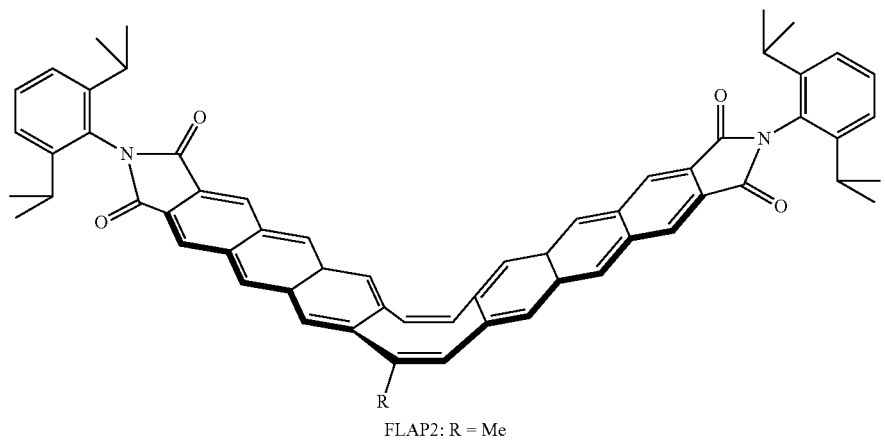

FLAP2: R = Me (a) Dimethylacetylene dicarboxylate (1.0 equivalent amount) and 2,3-dimethyl-1,3-butadiene (1.0 equivalent amount) were dissolved in toluene, which was stirred at 70 degrees Celsius for 18 hours. Next, DDQ (2,3-dichloro-5,6-dicyano-1,4-benzoquinone; 1.1 equivalent amount) was added, and the mixture was stirred at 70 degrees Celsius for 6 hours.

(b) NBS (N-bromosuccinimide; 2.2 equivalent amount), BPO (benzoyl peroxide; 5 mol %), and α,α,α-trifluorotoluene were added and stirred at 100 degrees Celsius for 10 hours, and thereby a compound 4 was obtained.

(c) CuI (2.0 equivalent amount), n-Bu$_4$NI (2.0 equivalent amount), Cs$_2$CO$_3$ (2.1 equivalent amount), TMS (trimethylsilyl) acetylene (5.0 equivalent amount), and MeCN were added and stirred at 50 degrees Celsius for 20 hours.

(d) AgNO$_3$ (10 equivalent amount) and CH$_2$Cl$_2$/acetone/H$_2$O were added and stirred at room temperature for 1 hour. Next, an excessive amount of concentrated hydrochloric acid was added, and a compound 5 was obtained by stirring at room temperature for 1 hour.

(e) Zn (50 mol %), NiBr$_2$ (dme; 1,2-dimethoxyethane) (25 mol %), and THF/H$_2$O were added and stirred at 60 degrees Celsius for 2 hours. Next, DDQ (4.2 equivalent amount) and toluene were added and stirred at room temperature for 30 minutes, and thereby a compound 6 was obtained.

(f) Br$_2$ (1.1 equivalent amount) and CH$_2$Cl$_2$ were and stirred at 40 degrees Celsius for 2 hours. Next, DBU (1,8-diazabicyclo[5.4.0]undeca-7-ene; 10 equivalent amount) and benzene were added and stirred at 80 degrees Celsius for 1 hour.

(g) MeB (OH)$_2$ (4.0 equivalent amount), K$_3$PO$_4$ (4.0 equivalent amount), PPh$_3$ (40 mol %), Pd(OAc)$_2$ (10 mol %), and THF were added and refluxed for 24 hours.

(h) LiAlH$_4$ (4.5 equivalent amount) and THF were added and stirred at 60 degrees Celsius for 4 hours.

(i) (COCl)$_2$ (4.4 equivalent amount), DMSO (8.8 equivalent amount), and CH$_2$Cl$_2$ were added and stirred at −78 degrees Celsius for 6 hours. Then, NEt$_3$ (35 equivalent amount) was added, and the mixture was stirred at 0 degree Celsius for 2 hours.

(j) Maleimide (compound 11) (2.4 equivalent amount), PBu$_3$ (2.6 equivalent amount), DBU (0.20 equivalent amount), and 1,2-dichloroethane were added and stirred at 80 degrees Celsius for 40 hours, and thereby a FLAP precursor compound (FLAP2) was obtained.

[Synthesis of FLAP]

Example 1a

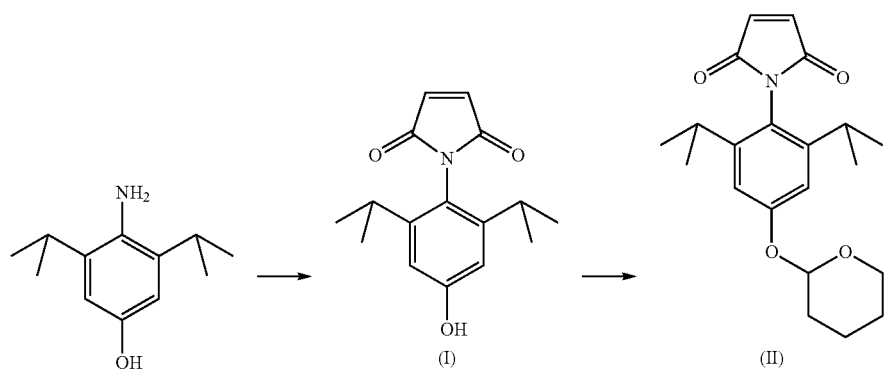

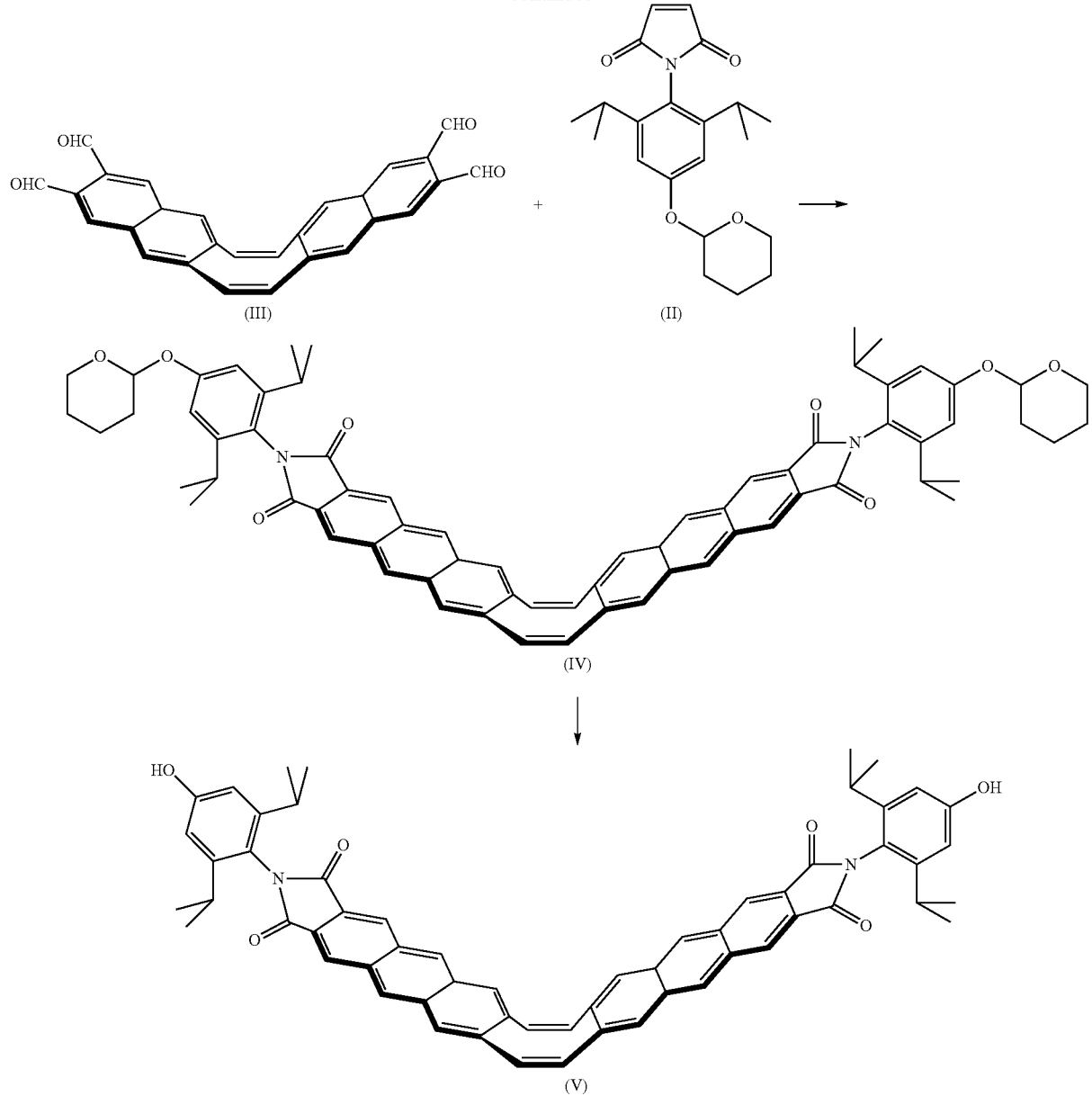

Synthesis of N-(4-hydroxy-2,6-diisopropylphenyl) maleimide (Compound (I))

Under an argon atmosphere, 4-amino-3,5-diisopropylphenyl(synthesized in accordance with a method described in Advanced Synthesis & Catalysis, 2014, 356, p 460-474, 2.8 g, 14 mmol) and maleic anhydride (1.7 g, 17 mmol) were dissolved in acetic acid (70 mL), which was stirred at 110 degrees Celsius for 14 hours. Then, after the reaction mixture was diluted with acetic acid, extracted by using a sodium hydrogen carbonate solution and a saturated saline solution, and dehydrated by passing the organic layer through anhydrous sodium sulfate, the solvent was distilled away. The obtained crude product was purified by silica gel column chromatography (eluate: methylene chloride/ethyl acetate=20/1) and then recrystallized by using hexane, and thereby a compound (I) was obtained as a white solid (3.08 g, 79%). The spectrum data of the compound (I) was as follows.

$^1$H NMR (600 MHZ, CDCl$_3$) δ (ppm) 6.87 (s, 2H), 6.69 (s, 2H), 4.80 (s, 1H), 2.56 (sept, J=6.9 Hz, 2H) and 1.13 (d, J=6.9 Hz, 12H); $^{13}$C NMR (150 MHz, CDCl$_3$) δ (ppm) 171.0, 157.1, 149.5, 134.4, 119.0, 111.2, 29.5 and 24.0; HR-APCI TOF-MS (m/z) found 273.1358, calcd for C$_{16}$H$_{19}$NO$_3$: 273.1365 [M].

Synthesis of N-(2,6-diisopropyl-4-(tetrahydropyranyloxy)phenyl)-maleimide (Compound (II))

Under an argon atmosphere, the compound (I) (3.1 g, 11 mmol) and pyridinium paratoluenesulfonate (310 mg, 1.2 mmol) were dissolved in methylene chloride (85 mL), 3,4-dihydro-2H-pyran (2.9 mL, 33 mmol) was added at 0 degrees Celsius, and the mixture was stirred at room temperature for 12 hours. After the reaction solution with added water was washed with a saturated saline solution, the organic layer was passed through anhydrous sodium sulfate for dehydration, and the solvent was distilled away. Recrystallization was performed with a mixture solvent of methylene chloride and hexane, and thereby a compound (II) was obtained as white powder (3.86 g, 96%). The spectrum data of the compound (II) as follows.

$^1$H NMR (600 MHz, CDCl$_3$) § (ppm) 6.92 (s, 2H), 6.86 (s, 2H), 5.45 (m, 1H), 3.92 (m, 1H), 3.63 (m, 1H), 2.57 (sept, J=6.9 Hz, 2H), 2.02 (m, 1H), 1.87 (m, 2H), 1.67-1.69 (m, 2H), 1.62-1.63 (m, 1H) and 1.13 (d, J=6.9 Hz, 12H); $^{13}$C NMR (150 MHz, CDCl$_3$) δ (ppm) 170.9, 158.7, 148.9, 134.4, 119.5, 111.2, 96.3, 61.9, 30.5, 29.5, 25.4, 24:0 and 18.7.

<Synthesis Method of Compound (IV)>

Under an argon atmosphere, the compound (II) (560 mg, 1.6 mmol) was dissolved in 1,2-dichloroethane (12 mL), tributylphosphine (410 μL, 1.7 mmol) was added at 0 degree Celsius, and the mixture was stirred at room temperature for 30 minutes. To this reaction solution, 1,2-dichloroethane solution (10 mL) of a compound (III) (synthesized in accordance with a method described in Journal of Materials Chemistry C, 2017, 5, p 5248-5256, 270 mg, 0.65 mmol) was added at 0 degree Celsius, then diazabicycloundecene (20 μL, 0.13 mmol) were added. The reaction solution was stirred at 80 degrees Celsius for 15 hours. After the reaction solution with added water was washed with a saturated saline solution, the organic layer was passed through anhydrous sodium sulfate for dehydration, and the solvent was distilled away. The crude product was purified by silica gel column chromatography (eluate: methylene chloride/hexane/ethyl acetate=1/1/1), and thereby a compound (IV) was obtained as a yellow solid (140 mg, 20%). The spectrum data of the compound (IV) was as follows.

$^1$H NMR (600 MHZ, CDCl$_3$) δ (ppm) 8.55 (s, 4H), 8.54 (s, 4H), 7.94 (s, 4H), 7.24 (s, 4H), 6.98 (s, 4H), 5.49 (m, 2H), 3.95 (m, 2H), 3.64 (m, 4H), 2.71 (sept, J=6.9 Hz, 4H), 2.04 (m, 2H), 1.87 (m, 4H), 1.71-1.70 (m, 4H), 1.60-1.62 (m, 2H) and 1.15 (d, J=6.9 Hz, 24H); $^{13}$C NMR (150 MHz, CDCl$_3$) δ (ppm) 168.1, 158.9, 148.5, 136.7, 133.4, 132.5, 132.3, 129.9, 128.6, 126.7, 120.8, 112.1, 96.4, 62.0, 30.6, 29.7, 25.5, 24.1 and 18.8 (19 peaks were observed for 20 carbons due to partial signal coverage.)

<Synthesis of Both Terminals OH Modified FLAP (Compound (V))>

The compound (IV) (140 mg, 0.13 mmol) was dissolved in methylene chloride (30 mL) and methanol (10 mL), trifluoroacetic acid (2.0 mL, 0.16 mmol) was added, and the mixture was stirred at room temperature for 4 hours. After the reaction solution with added water was washed with a saturated saline solution, the organic layer was passed through anhydrous sodium sulfate for dehydration, and the solvent was distilled away. The crude product was purified by silica gel column chromatography (eluate: methylene chloride/ethyl acetate=1/1), recrystallization was further performed with a mixture solvent of methylene chloride and hexane, and thereby a compound (V) was obtained as a yellow solid (110 mg, 92%). The spectrum data of the compound (V) was as follows.

$^1$H NMR (600 MHz, CDCl$_3$) δ (ppm) 8.55 (m, 8H), 7.94 (s, 4H), 7.24 (s, 4H), 6.75 (s, 4H), 4.83 (s, 4H), 2.70 (sept, J=6.9 Hz, 4H) and 1.14 (d, J=6.9 Hz, 24H); $^{13}$C NMR (150 MHz, DMSO-da) δ (ppm) 167.5, 158.6, 147.9, 136.1, 133.1, 131.9, 131.4, 130.0, 128.3, 126.6, 125.7, 118.4, 110.5, 28.6 and 23.5.

Example 1b

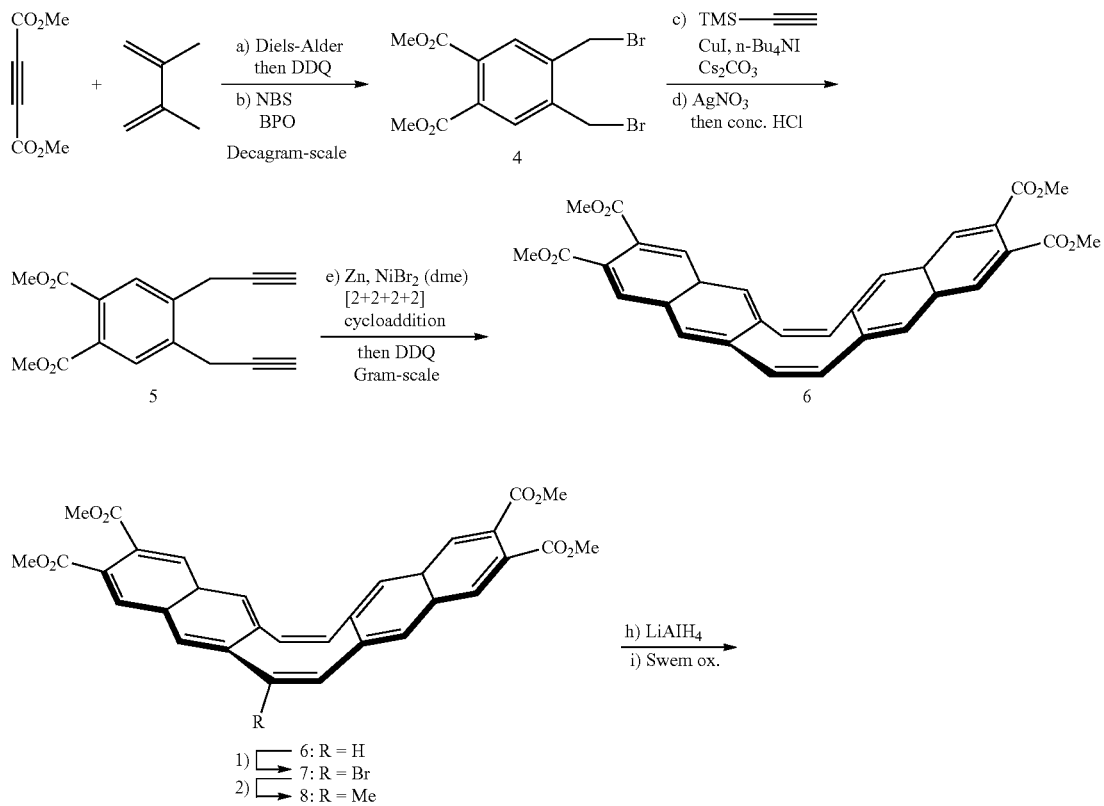

-continued

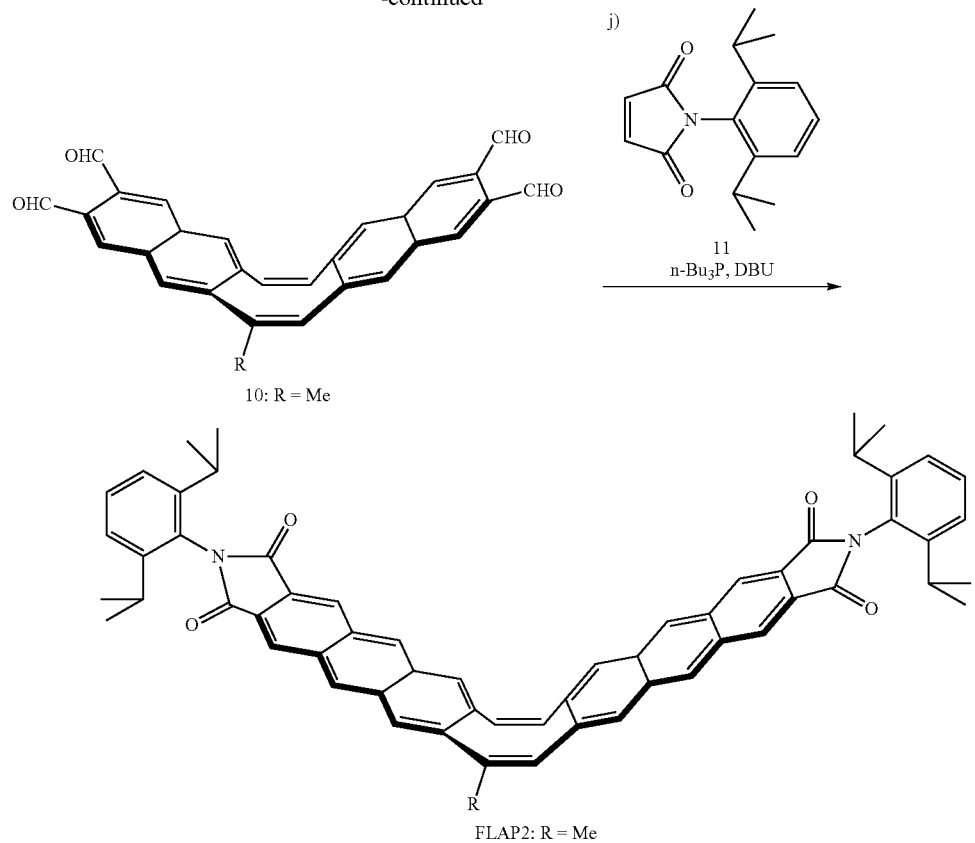

<Synthesis of Both Terminals OH Modified FLAP (Compound (V')) Having Substituent Group in Ring A>

To obtain a compound (V') that is a FLAP in which both terminals of the FLAP denoted as "FLAP2: R=Me" represented in Formula 32 are modified by OH groups as polymerizable groups, OH groups having protective groups are introduced to both the terminals of a FLAP having a substituent group in the ring A by using the same method as the method represented in Formula 32 except that (a) the compound (II) represented in Formula 31 (that is, N-(2,6-diisopropyl-4-(tetrahydropyranyloxy)phenyl)-maleimide) or (b) the compound (IX) represented in Formula 33 illustrated below (that is, N-(4-(1,3-dimethoxypropanil)-2,6-diisopropylphenyl)-maleimide is used instead of the compound (11) represented in Formula 32 (that is, N-(2,6-diisopropylphenyl)-maleimide). The compound (V'), which is a FLAP having a substituent group in the ring A and modified by OH groups as a polymerizable group at both the terminals, is obtained by de-protecting the protective groups for the obtained compound in which OH groups having protective groups are introduced to both the terminals of a FLAP having a substituent group in the ring A by using the same method as a de-protection reaction for obtaining (a) the compound (V) from the compound (IV) represented in Formula 31 or (b) the compound (XI) from the compound (X) represented in Formula 33 illustrated below.

Example 2

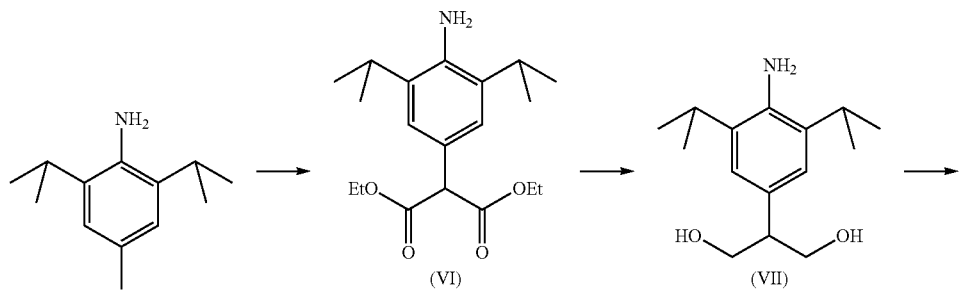

-continued

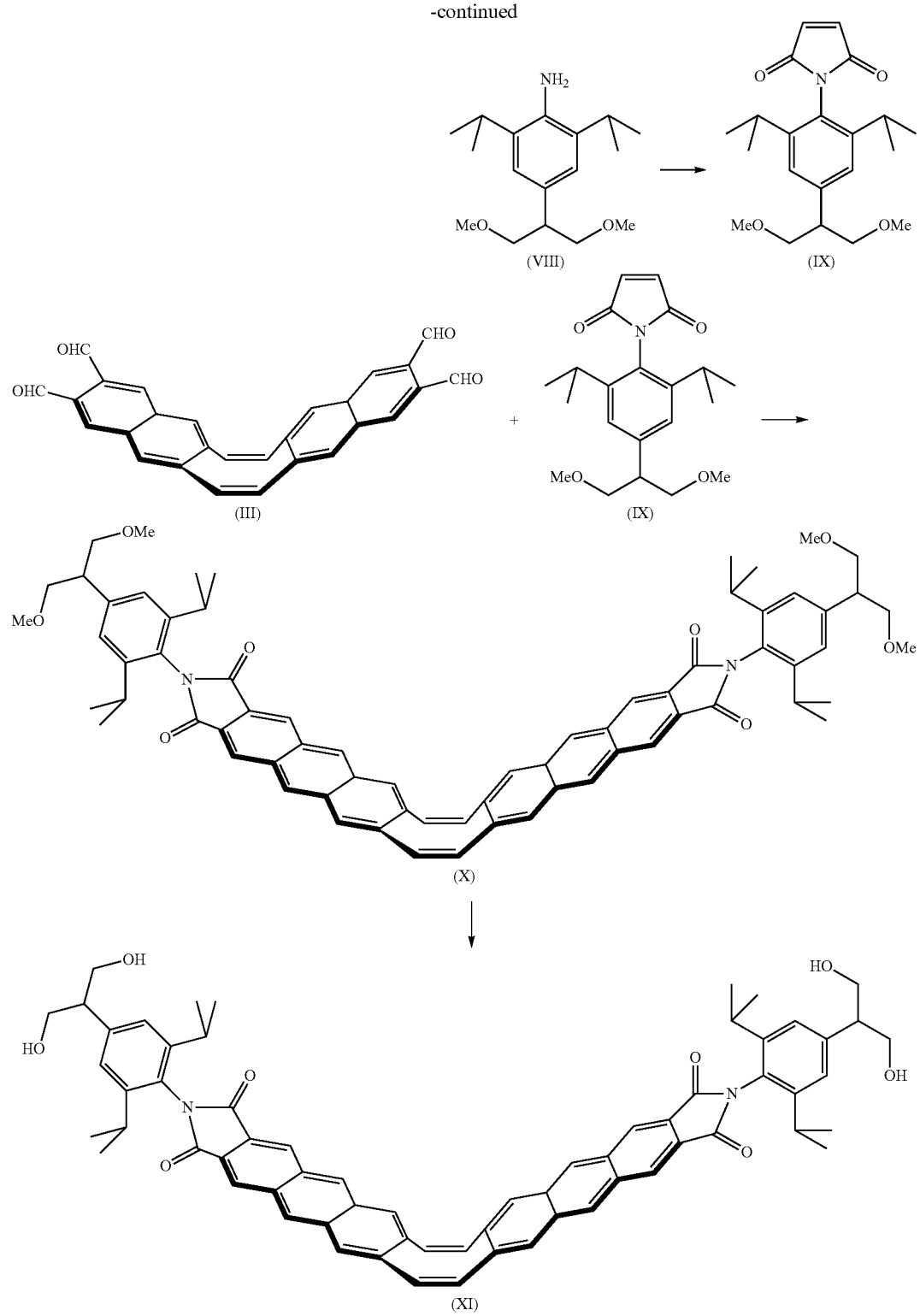

Synthesis of 2-(4-amino-3,5-diisopropylphenyl) malonic acid diethyl (Compound (VI))

Under an argon atmosphere, 4-iodo-2,6-diisopropylaniline (synthesized in accordance with a method described in Dalton Transaction, 2012, 41, p 6803-6812, 6.1 g, 20 mmol), copper iodide (290 mg, 1.5 mmol), cesium carbonate (9.8 g, 30 mmol), and 2-phenylphenol (510 mg, 3.0 mmol) were dissolved in tetrahydrofuran (20 mL), diethyl malonate (6.1 mL, 40 mmol) was added, and the mixture was stirred at 70 degrees Celsius for 24 hours. After the reaction solution with added water was diluted with ethyl acetate and washed with a saturated saline solution, the organic layer was passed through anhydrous sodium sulfate for dehydration, and the solvent was distilled away. The crude product was purified by silica gel column chromatography (eluate: methylene chloride), and a compound (VI) was obtained as a brown oily substance (4.0 g, 55%). The spectrum data of the compound (VI) was as follows.

$^1$H NMR (600 MHz, CDCl$_3$) δ (ppm) 7.04. (s, 2H), 4.50 (s, 1H), 4.25-4.16 (m, 4H), 3.75 (s, 2H), 2.90 (sept, J=6.9 Hz, 2H) and 1.28-1.25 (m, 18H); $^{13}$C NMR (150 MHz, CDCl$_3$) δ (ppm) 169.0, 140.4, 132.4, 124.0, 122.6, 61.6, 58.0, 28.2, 22.5 and 14.2.

Synthesis of 2-(4-amino-3,5-diisopropylphenyl) propane-1,3-diol (Compound (VII)

Under an argon atmosphere, a tetrahydrofuran solution (10 mL) of the compound (VI) (1.5 g, 4.2 mmol) was added at 0 degree Celsius to a tetrahydrofuran suspension (10 mL) of lithium aluminum hydride (400 mg, 10 mmol), and the mixture was stirred at room temperature for 4 hours. After a sodium sulfate solution was added, the suspension was filtered to remove aluminum salt, the filtrate was passed through silica gel column (eluate: ethyl acetate), and a crude product was obtained. Recrystallization was performed with a mixture solvent of methylene chloride and hexane, and thereby a compound (VII) was obtained as a white solid (910 mg, 87%). The spectrum data of the compound (VII) was as follows.

$^1$H NMR (600 MHZ, CDCl$_3$) δ (ppm) 6.87 (s, 2H), 3.98-3.94 (m, 2H). 3.91-3.88 (m, 2H), 3.70 (s, 2H), 3.03 (tt, J=7.8, 5.4 Hz, 1H), 2.92 (sept, J=6.6 Hz, 2H), 1.92 (t, J=5.4 Hz, 2H) and 1.26 (d, J=6.6 Hz), 12H); $^{13}$C NMR (150 MHz, CDCl$_3$) δ (ppm) 139.4, 133.0, 128.7, 122.4, 66.5, 49.7, 28.1 and 22.5; HR-APCI TOF-MS (m/z) found 252.1968, calcd for C$_{16}$H$_{25}$NO$_2$: 252.1958 [M+H]$^+$.

Synthesis of 4-(1,3-dimethoxypropanil)-2,6-diisopropylaniline (Compound (VIII))

Under an argon atmosphere, a tetrahydrofuran solution (4.5 mL) of the compound (VI) (900 mg, 3.6 mmol) was added at 0 degree Celsius to sodium hydrogenide (60%, dispersed in fluid paraffin, 400 mg, 10 mmol) and tetrahydrofuran suspension (9.0 mL) of methyl iodide (450 µL, 7.2 mmol), and the mixture was stirred at room temperature for 1 hour. After the reaction solution was diluted by ethyl acetate (20 mL), the solvent was distilled away, and a crude product was obtained. The crude product was purified by silica gel column chromatography (eluate: methylene chloride/hexane/ether=1/1/1), a compound (VIII) was obtained as a brown oily substance (930 mg, 93%). The spectrum data of the compound (VIII) was as follows.

$^1$H NMR (600 MHZ, CDCl$_3$) δ (ppm) 6.92 (s, 2H), 3.63 (dd, J=9.2, 6.8 Hz, 2H), 3.57 (dd, J=9.7, 6.4 Hz, 2H), 3.39 (s, 6H), 3.06 (tt, J=9.2, 6.4 Hz, 1H), 2.91 (sept, J=6.9 Hz, 2H), and 1.27 (d, J=6.9 Hz, 12H); $^{13}$C NMR (150 MHz, CDCl$_3$) δ (ppm) 139.1, 132.4, 130.5, 122.4, 74.5, 59.0, 45.8, 28.1 and 22.5; HR-APCITOF-MS (m/z) found 280.2271, calcd for C$_{17}$H$_{29}$NO$_2$: 280.2271 [M+H]$^+$.

Synthesis of N-(4-(1,3-dimethoxypropanil)-2,6-diisopropylphenyl)-maleimide (Compound (IX))

Under an argon atmosphere, the compound (VIII) (1.0 g, 3.7 mmol) and maleic anhydride (720 mg, 7.4 mmol) were dissolved in acetic acid (2.2 mL), which was stirred at room temperature for 10 hours. Then, sulfuric acid (95%, 370 µL) and acetic anhydride (180 µL) were added to the reaction solution, which was heated to 60 degrees Celsius and stirred for 10 hours. After the reaction solution with added water was diluted with ethyl acetate, and washed with a saturated saline solution, the organic layer was passed through anhydrous sodium sulfate for dehydration, and the solvent was distilled away. The crude product was purified by silica gel column chromatography (eluate: methylene chloride/ether=6/1), and a compound (IX) was obtained as a white solid (1.1 g, 80%). The spectrum data of the compound (IX) was as follows.

$^1$H NMR (600 MHz, CDCl$_3$) δ (ppm) 7.12 (s, 2H), 6.88 (s, 2H), 3.67-3.64 (m, 2H), 3.63-3.60 (m, 2H), 3.35 (s, 6H), 3.13 (tt, J=7.2, 6.0 Hz, 1H). 2.59 (sept, J=6.9 Hz, 2H) and 1.15 (d, J=6.9 Hz, 12H); H$_3$C NMR (150 MHz, CDCl$_3$) δ (ppm) 170.8, 147.2, 142.9, 134.4, 124.5, 124.0, 74.0, 59.0, 46.4, 29.4, and 24.1; HR-APCI TOF-MS (m/z) found 359.2096, calcd for C$_{21}$H$_{29}$NO$_4$: 359.2097 [M+H]$^+$.

<Synthesis of Compound (X)>

Under an argon atmosphere, the compound (IX) (680 mg, 1.90 mmol) was dissolved in 1,2-dichloroethane (30 mL), tributylphosphine (510 µL, 2.1 mmol) was added at 0 degree Celsius, and the mixture was stirred at room temperature for 30 minutes. Then, a 1,2-dichloroethane solution (15 mL) of the compound (III) (330 mg, 0.79 mmol) was added to the reaction solution at 0 degree Celsius, diazabicycloundecene (24 µL, 0.16 mmol) was added, and the mixture was stirred at 80 degrees Celsius for 12 hours. The reaction solution with added water was divided by a saturated saline solution, the organic layer was passed through anhydrous sodium sulfate for dehydration, the solvent was distilled away, and a crude product was obtained. The crude product was purified by silica gel column chromatography (eluate: methylene chloride/ether=5/1), and a compound (X) was obtained as a yellow solid (208 mg, 25%). The spectrum data of the compound (X) was as follows.

$^1$H NMR (600 MHz, CDCl$_3$) δ (ppm) 8.55 (s, 4H+4H), 7.94 (s, 4H), 7.24 (s, 4H), 7.16 (s, 4H), 3.70-3.67 (m, 4H), 3.66-3.63 (m, 4H), 3.37 (s, 12H), 3.16 (tt, J=7.2, 6.0 Hz, 2H), 2.72 (sept, J=6.8 Hz, 4H) and 1.15 (d, J=6.8 Hz, 24H); $^{13}$C NMR (150 MHz, CDCl$_3$) δ (ppm) 167.9, 146.7, 142.8, 136.6, 133.4, 132.4, 132.2, 129.8, 128.4, 126.64, 126.59, 125.9, 123.8, 76.9, 59.1, 46.4, 29.5, and 24.0.

<Synthesis of Compound (XI)>

Under an argon atmosphere, the compound (X) (170 mg, 0.16 mmol) was dissolved in methylene chloride (12 mL), a methylene chloride solution of boron tribromide (1.0 M, 2.48 mL) was added at −78 degrees Celsius, and the mixture was stirred for 4 hours while gradually heated back to room temperature. The reaction solution with added water was divided by a saturated saline solution, the organic layer was passed through anhydrous sodium sulfate for dehydration, the solvent was distilled away, and a crude product was obtained. The crude product was purified by silica gel column chromatography (eluate: ether), and a compound (XI) was obtained as a yellow solid (21 mg, 13%). The spectrum data of the compound (XI) was as follows.

$^1$H NMR (800 MHZ, CDCl$_3$) δ (ppm) 8.55 (m, 8H), 7.94 (s, 4H), 7.24 (s, 4H), 7.16 (s, 4H), 8.70-3.67 (m, 4H), 3.66-3.68 (m, 4H), 3.37 (s, 12H). 3.16 (tt, J=7.2, 6.0 Hz, 2H), 2.72 (sept, J=6.8 Hz, 4H) and 1.15 (d, J=6.8 Hz, 24H); $^{13}$C NMR (160 MHZ, CDCl$_3$) δ (ppm) 167.9, 146.7, 142.8, 186.6, 133.4, 132.4, 182.2, 128.8, 128.4, 126.64, 126.59, 125.9, 123.8, 76.9, 59.1, 46.4, 29.5, and 24.0.

Example 3
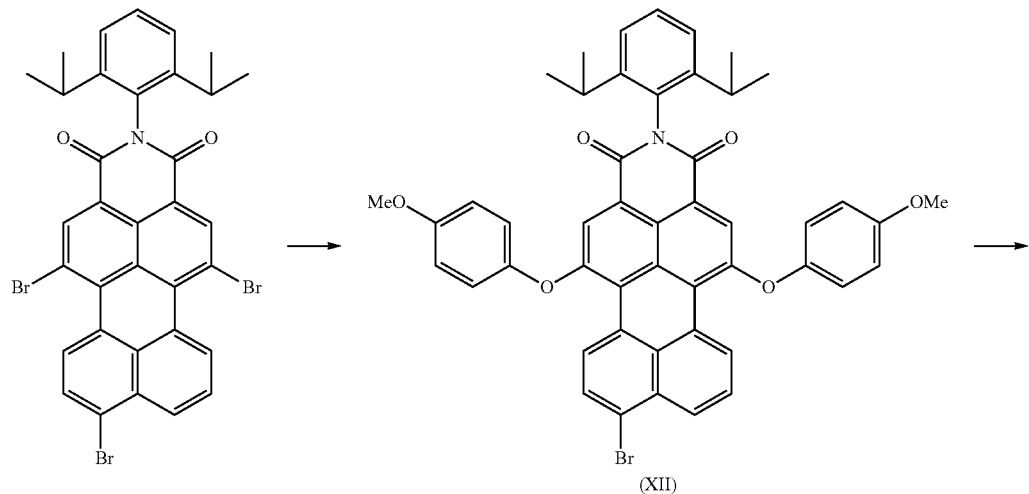
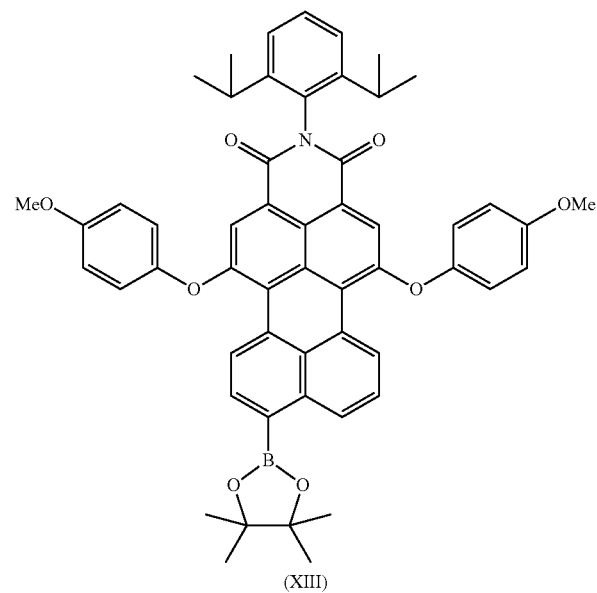
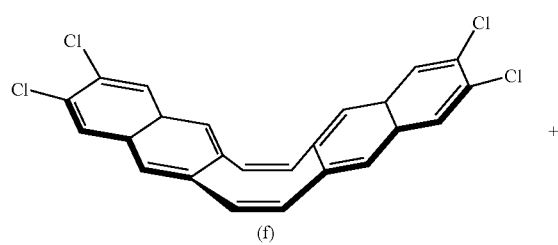

-continued
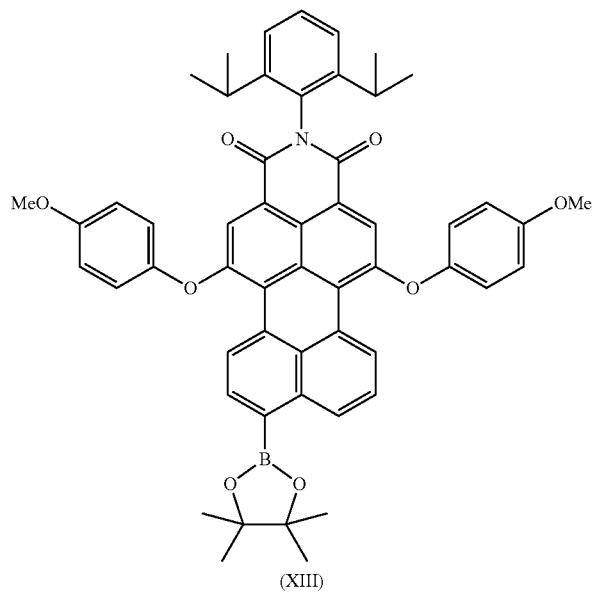
(XIII)
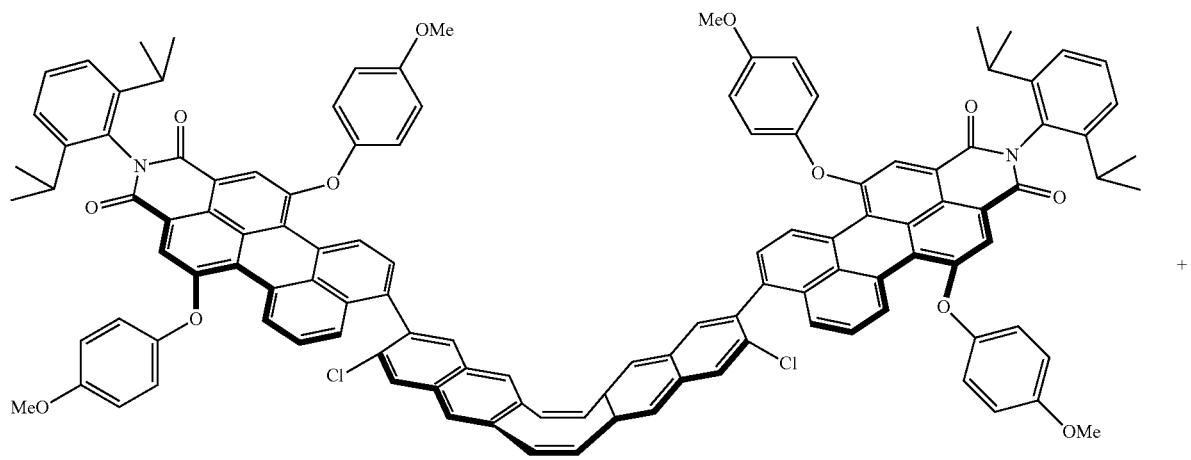
+
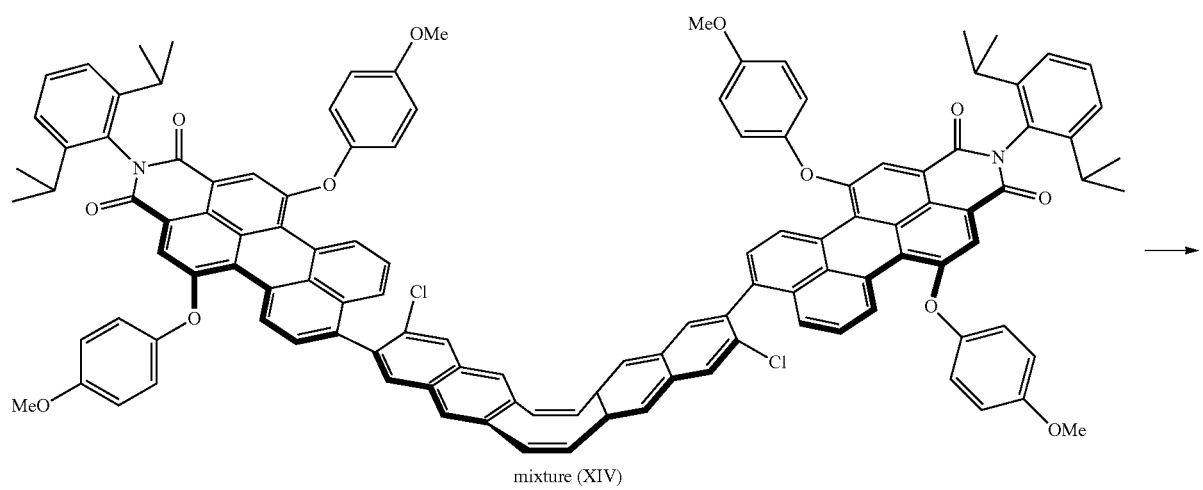
mixture (XIV)

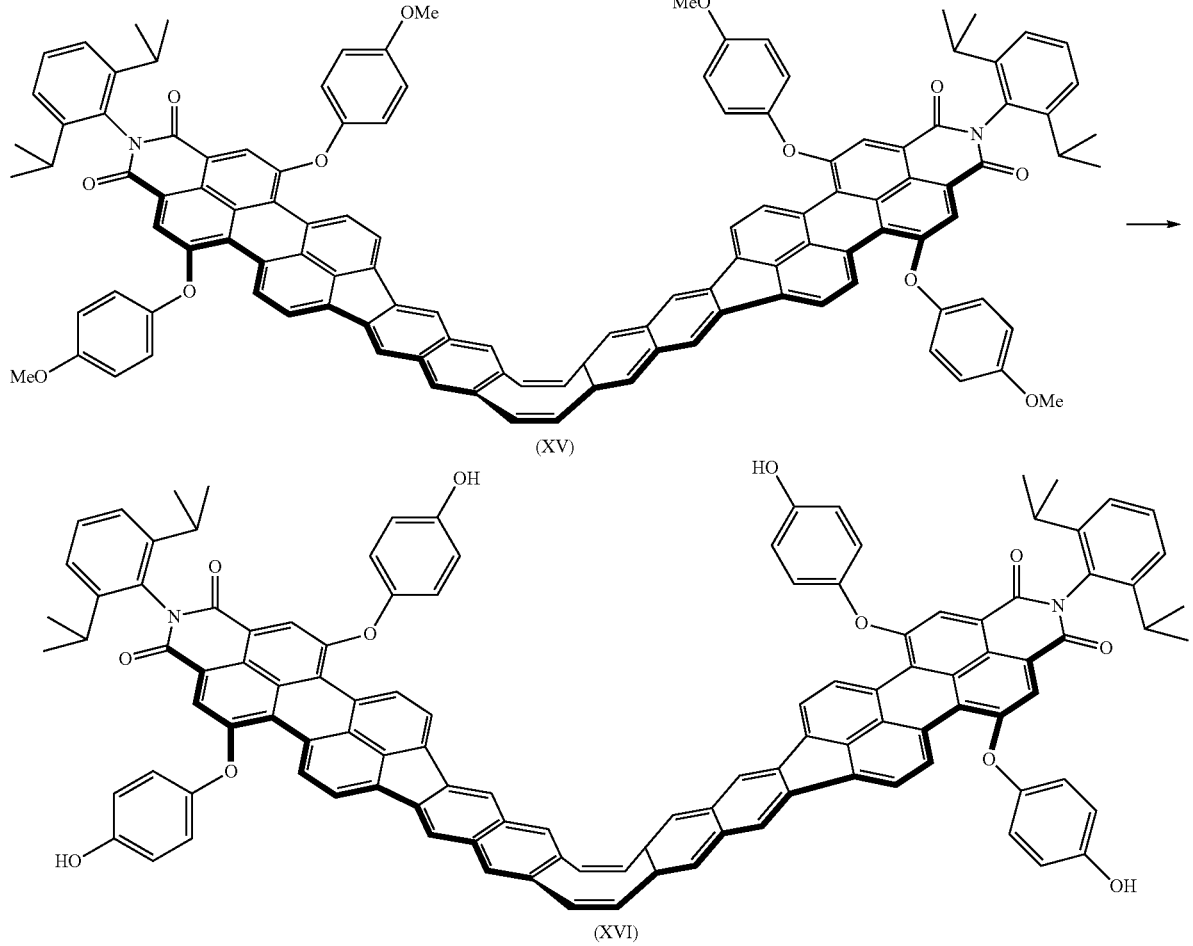

(XV)

(XVI)

Synthesis of N-(2,6-diisopropylphenyl)-1,6-bis(4-methoxyphenoxy)-9-bromoperilene-3,4-dicarboxymide (Compound (XII))

N-(2,6-diisopropylphenyl)-1,6,9-tribromoperylene-3,4-dicarboxymide (synthesized in accordance with a method described in Journal of Materials Chemistry, 1998, 8, p 2357-2369, 0.50 g, 0.70 mmol), potassium carbonate ($K_2CO_3$; 0.21 g, 1.5 mmol), 4-methoxyphenol (0.16 g, 1.3 mmol) were put in a Schlenk, dissolved in N-methyl-2-pyrrolidone (15 mL), and stirred at 80 degrees Celsius for 3.5 hours under a nitrogen atmosphere. The reaction liquid was cooled back to room temperature and added to a mixture liquid of concentrated hydrochloric acid (15 mL) and water (30 mL). The deposited precipitation was filtered and dried and then purified by silica gel column chromatography (eluate: hexane/dichloromethane=1/2, v/v), and thereby a compound (XII) was obtained as a red solid (0.18 g, 31%). The spectrum data of the compound (XII) was as follows.

$^1$H NMR (CDCl$_3$, 600 MHz): δ 9.40 (dd, J=7.8 Hz, J=0.9 Hz, 1H), 9.17 (d, J=8.4 Hz, 1H), 8.35 (dd, J=7.8 Hz, J=0.9 Hz 1H), 8.25 (s, 1H), 8.24 (s, 1H), 7.90 (d, J=8.4 Hz, 1H), 7.71 (t, J=8.4 Hz, 1H), 7.43 (t, J=7.8 Hz, 1H), 7.28 (d, J=8.4 Hz, 1H), 7.10-7.07 (m, 4H), 6.95-6.93 (m, 4H), 3.82 (s, 6H), 2.70-2.67 (m, 2H), 1.12 (d, J=6.8 Hz 12H); $^{13}$C NMR (CDCl$_3$, 150 MHz): δ 163.26, 163.24, 156.76, 156.74, 154.68, 154.60, 149.15, 149.07, 145.78, 132.18, 131.65, 131.14, 131.08, 130.81, 129.55, 129.43, 129.40, 128.80, 128.28, 127.96, 127.78, 126.24, 126.12, 125.43, 124.03, 123.70, 123.59, 122.78, 122.03, 122.00, 120.56, 120.54, 115.62, 55.88, 29.23, 24.14.

<Synthesis of Compound (XIII)>

N-(2,6-diisopropylphenyl)-1,6-bis(4-methoxyphenoxy)-9-bromoperylene-3,4-dicarboxymide (0.18 g, 0.22 mmol), bispinacolate diborone ((BPin) 2; 90 mg, 0.35 mmol), potassium acetate (70 mg, 0.67 mmol), and [1,1'-bis(diphenylphosphino)ferrocene] palladium (II) dichloride (PdCl2 (dppf); 10 mg, 13 μmol) were dried in vacuum in a Schlenk, 1,4-dioxane (7 mL) was added and then frozen and dehydrated. Then, stirring was performed at 70 degrees. Celsius for 24 hours under a nitrogen atmosphere. The reaction solution was allowed to be cooled to be at room temperature, and the solvent was distilled away. The residue was purified by silica gel column chromatography (eluate: hexane/dichloromethane=1/2, v/v), and thereby a compound (XIII) was obtained as a red solid (0.15 g, 82%). The spectrum data of the compound (XIII) was as follows.

$^1$H NMR (CDCl$_3$, 600 MHz): δ 9.36 (d, J=7.8 Hz, 1H), 9.32 (d, J=8.4 Hz, 1H), 8.92 (d, J=8.4 Hz, 1H), 8.300 (s, 1H), 8.298 (s, 1H), 8.22 (J=7.8 Hz, 1H), 7.67 (t, J=8.4 Hz, 1H), 7.45 (t, J=7.8 Hz, 1H), 7.30 (d, J=7.8 Hz, 2H), 7.10-7.07 (m, 4H), 6.94-6.92 (m, 4H), 3.82 (s, 6H), 2.75-2.72 (m, 2H), 1.46 (s, 12H), 1.16 (d, J=6.8 Hz-12H); $^{13}$C NMR (CDCl$_3$, 150 MHz): δ 163.30, 156.48, 156.45, 154.50, 154.21, 149.41, 145.78, 137.19, 136.18, 131.95, 131.14, 130.90, 130.26, 129.48, 129.28, 128.68, 127.72, 127.59, 127.45, 127.09, 127.02, 124.08, 124.02, 123.98, 123.00, 121.97, 121.39, 120.33, 120.13, 115.48, 84.19, 55.82, 29.18, 25.08, 24.12.

<Synthesis of Compound (XV)>

The compound (XIII) (0.15 g, 0.18 mmol), the compound (f) (34 mg, 0.078 mmol), palladium (II) acetate (1.9 mg, 8.4 µmol), 2-cyclohexylphosphino-2',4',6'-triisopropyl biphenyl (XPhos; 7.8 mg, 16 µmol), tripotassium phosphate ($K_3PO_4$; 84 mg, 0.40 mmol), and water (25 µL) were dissolved in tetrahydrofuran (6.0 mL) in a Schlenk and frozen and dehydrated. Then, stirring was performed at 60 degrees Celsius overnight under a nitrogen atmosphere. The reaction solution was allowed to be cooled to be at room temperature, and the solvent was distilled away. The residue was purified by silica gel column chromatography (eluate: dichloromethane), and thereby an isomeric mixture (XIV) was obtained as a red solid crude product.

The obtained isomeric mixture (XIV) and $PdCl_2(PCy_3)_2$ (11 mg, 15 µmol) were dried in vacuum in the Schlenk. 1,8-diazabicyclo[5.4.0]-7-undecene (53 µL, 0.35 mmol) and dimethylacetamide (2.7 mL) were added and dehydrated in vacuum. The reaction liquid was stirred at 140 degrees Celsius for 22 hours under a nitrogen atmosphere. The reaction liquid was allowed to be cooled to room temperature, methanol (20 mL) was then added, and the deposited precipitation was filtered. After the obtained precipitation was purified by silica gel column chromatography (eluate: dichloromethane) and recycle HPLC (eluate: chloroform), reprecipitation was further performed with a chloroform/methanol mixture solvent, a filtered solid was washed with chloroform, and thereby a compound (XV) was obtained as a blue solid (2.2 mg, 1.6%). The spectrum data of the compound (XV) was as follows.

$^1$H NMR ($CDCl_3$, 600 MHz): δ 9.52 (d, J=8.4 Hz, 4H), 8.26 (s, 4H), 8.17 (s, 4H), 8.05 (d, J=8.4 Hz, 4H), 7.71 (s, 4H), 7.42 (d, J=8.4 Hz, 2H), 7.27 (d, J=7.8 Hz, 4H), 7.13-7.11 (m, 12H), 6.94 (d, J=9.0 Hz, 8H), 3.82, (s, 12H), 2.70-2.67 (m, 4H), 1.11 (d, J=6.8 Hz. 24H).

<Synthesis of Compound (XVI)>

The compound (XV) (5.0 mg, 2.8 µmol) was dissolved in dehydrated dichloromethane (2.5 mL), methylene chloride solution of boron tribromide (1 M, 0.10 mL; 0.10 mmol) was added under a nitrogen atmosphere, and the mixture was stirred at room temperature for 2 hours. After methylene chloride was evaporated by nitrogen flow, methanol (2.5 mL) and water (2.5 mL) were added. The obtained suspension was heated for 1 minute and then allowed to be cooled, filtered out by using water, and dried in vacuum, and thereby a compound (XVI) was obtained as a violet solid (4.3 mg, 90%). The spectrum data of the compound (XVI) was as follows.

$^1$H NMR (DMSO-$d_6$, at 120° C., 600 MHz): δ 9.52-9.51 (m, 4H), 9.11 (br, 4H), 8.42 (br, 4H), 8.29-8.28 (m, 4H), 8.10 (br, 4H), 7.84 (br, 4H). 7.43-7.39 (m, 2H), 7.29-7.27 (m, 4H), 7.15-7.13 (m, 12H), 6.91-6.89 (m, 8H), 2.67-2.65 (m, 4H), 1.06-1.04 (m, 24H).

Example 4

[Synthesis of Polymer Film in which FLAP is Put in Cross-Linkage Point of Polyurethane]

After a small amount of the compound (XVI) synthesized in Example 3 and polytetrahydrofuran (Mn up to 650, 2.09 g) were dried in vacuum in a flask and dissolved while adding 4.1 mL of dehydrated dimethylformamide. Furthermore, after hexamethylene diisocyanate (0.78 mg, 4.86 mmol) and triethanolamine (0.15 mL, 148 mg, 1.12 mmol) were added and stirred, dibutyltin di-laurate (7 drops) was added, and the mixture was stirred at room temperature for 5 minutes. The obtained viscous liquid mixture was poured into a polytetrafluoroethylene mold shaped in a film test piece, left at room temperature for 2 days to develop a polymerization reaction under a nitrogen atmosphere. The mold was then dried in vacuum overnight to fabricate film-like polyurethane. The film test piece with the mold was immersed and washed in a 1,4-dioxane solvent for 1 day, the film test piece removed from the mold was taken out from the solvent and again dried in vacuum overnight, and thereby a red light-emitting FLAP cross-linkage polyurethane film was obtained.

[Confirmation of Optical Stability]

Example 5

In experiments for optical stability, the compound (k) was dissolved in an undehydrated dichloromethane solvent to obtain a solution with the initial concentration of 24 µM. This solution was put in 1 cm square quartz cell for fluorescence measurement, and a lid was put thereon.

Next, a UV-LED having a wavelength of 365 nm is fixed at a place apart by 10 cm from the quartz cell, and a solution in the quartz cell was continuously irradiated with UV light (irradiation intensity: 40 mW/cm$^2$) while being stirred. The fluorescence spectrum was measured every 10 minutes (excitation wavelength: 365 nm), and the rate of fluorescence attenuation due to photodegradation was measured. The measurement result was illustrated in FIG. 5.

Comparative Example 1

The fluorescence spectrum was measured by the same method as in Example 5 except that a cyclooctatetraene condensed-ring anthracene imide dimer ("compound 3d" described in Chem. Eur. J. 2014, 20, 2193-2200. See FIG. 5 for the structure) was in a dichloromethane solution with the initial concentration of 12 µM. FIG. 5 illustrates the result.

As illustrated in FIG. 5, while the fluorescence intensity was significantly attenuated by two-hour UV irradiation in Comparative example 1, a high fluorescence intensity was still maintained in Example 5. It was revealed from the above results that the novel FLAP according to the embodiment improved optical stability compared to the conventional compound.

Example 6

Figure 6:
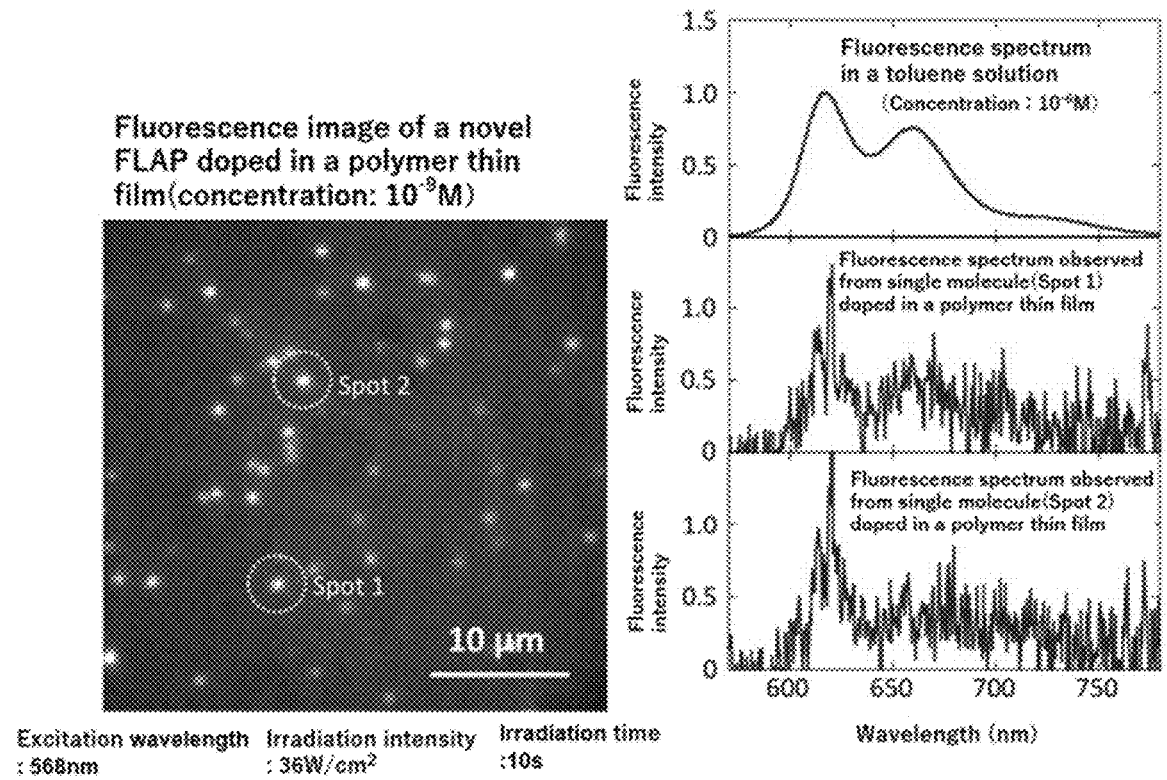
FIG. 6 is a graph illustrating a result of fluorescence attenuation measured in Example 6.

Instead of the experiment using the solvent of Example 5, the compound (k) was doped in a polymer thin film (Zeonex, film thickness: around 100 nm) at a low concentration of 1 nM to 100 nM, and the rate of attenuation of fluorescence when irradiated with light at an intensity of 36 W/cm$^2$ was measured. FIG. 6 illustrates the result.

Comparative Example 2

Figure 7:
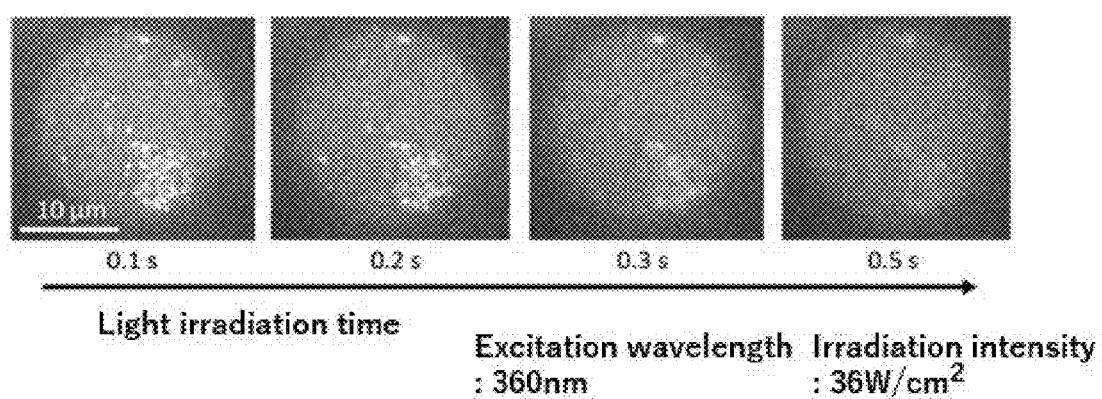
FIG. 7 is a graph illustrating a result of fluorescence attenuation measured in Comparative example 2.

Evaluation was made by the same method as that in Example 6 except that a cyclooctatetraene condensed-ring anthracene imide dimer (the compound A1 of Example 1 in Patent Literature 3 described above) was used instead of the compound (k). FIG. 7 illustrates the result.

First, in Comparative example 2, after light irradiation is started at an intensity of 36 W/cm$^2$, substantially all the bright spots disappeared in 0.5 seconds, as illustrated in FIG. 7. On the other hand, in Example 6, clear bright spots were observed even after 10-second irradiation, as illustrated in FIG. 6. Furthermore, a fluorescence spectrum at each bright spot was measured, it was found that the shape thereof matched that of the fluorescence spectrum in the toluene solution, and this revealed that sufficient optical stability and fluorescence quantum yield for single-molecule fluorescence imaging were provided.

Example of Synthesis of Intermediate Used for Manufacturing FLAP Precursor

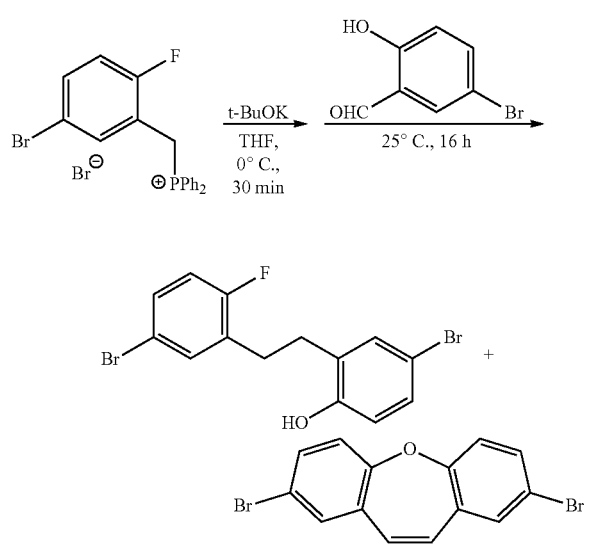

After t-BuOK (423 mg, 3.77 mmol) was added to a THF solution of (5-bromo-2-fluorobenzyl)triphenylphosphonium bromide (2.0 g, 3.77 mmol) and the mixture was stirred at 0 degree Celsius for 30 minutes, 5-bromo-2-hydroxybenzaldehyde (51.7 mg, 1.72 mmol) was added, and the mixture was stirred at 25 degrees Celsius for 16 hours. After dilute hydrochloride acid was added to the reaction solution to stop the reaction, the organic layer divided by using dichloromethane was extracted to distill the solvent. The residue was purified by silica gel column chromatography by using dichloromethane/hexane (1:1 by volume) as a developing solvent. As a result, in addition to the primary product (E)-4-bromo-2-(5-bromo-2-fluorostyryl) phenol (430 mg, yield 66%), the intended 2,8-dibromodibenzo[b, f]oxepine having a seven-membered ring structure was obtained (110 mg, yield 18%). The spectrum data was as follows.

$^1$H NMR: δ/ppm (in heavy chloroform) 7.39 (dd, J=8.7, 2.3 Hz, 2H), 7.29 (d, J=2.3 Hz, 2H), 7.02 (d, J=8.7 Hz, 2H), 6.63 (s, 2H). $^{13}$C NMR: δ/ppm (in heavy chloroform) 156.26, 132.92, 132.15, 132.08, 130.04, 123.10, 118.04.

Note that the spectrum data of the compound of (E)-4-bromo-2-(5-bromo-2-fluorostyryl) phenol was as follows.

$^1$H NMR: δ/ppm (in heavy chloroform) 7.74 (dd, J=6.6, 2.4 Hz, 1H), 7.69 (d, J=2.4 Hz, 1H), 7.34 (d, J=16.5 Hz, 1H), 7.34 (ddd, J=4.4, 4.2, 2.4 Hz, 1H), 7.26 (dd, J=8.4, 2.4 Hz, 1H), 7.18 (d, J=16.5 Hz, 1H), 6.97 (dd, J=9.9, 8.4 Hz, 1H), 6.71 (d, J=7.8 Hz, 1H), 4.92 (s, 1H).

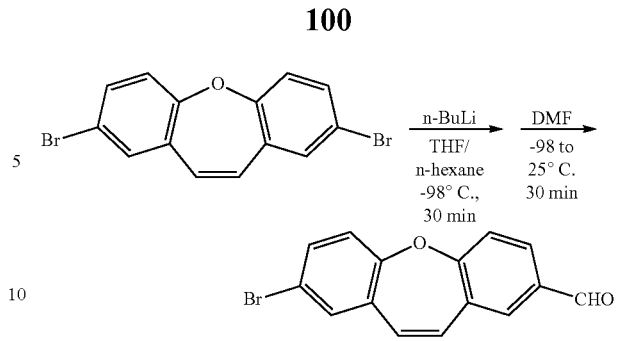

After a THF solution of 2,8-dibromodibenzo [b, f] oxepine (100 mg, 0.284 mmol) was cooled to −98 degrees Celsius, an n-hexane solution (0.18 mol/L, 1.6 mL, 0.29 mmol) of n-BuLi was added, and the mixture was stirred at −98 degrees Celsius for 30 minutes, dimethylformamide (0.22 mL, 2.8 mmol) was added, and the temperature was increased up to 25 degrees Celsius in 30 minutes. After water was added to the reaction solution to stop the reaction, the organic layer divided by using dichloromethane was extracted, and the solvent was distilled away. The residue was purified by silica gel column chromatography by using dichloromethane/hexane (4:1 by volume) as a developing solvent. As a result, 8-bromodibenzo[b, f]oxepine-2-carbaldehyde was obtained (75.7 mg, yield 88%). The spectrum data was as follows.

$^1$H NMR: (in heavy chloroform) δ/ppm 9.94 (s, 1H), 7.83 (dd, J=8.4, 1.8 Hz, 1H), 7.69 (d, J=2.4 Hz, 1H), 7.41 (dd, J=8.4, 2.4 Hz, 1H), 7.30 (d, J=1.8 Hz, 1H), 7.28 (d, J=8.4 Hz, 1H), 7.05 (d, J=8.4 Hz, 1H), 6.75 (d, J=11.5 Hz, 1H), 6.66 (d, J=11.5 Hz, 1H). $^{13}$C NMR: δ/ppm (in heavy chloroform) 190.76, 162.01, 155.83, 133.80, 133.09, 132.22, 132.10, 131.81, 131.36, 131.05, 130.38, 130.13, 123.29, 122.47, 118.41.

It is possible to synthesize dibenzo[b, f]oxepine-2,8-dicarbaldehyde by using two equivalent amount of n-BuLi to activate DMF in the same manner as the above reaction. Furthermore, by activating NaBH$_4$ to reduce and transform aldehyde into alcohol, it is possible to obtain dibenzo[b, f]oxepine-2,8-diyldimethanol having a hydroxy group that is a polymerizable group. Further, it is possible to synthesize (10-methyldibenzo[b,f]oxepine-2,8-diyl)dimethanol in which a methyl group is introduced to the center seven-membered ring by applying the same chemical transformation as in the case of a FLAP having the center eight-membered ring structure. An intermediate used for manufacturing a FLAP precursor is obtained in such a way. Next, a substituent group used for forming a substructure that inhibits aggregation and, if necessary, a substituent group used for forming a substructure having a polymerizability are introduced to the intermediate, and thereby the FLAP precursor is obtained. Note that the method of obtaining polyurethane from a monomer having hydroxy groups at both terminals is in accordance with the case of the FLAP having the center eight-membered ring structure.

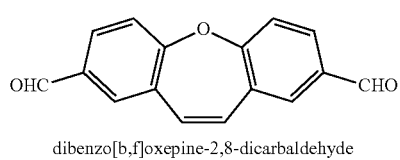

dibenzo[b,f]oxepine-2,8-dicarbaldehyde

-continued

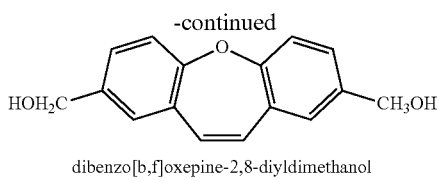
dibenzo[b,f]oxepine-2,8-diyldimethanol

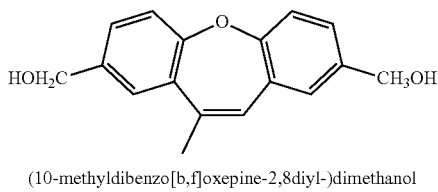
(10-methyldibenzo[b,f]oxepine-2,8diyl-)dimethanol

Furthermore, as the method for introducing a polymerizable group, another method below may be employed.

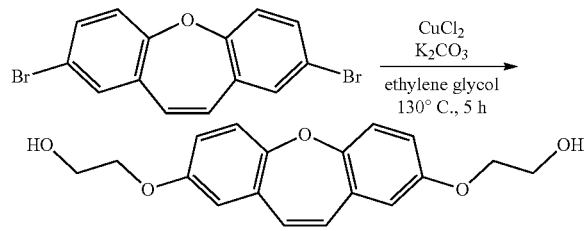

After an ethylene glycol solution (1.0 mL) of 2,8-dibromodibenzo[b, f]oxepine (78.0 mg, 0.221 mmol), copper (II) chloride (1.5 mg, 0.011 mmol), and potassium carbonate (91.2 mg, 0.659 mmol) was stirred at 130 degrees Celsius for 5 hours, water was added to the reaction solution to stop the reaction, the organic layer divided by using dichloromethane was extracted, and the solvent was distilled away. The residue was purified by silica gel column chromatography by using dichloromethane/ethyl acetate (1:1 by volume) as a developing solvent. As a result, 2,2'-(dibenzo[b, f]oxepine-2,8-diylbis(oxy))bis(ethan-1-ol) was obtained (30.0 mg, yield 43%). The spectrum data was as follows.

$^1$H NMR: (in heavy chloroform) δ/ppm 7.09 (d, J=9.2 Hz, 2H), 6.84 (dd, J=9.2, 2.8 Hz, 2H), 6.70 (d, J=2.8 Hz, 2H), 6.67 (s, 2H), 7.05 (d, J=8.4 Hz, 1H), 6.75 (d, J=11.5 Hz, 1H), 6.66 (d, J=11.5 Hz, 1H), 4.04 (dd, J=4.8, 4.2 Hz, 4H), 3.94 (m, 4H), 1.95 (dd, J=6.6, 6.0 Hz, 2H). $^{13}$C NMR: δ/ppm (in heavy chloroform) 155.64, 151.92, 131.23, 130.43, 122.01, 115.99, 114.77, 69.89, 61.62.

INDUSTRIAL APPLICABILITY

With a use of the compound illustrated in the embodiments, a molecule having higher fluorescence quantum yield and higher optical stability than the conventional FLAP can be obtained. Therefore, the compound and a polymer compound containing the compound can be used as a material for measurement with a viscosity probe or the like.

The invention claimed is:

1. A compound represented by a following general Formula (1):

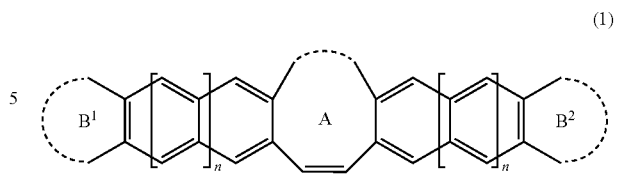

wherein in general Formula (1),
A is represented by general Formula (3) and forms a conjugated system with a benzene ring bound to A:

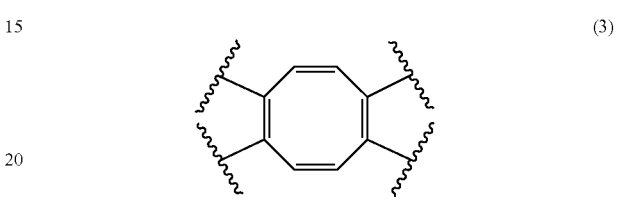

m and n each denote, independently, an integer greater than or equal to 0 and less than or equal to 3,
$B^1$ and $B^2$ each denote, independently, a structure represented by general Formula (5-1), said structure having a —C=C— bond in a 5-member ring of general Formula (5-1) as a position to connect to the remaining of general Formula (1),

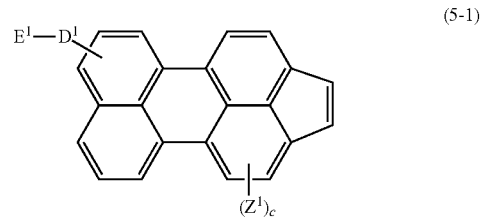

wherein in general Formula (5-1),
$D^1$ denotes a substructure that inhibits aggregation,
$E^1$ denotes a polymerizable substituent group and is any of Formulas (E-1) to (E-19):

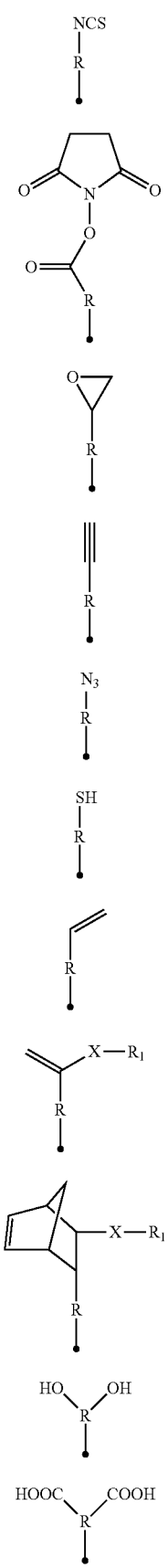

(E-5)

(E-6)

(E-7)

(E-8)

(E-9)

(E-10)

(E-11)

(E-12)

(E-13)

(E-14)

(E-15)

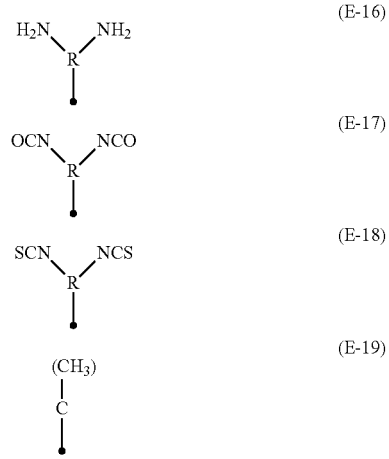

(E-16)

(E-17)

(E-18)

(E-19)

wherein in the Formulas (E-12) and (E-13), X denotes amide or ester but may not be included, $R_1$ in the Formulas (E-12) and (E-13) is H, a linear, branched, or cyclic alkyl group with 1-20 carbons, an aryl group with 6-20 carbons, F, Cl, Br, I, $CF_3$, $CCl_3$, CN, or $OCH_3$, R in Formulas (E-1) to (E-18) denotes a linear, branched, or cyclic alkyl group with 1-20 carbons or an aryl group with 6-20 carbons, R in Formulas (E-1) to (E-11) may not be included, and each filled circle represents $D^1$, $Z^1$ denotes a substituent group selected from a hydrogen atom, a halogen atom, an alkyl group with 1-20 carbons that may have a substituent group, an alkynyl group with 2-20 carbons that may have a substituent group, an aryl group with 6-20 carbons that may have a substituent group, an alkoxy group with 1-10 carbons that may have a substituent group, and a cyano group, and when a plurality of substituent groups $Z^1$ are provided, respective substituent groups may be the same as each other or may be different from each other, c denotes the number of substituent groups $Z^1$.

2. A polymer compound made by polymerizing a compound represented by following general Formula (1):

(1)

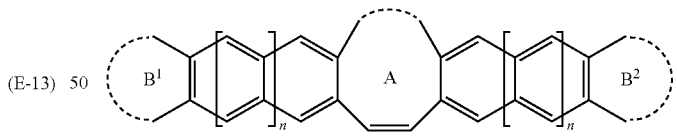

wherein in general Formula (1),

A is represented by general Formula (3) and forms a conjugated system with a benzene ring bound to A:

(3)

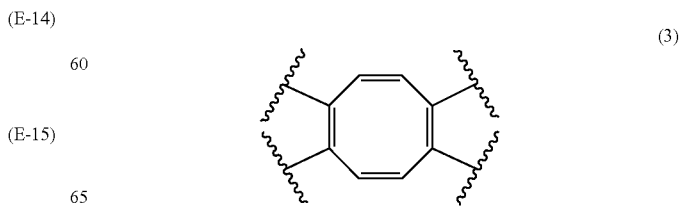

m and n each denote, independently, an integer greater than or equal to 0 and less than or equal to 3, B¹ and B² each denote, independently, a structure represented by general Formula (5-1), said structure having a —C=C— bond in a 5-member ring of general Formula (5-1) as a position to connect to the remaining of general Formula (1),

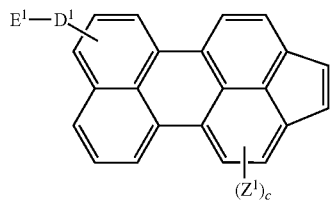

(5-1)

wherein in general Formula (5-1),

D¹ denotes a substructure that inhibits aggregation,

E¹ denotes a polymerizable substituent group and is any of Formulas (E-1) to (E-19):

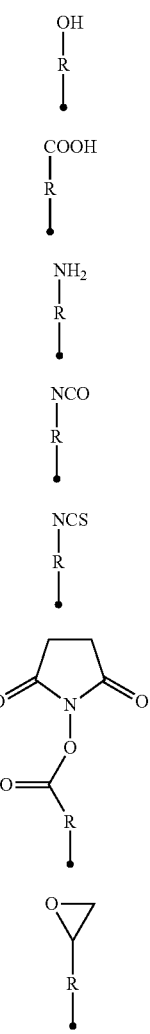

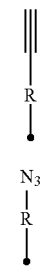

(E-8)

(E-9)

(E-10)

(E-11)

(E-12)

(E-13)

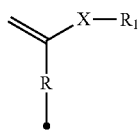

(E-14)

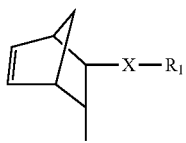

(E-15)

(E-16)

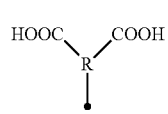

(E-17)

(E-18)

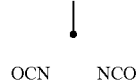

(E-19)

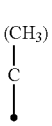

wherein in the Formulas (E-12) and (E-13), X denotes amide or ester but may not be included, $R_1$ in the Formulas (E-12) and (E-13) is H, a linear, branched, or cyclic alkyl group with 1-20 carbons, an aryl group with 6-20 carbons, F, Cl, Br, I, CF, CCl$_3$, CN, or OCH$_3$, R in Formulas (E-1) to (E-18) denotes a linear, branched, or cyclic alkyl group with 1-20 carbons or an aryl group with 6-20 carbons, R in Formulas (E-1) to (E-11) may not be included, and each filled circle represents D$^1$, Z$^1$ denotes a substituent group selected from a hydrogen atom, a halogen atom, an alkyl group with 1-20 carbons that may have a substituent group, an alkynyl group with 2-20 carbons that may have a substituent group, an aryl group with 6-20 carbons that may have a substituent group, an alkoxy group with 1-10 carbons that may have a substituent group, and a cyano group, and when a plurality of substituent groups Z$^1$ are provided, respective substituent groups may be the same as each other or may be different from each other, c denotes the number of substituent groups Z$^1$.

3. The polymer compound according to claim 2, wherein the compound is bound via a urethane binding in the polymer compound.

4. A polymer compound made by polymerizing a compound represented by following general Formula (1):

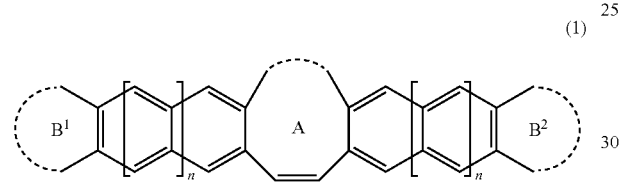
(1)

wherein in general Formula (1),

A is represented by general Formula (3) and forms a conjugated system with a benzene ring bound to A:

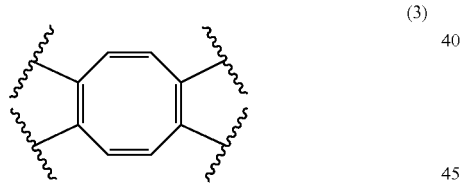
(3)

m and n each denote, independently, an integer greater than or equal to 0 and less than or equal to 3, B1 and B2 each denote, independently, a structure represented by general Formula (5-1), said structure having a —C=C— bond in a 5-member ring of general Formula (5-1) as a position to connect to the remaining of general Formula (1),

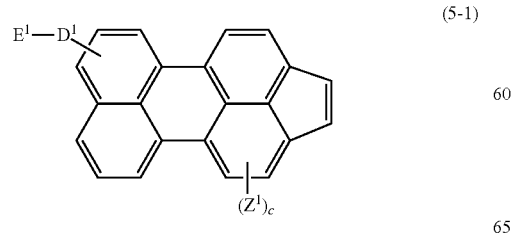
(5-1)

wherein in general Formula (5-1),

D$^1$ denotes a substructure that inhibits aggregation,

E$^1$ denotes a polymerizable substituent group and is any of Formulas (E-1) to (E-19):

(E-1)

(E-2)

(E-3)

(E-4)

(E-5)

(E-6)

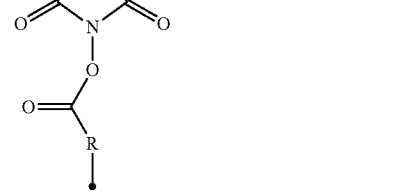
(E-7)

(E-8)

(E-9)

(E-10)

(E-11)

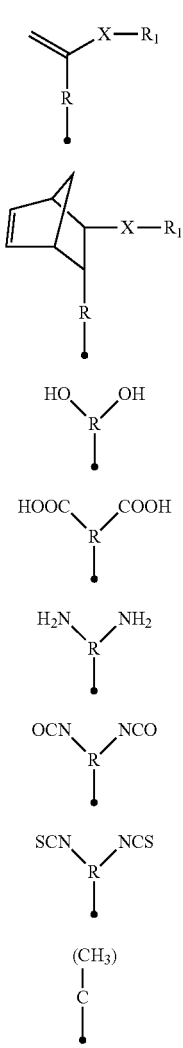

(E-12)
(E-13)
(E-14)
(E-15)
(E-16)
(E-17)
(E-18)
(E-19)

wherein in the Formulas (E-12) and (E-13), X denotes amide or ester but may not be included, $R_1$ in the Formulas (E-12) and (E-13) is H, a linear, branched, or cyclic alkyl group with 1-20 carbons, an aryl group with 6-20 carbons, F, Cl, Br, I, $CF_3$, $CCl_3$, CN, or $OCH_3$, R in Formulas (E-1) to (E-18) denotes a linear, branched, or cyclic alkyl group with 1-20 carbons or an aryl group with 6-20 carbons, R in Formulas (E-1) to (E-11) may not be included, and each filled circle represents $D^1$, $Z^1$ denotes a substituent group selected from a hydrogen atom, a halogen atom, an alkyl group with 1-20 carbons that may have a substituent group, an alkynyl group with 2-20 carbons that may have a substituent group, an aryl group with 6-20 carbons that may have a substituent group, an alkoxy group with 1-10 carbons that may have a substituent group, and a cyano group, and when a plurality of substituent groups $Z^1$ are provided, respective substituent groups may be the same as each other or may be different from each other, c denotes the number of substituent groups $Z^1$, wherein a chemical structure included in the compound is included in a main chain of the polymer compound.

5. The polymer compound according to claim 2, further comprising a cross-linked site made of a chemical structure included in the compound.

6. The polymer compound according to claim 3, further comprising a cross-linked site made of a chemical structure included in the compound.

7. The polymer compound according to claim 4, further comprising a cross-linked site made of a chemical structure included in the compound.

8. A method of forming a polymer comprising polymerization of the compound according to claim 1.

9. A compound which is any selected from the following formulas:

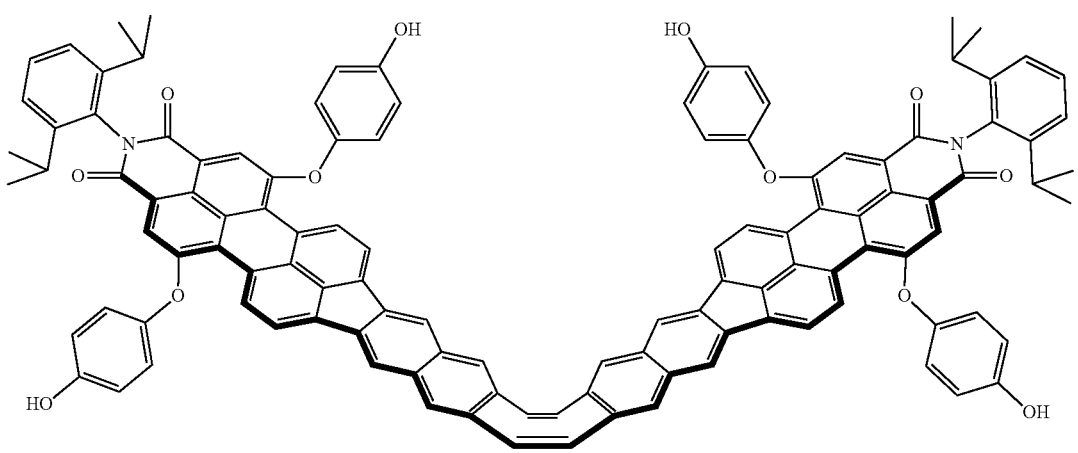

111
112
-continued
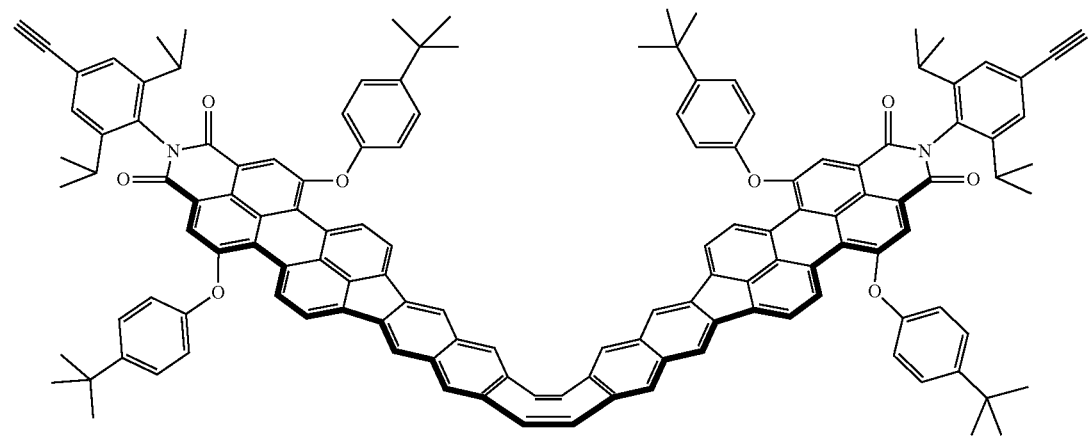
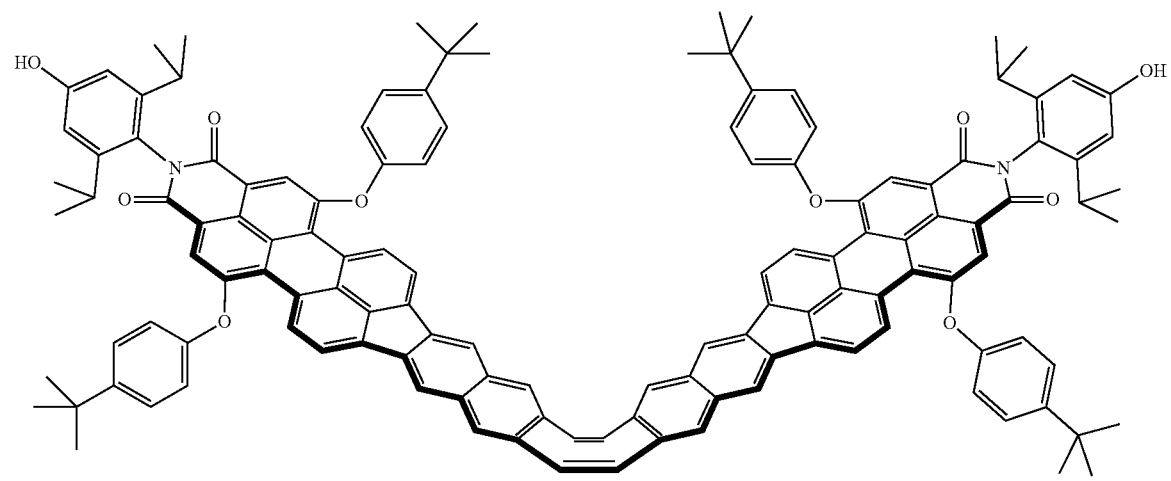
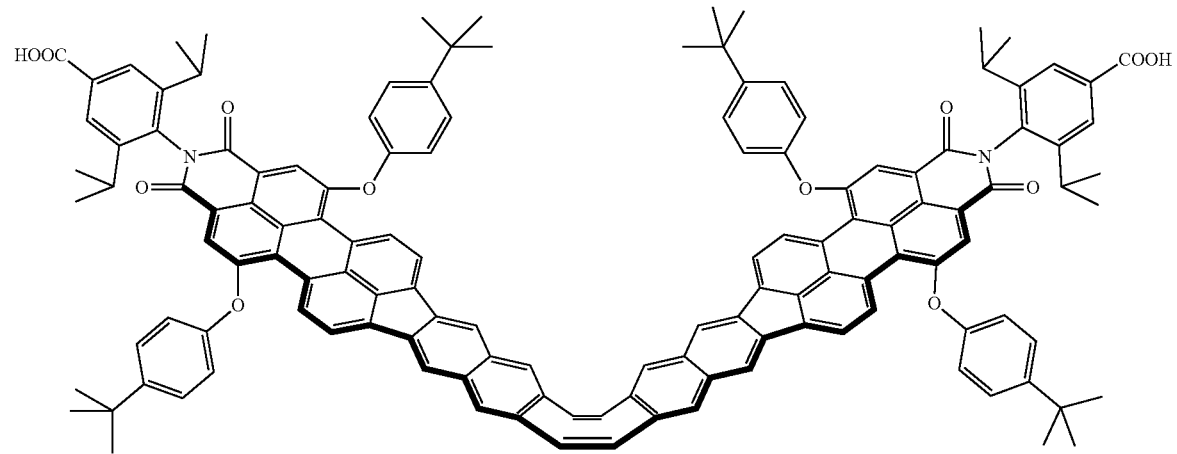

113 114
-continued
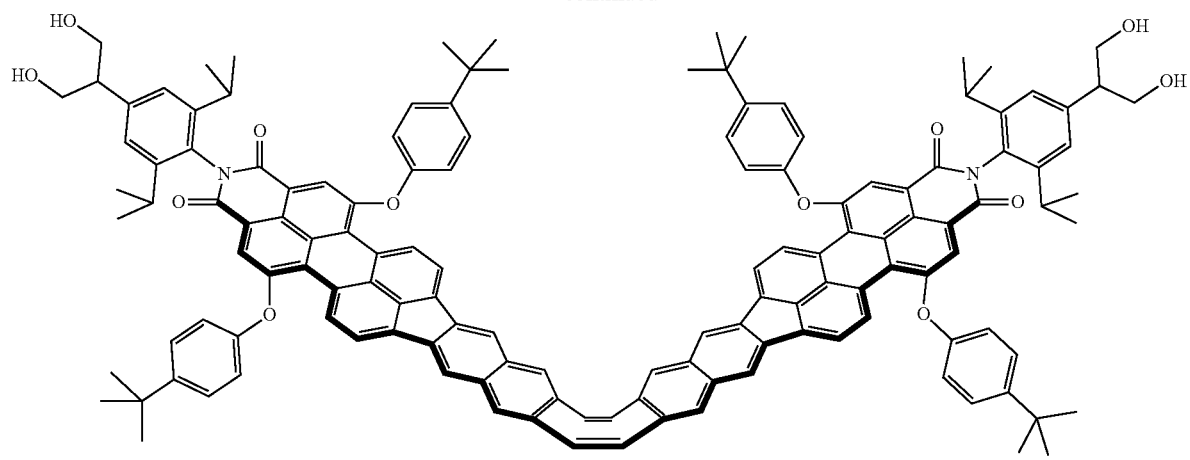
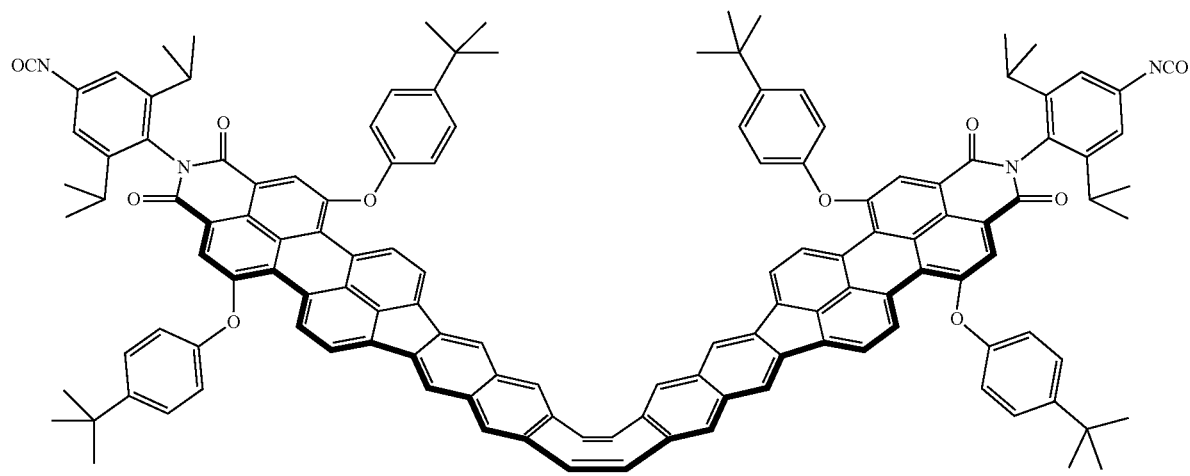
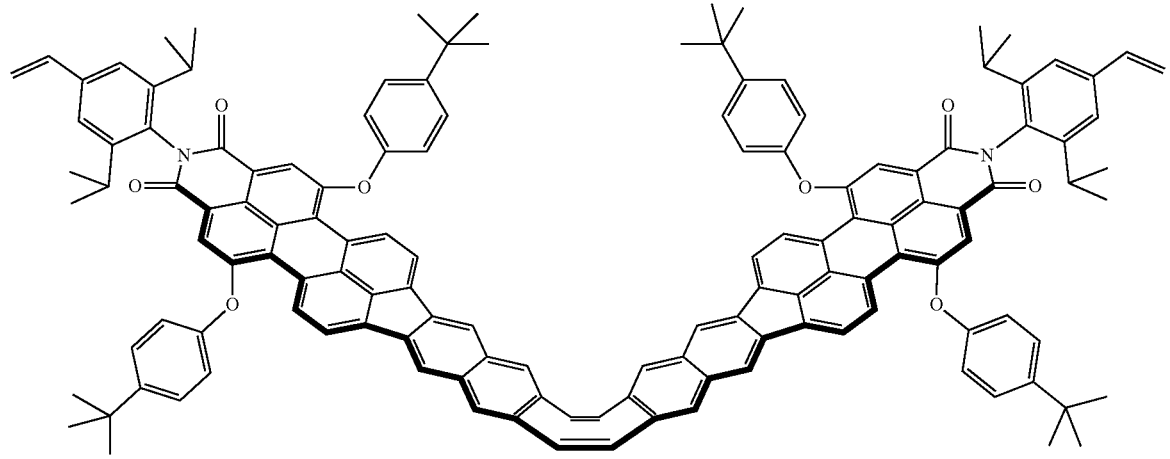

115 116
-continued
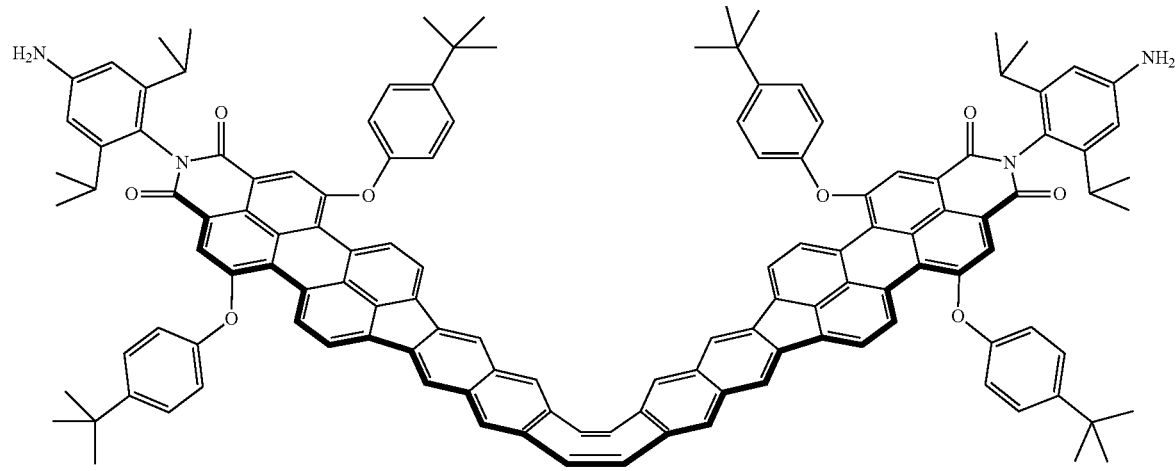
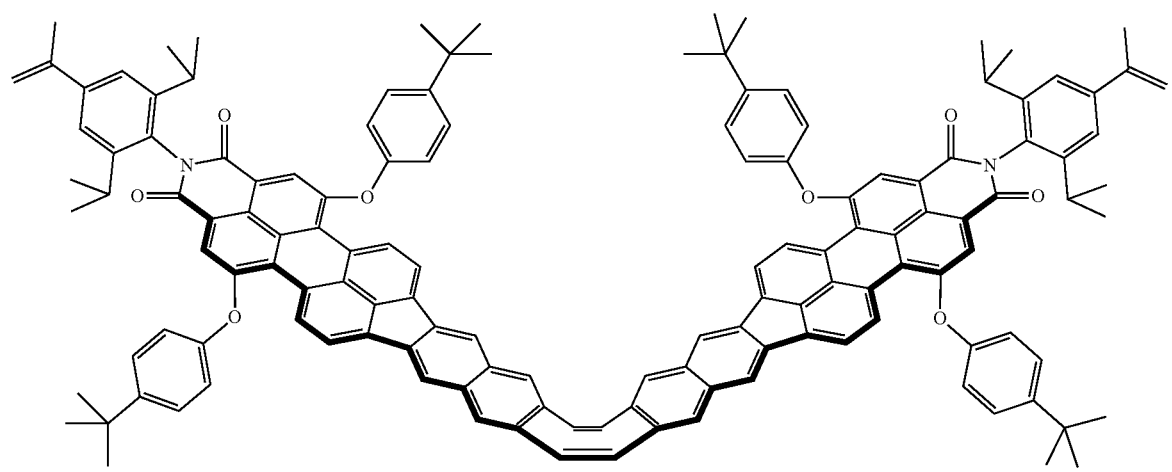
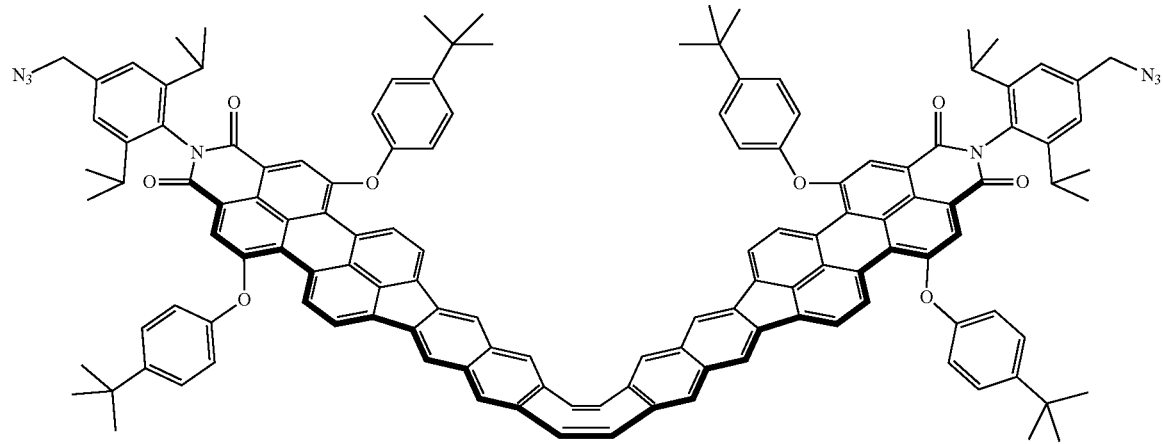

117 118
-continued
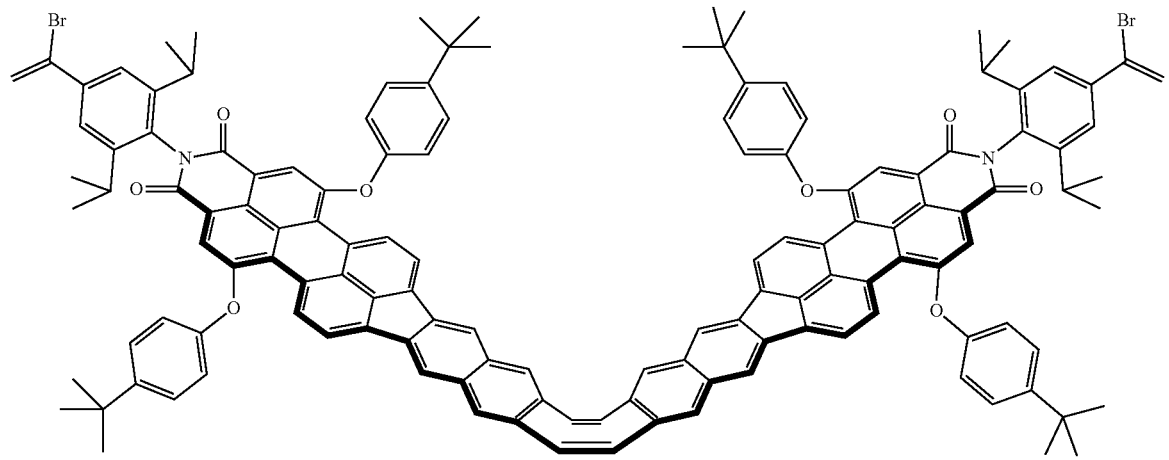
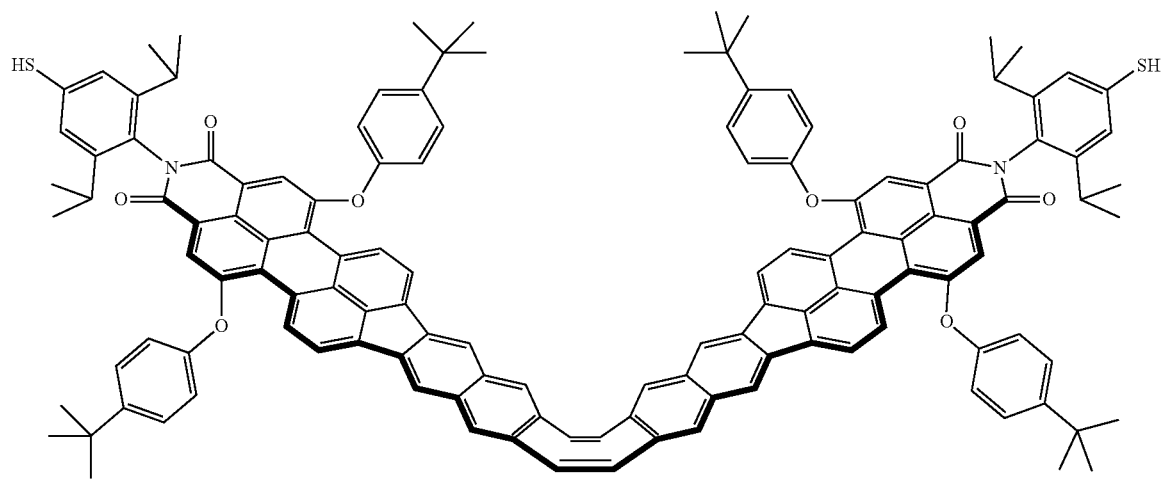
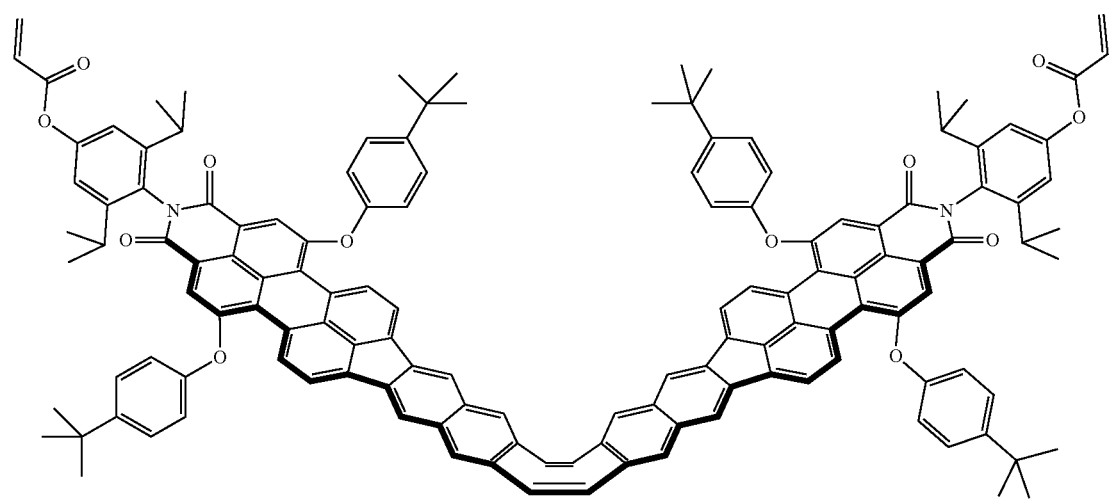

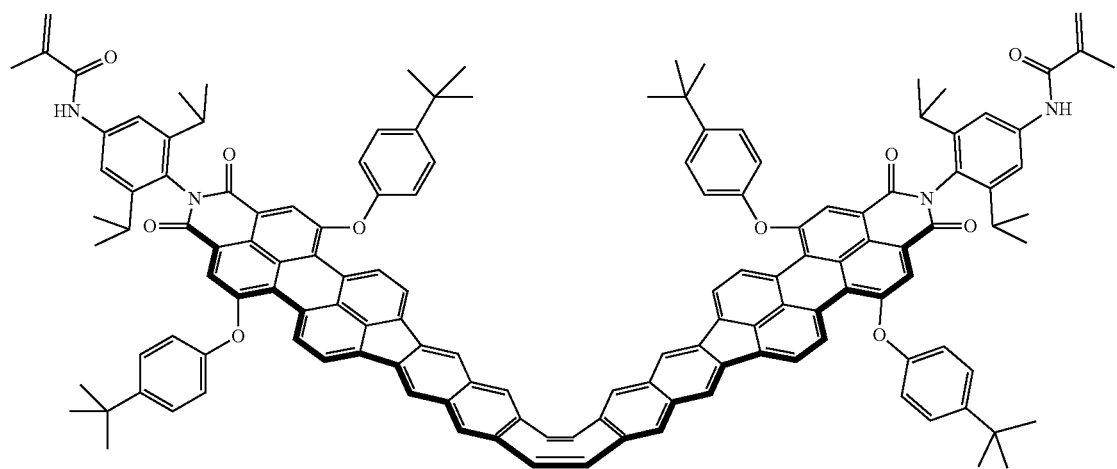
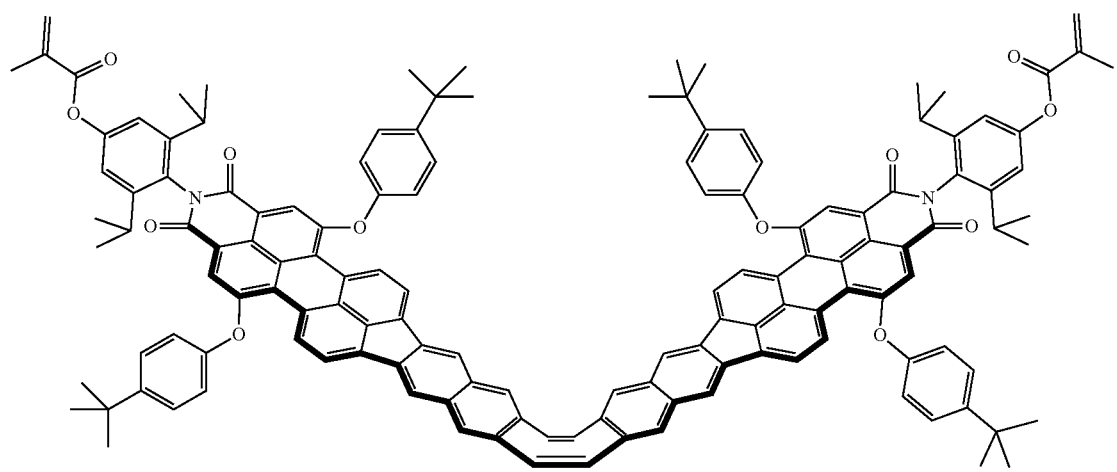
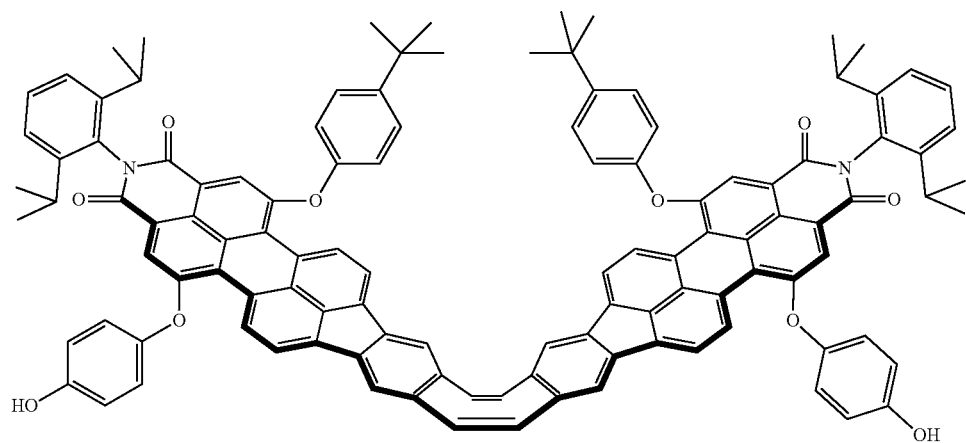

121
122
-continued
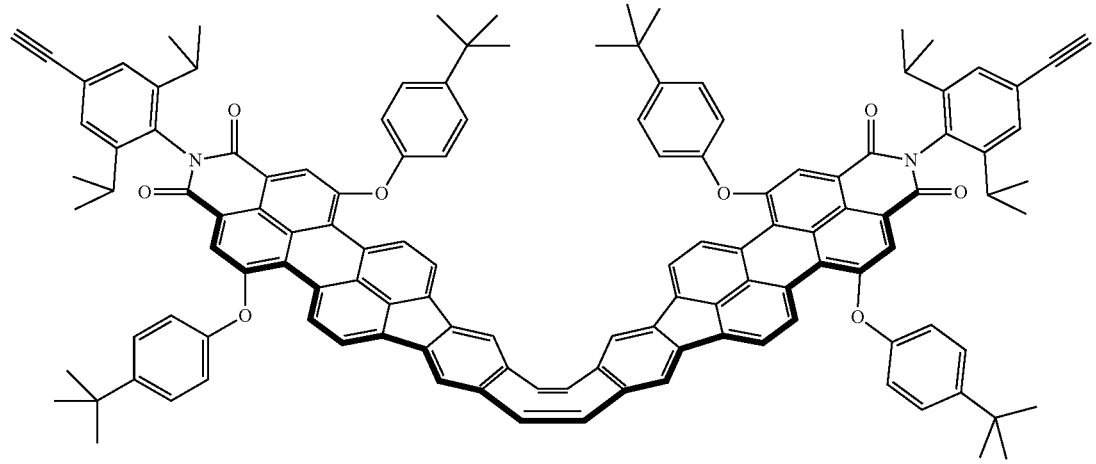
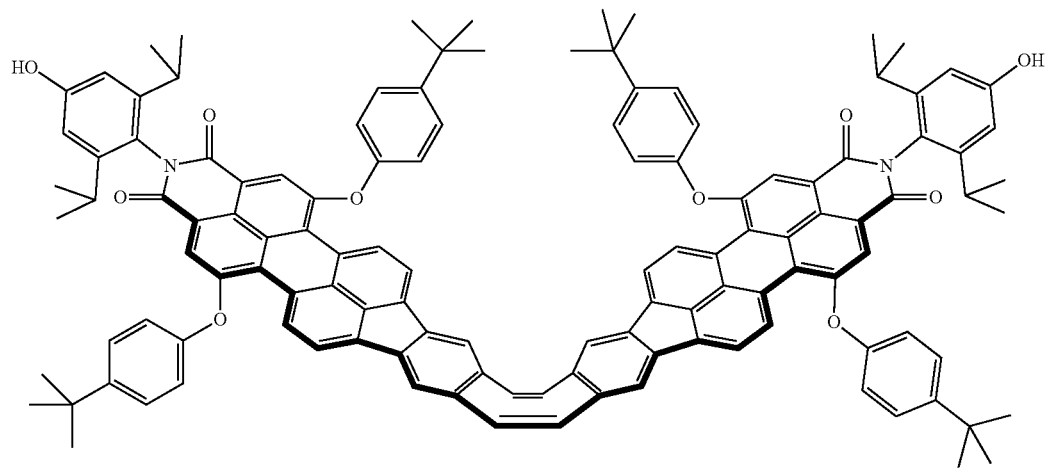
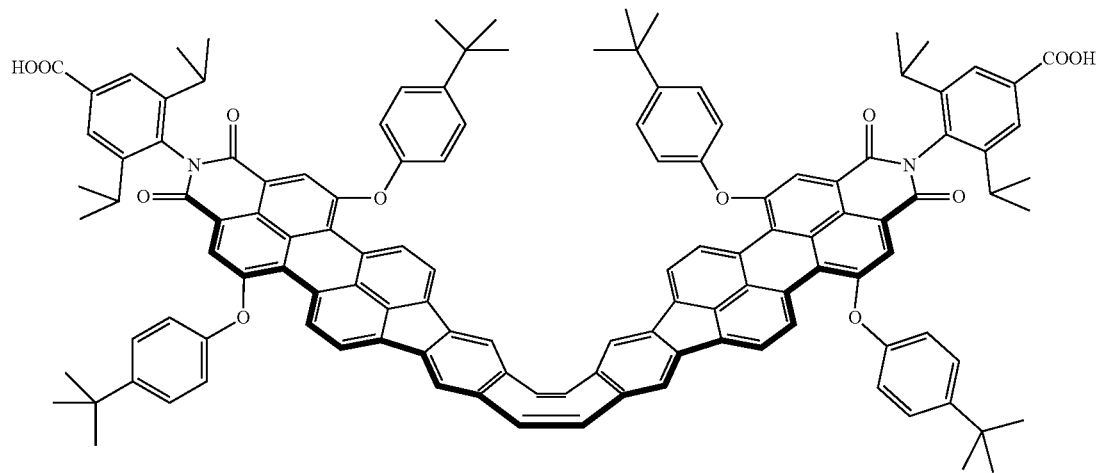

123
-continued
124
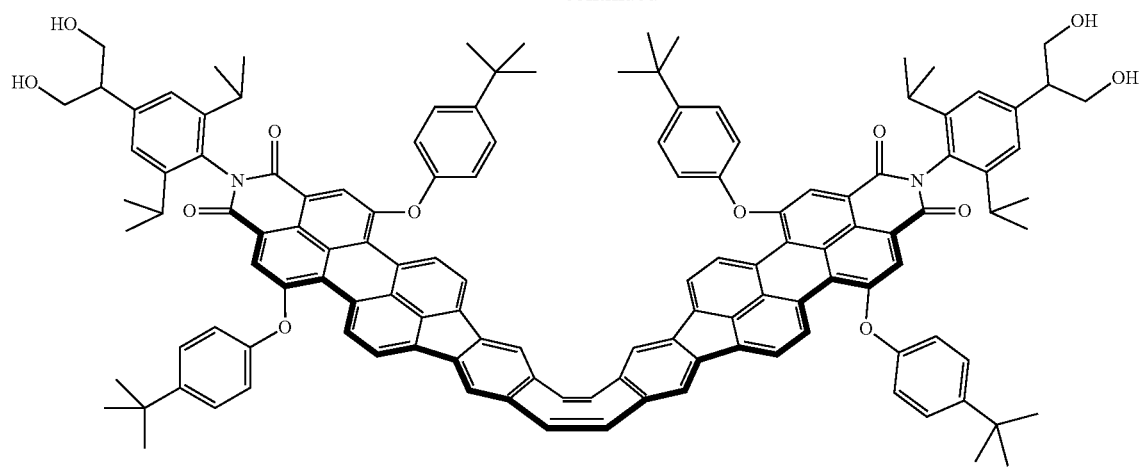
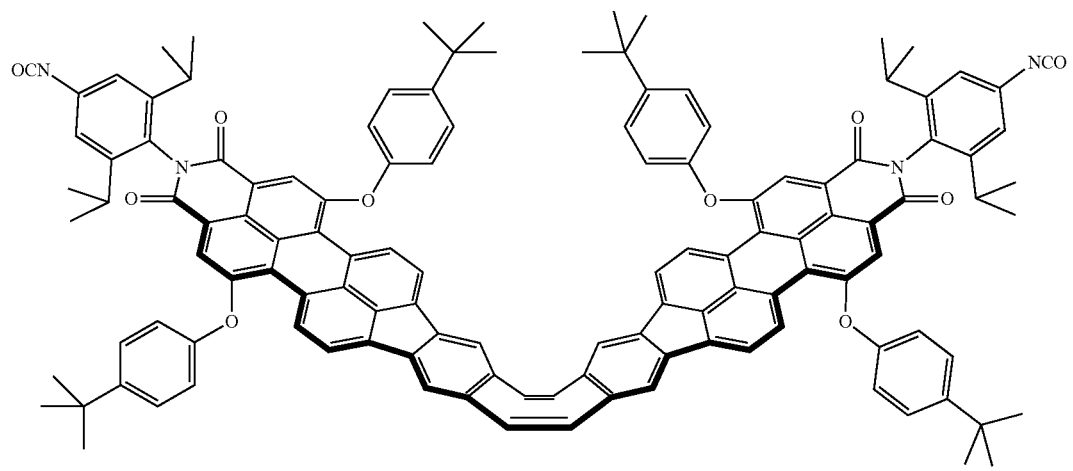
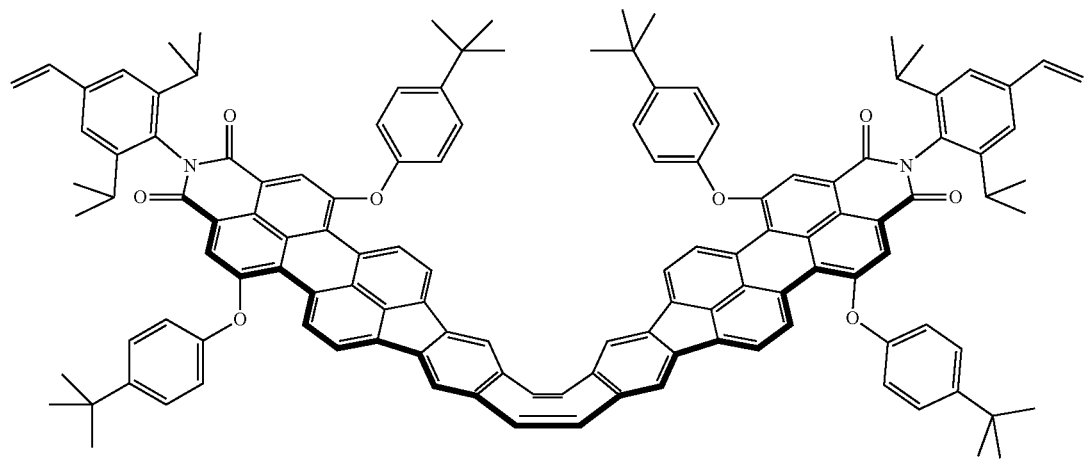

125                                                                       126
-continued
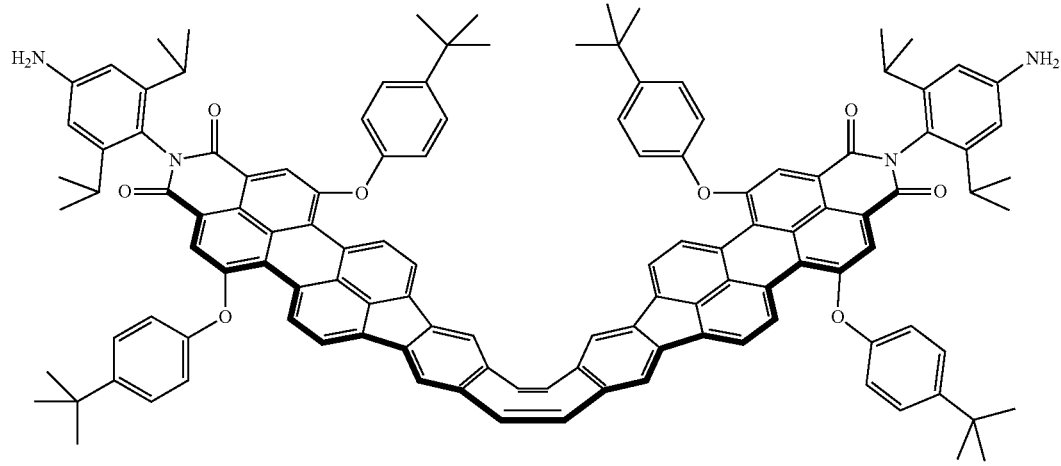
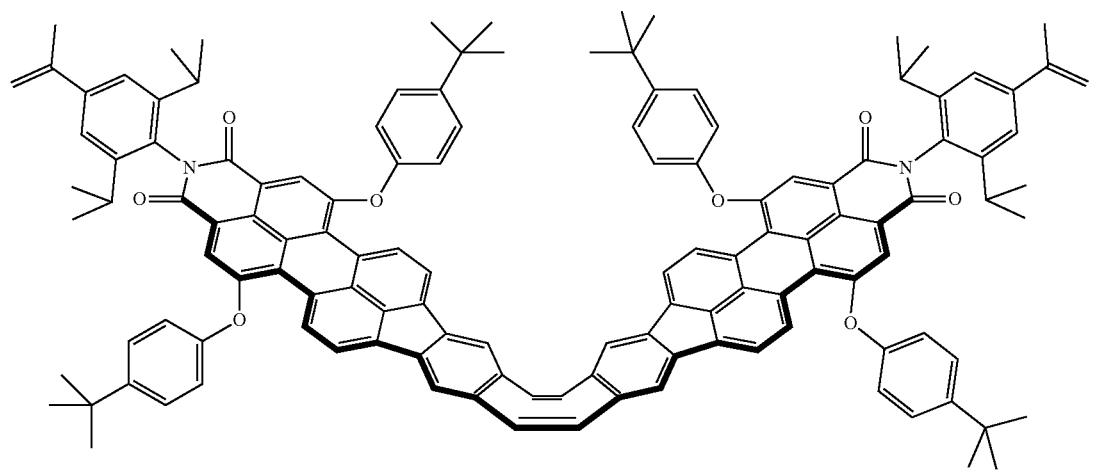
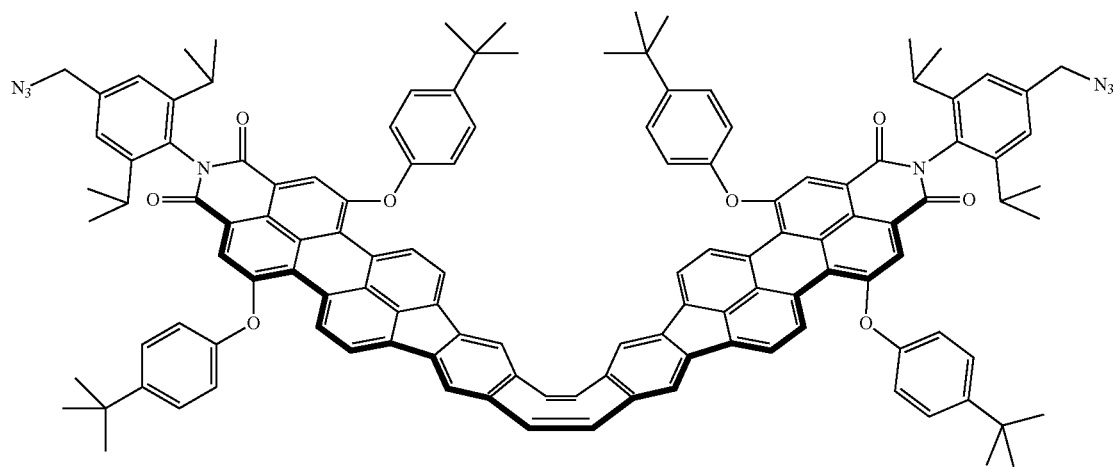

-continued
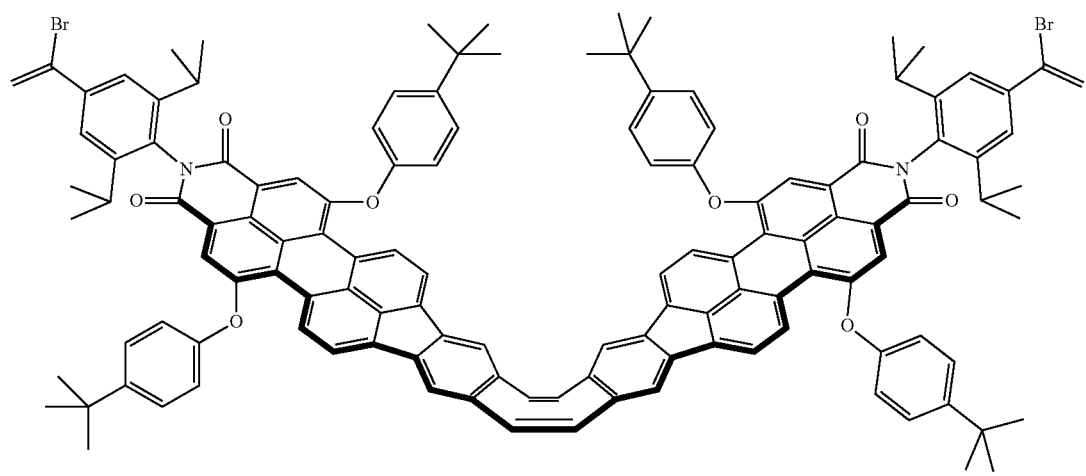
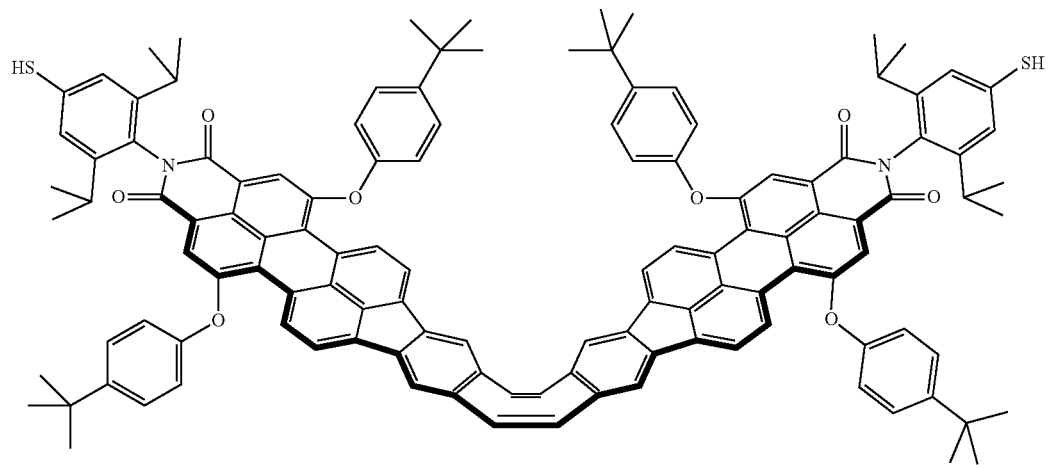
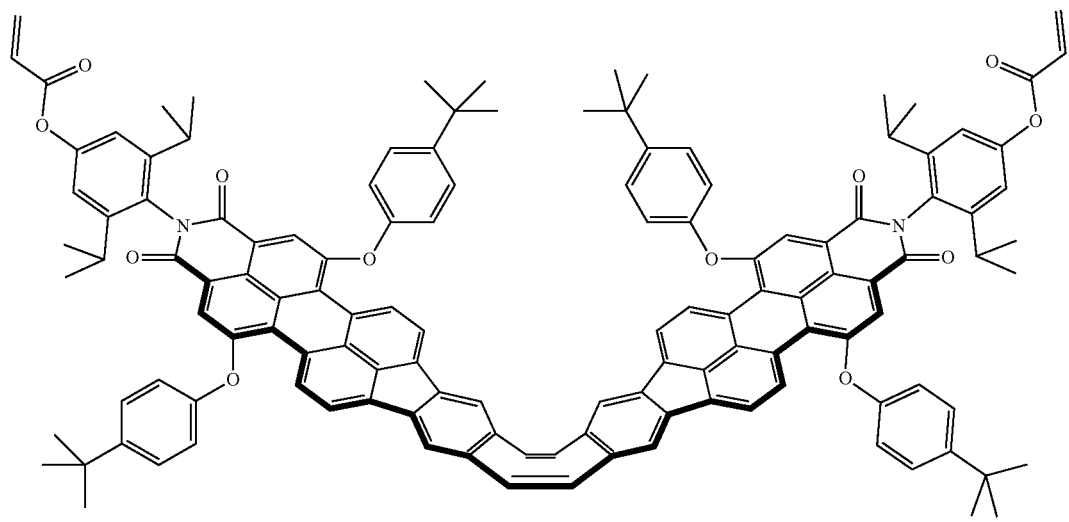

-continued
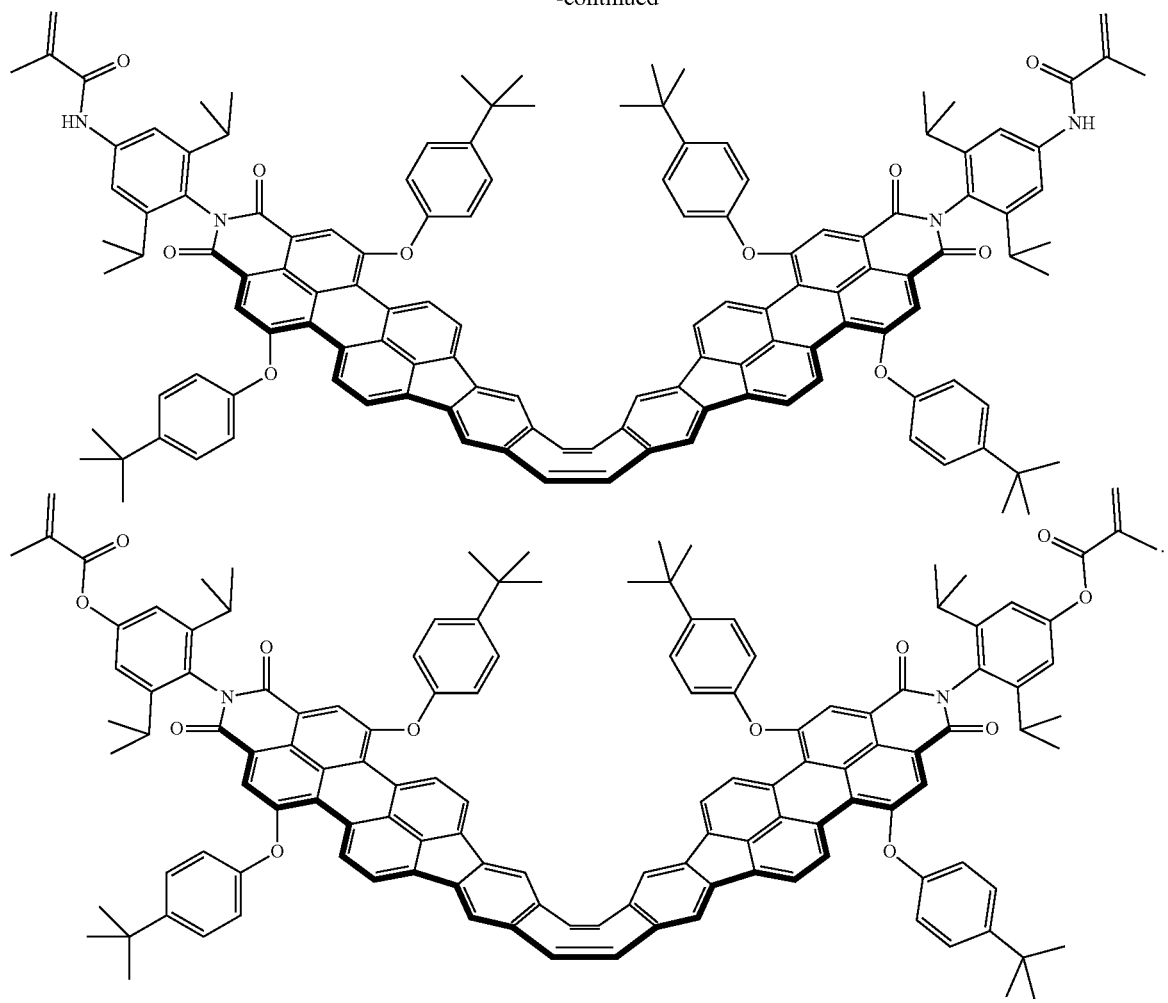
10. The compound according to claim 1, wherein $D^1$ has any of the following structures:
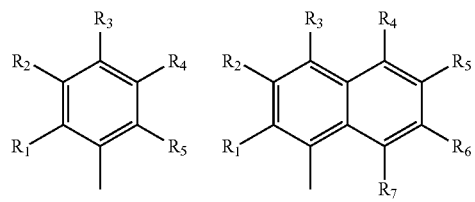
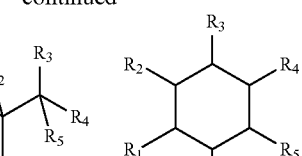
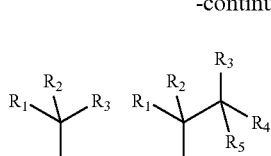
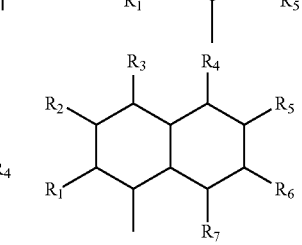
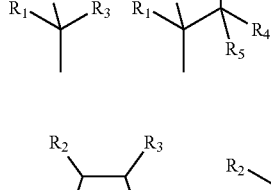
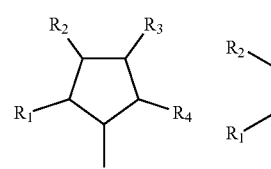
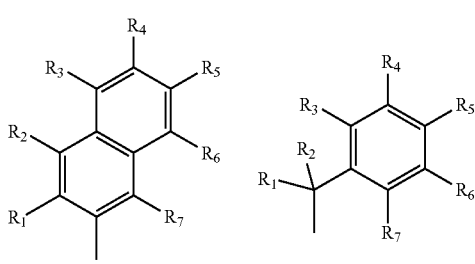
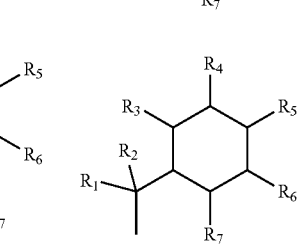
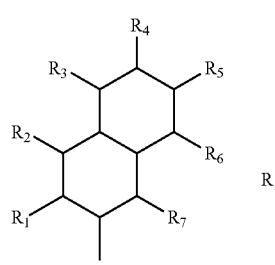

-continued

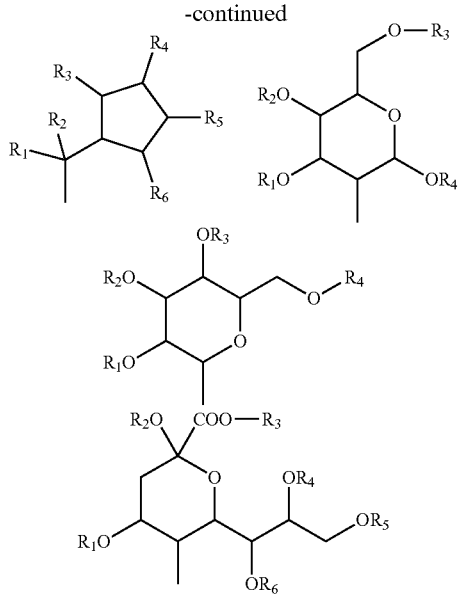

wherein $R_1$ to $R_7$ each denote H, a linear, branched, or cyclic alkyl group with 1-20 carbons, an aryl group with 6-20 carbons, F, Cl, Br, I, $CF_3$, $CCl_3$, CN, or $OCH_3$, and $R_1$ to $R_7$ may be the same or different, and wherein one atom contain in $R_1$ to $R_7$ of $D^1$ can be replaced with $E^1$ in order to form $E^1$-$D^1$- existing in general Formula (5-1).

11. The polymer according to claim 2, wherein $D^1$ has any of the following structures:

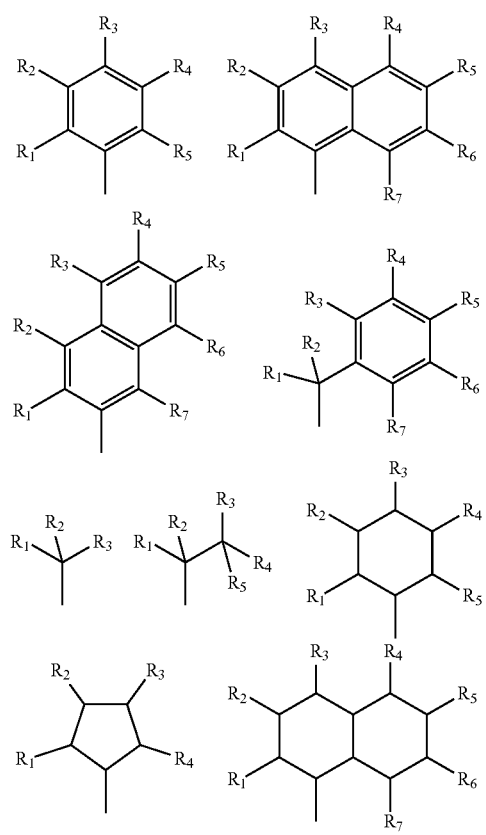

-continued

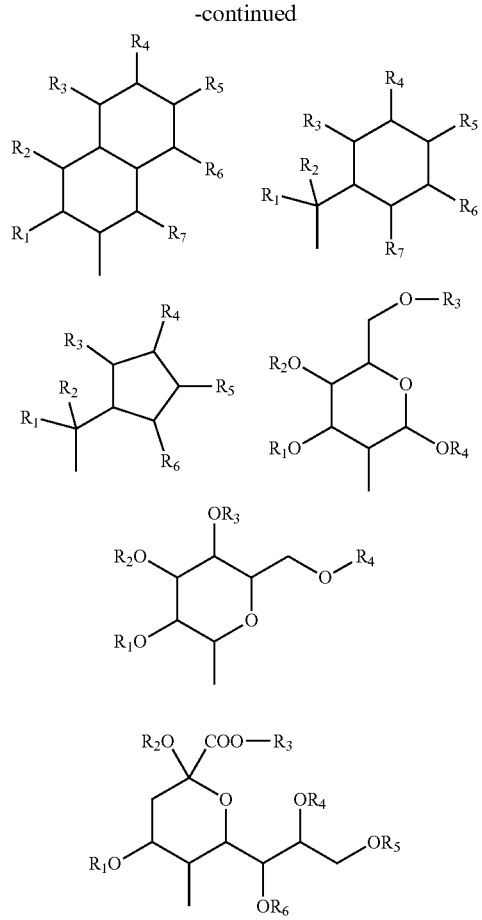

wherein $R_1$ to $R_7$ each denote H, a linear, branched, or cyclic alkyl group with 1-20 carbons, an aryl group with 6-20 carbons, F, Cl, Br, I, $CF_3$, $CCl_3$, CN, or $OCH_3$, and $R_1$ to $R_7$ may be the same or different, and wherein one atom contain in $R_1$ to $R_7$ of $D^1$ can be replaced with $E^1$ in order to form $E^1$-$D^1$- existing in general Formula (5-1).

12. The polymer according to claim 4, wherein $D^1$ has any of the following structures:

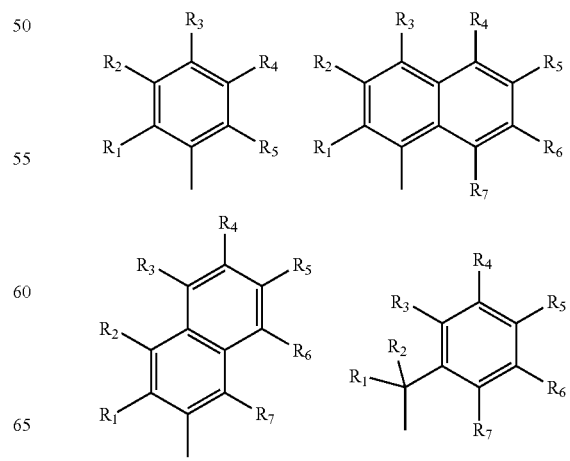

-continued
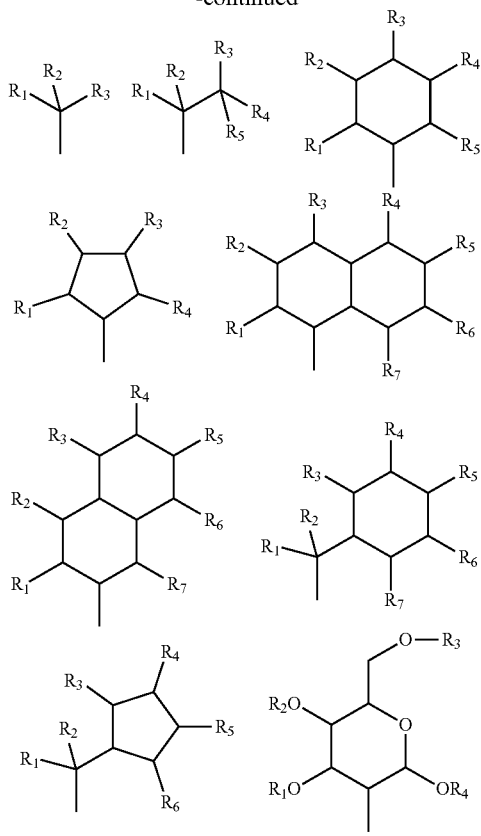
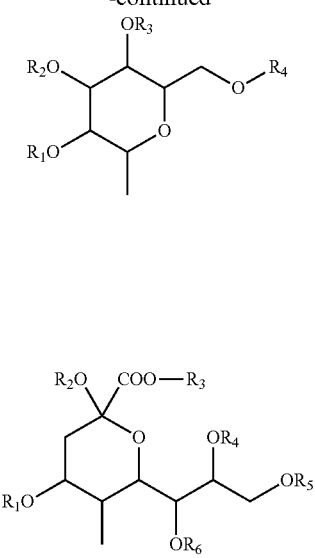
wherein $R_1$ to $R_7$ each denote H, a linear, branched, or cyclic alkyl group with 1-20 carbons, an aryl group with 6-20 carbons, F, Cl, Br, I, $CF_3$, $CCl_3$, CN, or $OCH_3$, and $R_1$ to $R_7$ may be the same or different, and
wherein one atom contain in $R_1$ to $R_7$ of $D^1$ can be replaced with $E^1$ in order to form $E^1$-$D^1$- existing in general Formula (5-1).
\* \* \* \* \*